United States Patent
Helms et al.

(10) Patent No.: US 9,937,126 B2
(45) Date of Patent: Apr. 10, 2018

(54) WNT COMPOSITIONS AND METHODS FOR PURIFICATION

(71) Applicant: The Board of Trustees of the Leland Stanford Junior University, Stanford, CA (US)

(72) Inventors: Jill Helms, Stanford, CA (US); Girija Dhamdhere, San Jose, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 14/910,616

(22) PCT Filed: Oct. 2, 2014

(86) PCT No.: PCT/US2014/058833
§ 371 (c)(1),
(2) Date: Feb. 5, 2016

(87) PCT Pub. No.: WO2015/051122
PCT Pub. Date: Apr. 9, 2015

(65) Prior Publication Data
US 2016/0310424 A1    Oct. 27, 2016

Related U.S. Application Data

(60) Provisional application No. 61/885,827, filed on Oct. 2, 2013.

(51) Int. Cl.
| | |
|---|---|
| *A61L 27/22* | (2006.01) |
| *A61K 9/127* | (2006.01) |
| *A61K 38/17* | (2006.01) |
| *A61K 35/28* | (2015.01) |
| *A61L 27/36* | (2006.01) |
| *A61L 27/38* | (2006.01) |
| *A61L 27/54* | (2006.01) |
| *A61L 27/58* | (2006.01) |
| *C12N 5/077* | (2010.01) |

(52) U.S. Cl.
CPC .............. *A61K 9/127* (2013.01); *A61K 35/28* (2013.01); *A61K 38/1709* (2013.01); *A61L 27/227* (2013.01); *A61L 27/365* (2013.01); *A61L 27/3687* (2013.01); *A61L 27/3834* (2013.01); *A61L 27/3847* (2013.01); *A61L 27/54* (2013.01); *A61L 27/58* (2013.01); *C12N 5/0669* (2013.01); *A61L 2300/412* (2013.01); *A61L 2300/604* (2013.01); *A61L 2300/626* (2013.01); *A61L 2430/02* (2013.01); *C12N 2501/415* (2013.01)

(58) Field of Classification Search
None
See application file for complete search history.

(56) References Cited

U.S. PATENT DOCUMENTS

| | | |
|---|---|---|
| 2008/0226707 A1 | 9/2008 | Helms et al. |
| 2012/0115788 A1 | 5/2012 | Helms |
| 2013/0149741 A1* | 6/2013 | Green ................ C12P 21/00 435/69.1 |

FOREIGN PATENT DOCUMENTS

| | | |
|---|---|---|
| WO | 2004/091647 A1 | 10/2004 |
| WO | 2012/097093 A2 | 7/2012 |
| WO | 2013/040309 A2 | 3/2013 |
| WO | 2014/153548 A1 | 9/2014 |
| WO | 2015/009146 A1 | 1/2015 |

OTHER PUBLICATIONS

Doubravska et al., Cell Signal. May 2011;23(5):837-848.*
Willert et al., Nature 423:448-452 (2003).*
Willert et al., "Protocol for the Purification of Wnt Proteins" Web page, retrieved from the Internet: URL: http://web.stanford.edu/~rnusse/assays/W3aPurif.htm, Apr. 21, 2003, pp. 1-4.
Van Der Valk et al., "Optimization of Chemically Defined Cell Culture Media-Replacing Fetal Bovine Serum in Mammalian In Vitro Methods", Science Direct Toxicolln Vitro, Jun. 2010, pp. 1053:1063; vol. 24, No. 4, Elsevier, Amsterdam, Netherlands.
Takada et al., "Monounsaturated Fatty Acid Modification of Wnt Protein: Its Role in Wnt Secretion", Dev Cell. Dec. 2006, pp. 791-801, vol. 11, No. 6, Elsevier, Amsterdam, Netherlands.
Strausberg et al., "Generation and Initial Analysis of More Than 15,000 Full-Length Human and Mouse eDNA Sequences", Proc Nail Acad Sci US A. 24 Dec. 24, 2002, pp. 16899-16903, vol. 99, No. 26: Genbaank Supplement, pp. 1-2; PNAS, Washington, DC.
Roelink et al., "Expression of Two Members of the Wnt Family during Mouse Development—Restricted Temporal and Spatial Patterns in the Developing Neural Tube", Genes Dev. Mar. 1991, pp. 381-388, vol. 5, No. 3; Genbank Supplement, p. 1; PMID: 2001840, Cold City Harbor Lab Press, Spring Harbor, NY.
Rawicz. et al., "Effect of Chain Length and Unsaturation on Elasticity of Lipid Bilayers", Biophys J. Jul. 2000, pp. 328-339, vol. 79, No. 1, Biophysical Society, Rockville, Maryland.
Morrell et al., "Liposomal Packaging Generates Wnt Protein with In Vivo Biological Activity", PLOS One, Aug. 13, 2008, p. 1-9, vol. 3. No. 8, PLOS, San Francisco, California.

* cited by examiner

*Primary Examiner* — Daniel C Gamett
(74) *Attorney, Agent, or Firm* — Pamela J. Sherwood; Bozicevic, Field & Francis LLP

(57) ABSTRACT

Disclosed herein are methods, processes, compositions, and kits for generating bone graft materials for use at a site of bone defect that utilizes a composition which contains liposomal Wnt polypeptide, such as liposomal Wnt3a polypeptide, liposomal Wnt5a polypeptide, or liposomal Wnt10b polypeptide. Also disclosed herein are methods, processes, compositions, and kits for enhancing mammalian bone marrow cells that utilizes a composition which contains liposomal Wnt polypeptide, such as liposomal Wnt3a polypeptide, liposomal Wnt5a polypeptide, or liposomal Wnt10b polypeptide.

19 Claims, 27 Drawing Sheets

Purification Scheme for WNT3A and L-WNT3A

Fig. 2
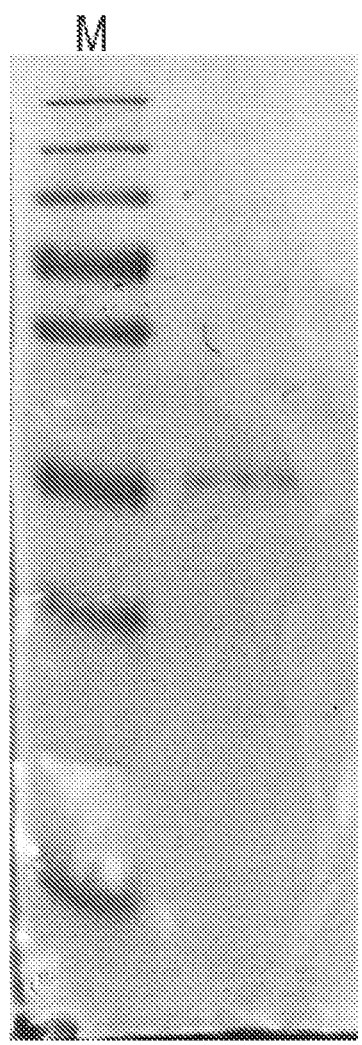
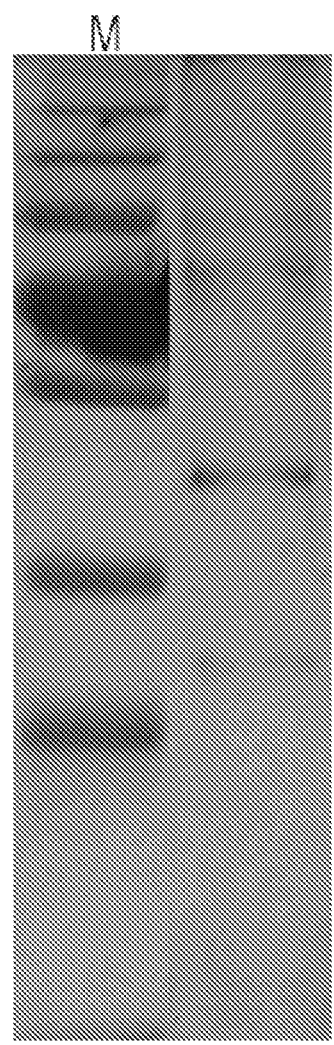
WNT3A

US 9,937,126 B2

WNT COMPOSITIONS AND METHODS FOR PURIFICATION

BACKGROUND OF THE INVENTION

Wnt proteins form a family of highly conserved secreted signaling molecules that bind to cell surface receptors encoded by the Frizzled and low-density lipoprotein receptor related proteins (LRPs). The WNT gene family consists of structurally related genes which encode secreted signaling proteins. These proteins have been implicated in oncogenesis and in several developmental processes, including regulation of cell fate and patterning during embryogenesis. Once bound, the ligands initiate a cascade of intracellular events that eventually lead to the transcription of target genes through the nuclear activity of β-catenin and the DNA binding protein TCF (Clevers H, 2004 Wnt signaling: Ignorrin the dogma. *Curr Biol* 14: R436-R437; Nelson & Nusse 2004 Convergence of Wnt, beta-catenin, and cadherin pathways. *Science* 303: 1483-1487; Gordon & Nusse 2006 Wnt signaling: Multiple pathways, multiple receptors, and multiple transcription factors. *J Biol Chem* 281: 22429-22433).

Wnt proteins are also involved in a wide variety of cellular decisions associated with the program of osteogenesis. For example, Wnt proteins regulate the expression level of sox9, which influences the commitment of mesenchymal progenitor cells to a skeletogenic fate. Wnt proteins influence the differentiation of cells, into either osteoblasts or chondrocytes. In adult animals, there is evidence that Wnt signaling regulates bone mass. For example, mutations in the human Wnt co-receptor LRP5 are associated with several high bone mass syndromes, including osteoporosis type I, and endosteal hyperostosis or autosomal dominant osteosclerosis, as well as a low bone mass disease, osteoporosis-pseudoglioma. Increased production of the Wnt inhibitor Dkkl is associated with multiple myeloma, a disease that has increased bone resorption as one of its distinguishing features. For further details, see, S. Minear et al., Wnt proteins promote bone regeneration. *Sci. Transl. Med.* 2, 29ra30 (2010); and Zhao et al., Controlling the in vivo activity of Wnt liposomes, *Methods Enzyrnol* 465: 331-47 (2009).

SUMMARY OF THE INVENTION

Disclosed herein, in certain embodiments, is a composition comprising a functionally active Wnt3a polypeptide and an aqueous solution comprising liposomes, wherein the functionally active Wnt3a polypeptide comprises a lipid modification at an amino acid position corresponding to amino acid residue 209 as set forth in SEQ ID NO:1. In some embodiments, the functionally active Wnt3a polypeptide is not lipid modified at an amino acid position corresponding to amino acid residue 77 as set forth in SEQ ID NO:1. In some embodiments, the functionally active Wnt3a polypeptide is integrated into the liposomal membrane. In some embodiments, the functionally active Wnt3a polypeptide protrudes from the liposomal membrane onto the outer surface of the lipid membrane. In some embodiments, the functionally active Wnt3a polypeptide is not incorporated into the aqueous core of the liposome. In some embodiments, the functionally active Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the functionally active Wnt3a polypeptide comprises the amino acid sequence as set forth in SEQ ID NO:1. In some embodiments, the concentration of the functionally active Wnt3a polypeptide is between about 5 µg/µL and about 15 µg/µL, or about 8 µg/µL and about 12 µg/µL. In some embodiments, the phospholipid comprising the liposome has a tail carbon length of between about 12 carbons and about 14 carbons. In some embodiments, the phospholipid comprising the liposome has a phase transition temperature from about 10° C. to about 25° C., about 15° C. to about 25° C., or about 20° C. to about 25° C. In some embodiments, the liposome has a net charge of 0 at a pH of between about 6.5 and about 8.0, about 7.0 and about 7.8, or about 7.2 and about 7.6. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the Wnt3a polypeptide is mammalian Wnt3a polypeptide. In some embodiments, the mammal is a human. In some embodiments, the lipid modification is palmitoylation. In some embodiments, the Wnt3a polypeptide is further glycosylated. In some embodiments, the composition is a stable composition. In some embodiments, the composition is stable up to about 106 days without substantial loss of activity. In some embodiments, the composition is stable at a temperature between about 1° C. and about 8° C. In some embodiments, the composition is stable under nitrogen.

Disclosed herein, in certain embodiments, is a composition comprising a functionally active mammalian Wnt polypeptide and an aqueous solution comprising liposomes, wherein the phospholipids comprising the liposomes have a phase transition temperature from about 10° C. to about 25° C. Also disclosed herein, in certain embodiments, is a composition comprising a functionally active mammalian Wnt polypeptide and an aqueous solution comprising liposomes, wherein the phospholipids comprising the liposomes have a tail carbon length of between about 12 carbons and about 14 carbons. In some embodiments, the Wnt polypeptide is integrated into the liposomal membrane. In some embodiments, the Wnt polypeptide protrudes from the liposomal membrane onto the outer surface of the lipid membrane. In some embodiments, the Wnt polypeptide is not incorporated into the aqueous core of the liposome. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt polypeptide is Wnt5a polypeptide or Wnt10b polypeptide. In some embodiments, the concentration of the Wnt polypeptide is between about 5 µg/µL and about 15 µg/µL, or about 8 µg/µL and about 12 µg/µL. In some embodiments, the liposome has a net charge of 0 at a pH of between about 6.5 and about 8.0. In some embodiments, the liposome has a net positive charge or a net negative charge at a pH of between about 6.5 and about 8.0. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the mammal is a human. In some embodiments, the lipid modification is palmitoylation. In some embodiments, the Wnt polypeptide is further glycosylated. In some embodiments, the composition is a stable composition. In some embodiments, the composition is stable up to about 106 days without substantial loss of activity. In some embodiments, the composition is stable at a temperature between about 1° C. and about 8° C. In some embodiments, the composition is stable under nitrogen.

Disclosed herein, in certain embodiments, is a method of preparing a liposomal Wnt3a polypeptide, comprising: (a) harvesting Wnt3a polypeptides from a conditioned media comprising mammalian cells; (b) introducing the Wnt3a polypeptides to an ion-exchange column immobilized with a sulfonated polyaromatic compound; (c) eluting the Wnt3a polypeptides from the ion-exchange column utilizing a step gradient; and (d) contacting the Wnt3a polypeptides from step (c) with an aqueous solution of liposomes. In some embodiments, the contacting occurs at a temperature between about 21° C. and about 25° C. In some embodiments, the time of contacting is between about 30 minutes and about 24 hours. In some embodiments, the step gradient comprises a first gradient and a second gradient. In some embodiments, the first gradient comprises a buffer solution comprising 50 mM potassium chloride, and the second gradient comprises a buffer solution comprising between about 150 mM potassium chloride and about 1.5M potassium chloride. In some embodiments, the buffer solution further comprises a detergent. In some embodiments, the detergent is CHAPS or Triton X-100. In some embodiments, the conditioned media comprises up to 10% fetal bovine serum. In some embodiments, the mammalian cells are Chinese hamster ovary (CHO) cells. In some embodiments, the yield of the Wnt3a polypeptides after step (c) is between about 60% and about 90%. In some embodiments, the phospholipid comprising the liposome has a tail carbon length of between about 12 carbons and about 14 carbons. In some embodiments, the phospholipid comprising the liposome has a phase transition temperature from about 10° C. to about 25° C., about 15° C. to about 25° C., or about 20° C. to about 25° C. In some embodiments, the liposome has a net charge of 0 at a pH of between about 6.5 and about 8.0, about 7.0 and about 7.8, or about 7.2 and about 7.6. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt3a polypeptide is mammalian Wnt3a polypeptide. In some embodiments, the mammal is a human. In some embodiments, the conditioned media comprises a serum or a serum substitute. In some embodiments, the conditioned media comprises a serum. In some embodiments, the serum is a fetal bovine serum. In some embodiments, the serum concentration is between about 0.1% and about 15% in the conditioned media. In some embodiments, the conditioned media comprises a serum substitute. In some embodiments, the serum substitute is a lipid based substitute. In some embodiments, the conditioned media is a serum-free media. In some embodiments, the lipid modification is palmitoylation. In some embodiments, the Wnt3a polypeptide is further glycosylated. In some embodiments, the Wnt3a product is separated from the sample mixture by centrifugation. In some embodiments, the centrifugation time is up to 1 hour at a temperature of between about 1° C. and about 8° C. In some embodiments, the Wnt3a product after centrifugation is resuspended in sterile 1× phosphate buffered saline (PBS). In some embodiments, the Wnt3a product is stable under nitrogen. In some embodiments, the Wnt3a product is stable at a temperature between about 1° C. and about 8° C.

Disclosed herein, in certain embodiments, is a method of preparing a liposomal Wnt polypeptide, comprising contacting a sample comprising Wnt polypeptides to an aqueous solution of liposomes, wherein the phospholipids comprising the liposomes have a phase transition temperature from about 10° C. to about 25° C. Also disclosed herein, in certain embodiments, is a method of preparing a liposomal Wnt polypeptide, comprising contacting a sample comprising Wnt polypeptides to an aqueous solution of liposomes, wherein the phospholipids comprising the liposome have a tail carbon length of between about 12 carbons and about 14 carbons. In some embodiments, the contacting occurs at a temperature between about 21° C. and about 25° C. In some embodiments, the time of contacting is between about 6 hours and about 24 hours. In some embodiments, the method further comprises an additional purification step prior to contacting the Wnt polypeptides to an aqueous solution of liposomes. In some embodiments, the additional purification step is an ion-exchange purification step, a hydrophobic purification step, or an affinity purification step. In some embodiments, the additional purification step is an ion-exchange purification step. In some embodiments, the ion-exchange purification step comprises contacting the sample with sulfonated polyaromatic compound immobilized beads or a column immobilized with a sulfonated polyaromatic compound. In some embodiments, the ion-exchange purification step comprises a step-gradient. In some embodiments, the ion-exchange purification buffer comprises a detergent. In some embodiments, the detergent is CHAPS or Triton X-100. In some embodiments, the additional purification step is a hydrophobic purification step. In some embodiments, the hydrophobic purification step comprises Protein A immobilized beads, or a Protein A column. In some embodiments, the yield of the Wnt polypeptides after the additional purification step is between about 60% and about 99%. In some embodiments, the method further comprises harvesting Wnt polypeptides from a conditioned media comprising cells from an expression cell line. In some embodiments, the expression cell line is a mammalian expression cell line. In some embodiments, the mammalian expression cell line is Chinese hamster ovary (CHO) cell line. In some embodiments, the conditioned media comprises a serum or a serum substitute. In some embodiments, the serum is a fetal bovine serum. In some embodiments, the serum concentration is between about 0.1% and about 15% in the conditioned media. In some embodiments, the conditioned media comprises a serum substitute. In some embodiments, the serum substitute is a lipid based substitute. In some embodiments, the conditioned media is a serum-free media. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt polypeptide is Wnt5a polypeptide or Wnt10b polypeptide. In some embodiments, the liposome has a net charge of 0 at a pH of between about 6.5 and about 8.0, about 7.0 and about 7.8, or about 7.2 and about 7.6. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the Wnt polypeptide is mammalian Wnt polypeptide. In some embodiments, the mammal is a human. In some embodiments, the lipid modification is palmitoylation. In some embodiments, the Wnt polypeptide is further glycosylated. In some embodiments, the Wnt product is separated from the sample mixture by centrifugation. In some embodiments, the centrifugation time is up to 1 hour at a temperature of between about 1° C. and about 8° C. In some embodiments, the Wnt product after centrifugation is resuspended in sterile 1×PBS. In some embodiments, the Wnt product is stable under nitrogen. In some embodiments, the Wnt product is stable at a temperature between about 1° C. and about 8° C.

Disclosed herein, in certain embodiments, is a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt polypeptide. In some embodiments, the mammalian bone marrow cells are rodent bone marrow cells. In some embodiments, the rodent bone marrow cells are harvested from a rodent that is older than 10 months. In some embodiments, the mammalian bone marrow cells are human bone marrow cells. In some embodiments, the human bone marrow cells are obtained from a subject at or older than 35 years of age. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is compared to untreated mammalian bone marrow cells. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt polypeptide. In some embodiments, the decreased expression level in the mammalian bone marrow cells are compared to untreated mammalian bone marrow cells. In some embodiments, the bone marrow cells further comprises a decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the mammalian bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the human bone marrow cells post treatment with liposomal Wnt polypeptide exhibit biomarker expression levels that are observed in a human subject younger than 35 years of age. In some embodiments, the liposomal Wnt polypeptide comprises Wnt polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1, and is not lipid modified at an amino acid position corresponding to amino acid residue 77 as set forth in SEQ ID NO:1. In some embodiments, the Wnt polypeptide is Wnt5a polypeptide or Wnt10b polypeptide.

Disclosed herein, in certain embodiments, is a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt polypeptide.

In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is compared to untreated mammalian bone marrow cells. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt polypeptide. In some embodiments, the decreased expression level in the mammalian bone marrow cells are compared to untreated mammalian bone marrow cells. In some embodiments, the bone marrow cells further comprises a decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the mammalian bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the human bone marrow cells post treatment with liposomal Wnt polypeptide exhibit biomarker expression levels that are observed in a human subject younger than 35 years of age. In some embodiments, the liposomal Wnt polypeptide comprises Wnt polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1, and is not lipid modified at an amino acid position corresponding to amino acid residue 77 as set forth in SEQ ID NO:1. In some embodiments, the Wnt polypeptide is Wnt5a polypeptide or Wnt10b polypeptide.

Disclosed herein, in certain embodiments, is a mammalian bone marrow composition produced by a process comprising contacting isolated mammalian bone marrow cells ex-vivo with a liposomal Wnt polypeptide, wherein the contacting time is between about 30 minutes and about 4 hours. In some embodiments, the contacting temperature is at between about 0° C. and about 37° C., or about 20° C., and about 25° C. In some embodiments, the process further comprises a washing step after contacting to remove free liposomal Wnt polypeptide. In some embodiments, the process further comprises transplanting the liposomal Wnt polypeptide to a site of bone defect. In some embodiments, the bone marrow cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, compared to untreated mammalian bone marrow cells. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt polypeptide. In some embodiments, the decreased expression level in the mammalian bone marrow cells are compared to untreated mammalian bone marrow cells. In some embodiments, the bone marrow cells further comprises decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the mammalian bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells are harvested from femurs, tibiae, and/or iliac crest. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the isolated mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the mammalian bone marrow cells are rodent bone marrow cells. In some embodiments, the rodent bone marrow cells are harvested from a rodent that is older than 10 months. In some embodiments, the mammalian bone marrow cells are human bone marrow cells. In some embodiments, the human bone marrow cells are harvested from a subject at or older than 35 years of age. In some embodiments, the human bone marrow cells post treatment with liposomal Wnt polypeptide exhibit biomarker expression levels that are observed in a subject younger than 35 years of age. In some embodiments, the liposomal Wnt polypeptide comprises Wnt polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt polypeptide is Wnt5a polypeptide or Wnt10b polypeptide.

Disclosed herein, in certain embodiments, is a method of treating a bone defect in a subject, comprising: (a) contacting a sample comprising mammalian bone marrow cells ex-vivo with a liposomal Wnt3a polypeptide; (b) washing the sample to remove free liposomal Wnt3a polypeptide; and (c) transplanting the liposomal Wnt3a polypeptide treated bone graft materials into a site of bone defect. In some embodiments, the contacting temperature is at between about 0° C. and about 37° C., or about 20° C. and about 25° C. In some embodiments, the contacting time is between about 30 minutes and about 4 hours. In some embodiments, the bone marrow cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, compared to untreated mammalian bone marrow cells. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt3a polypeptide. In some embodiments, the decreased expression level in the mammalian bone marrow cells are compared to untreated mammalian bone marrow cells. In some embodiments, the bone marrow cells further comprises decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the mammalian bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells are harvested from femurs, tibiae, and/or iliac crest. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the isolated mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the mammalian bone marrow cells are rodent bone marrow cells. In some embodiments, the rodent bone marrow cells are harvested from a rodent that is older than 10 months. In some embodiments, the mammalian bone marrow cells are human bone marrow cells. In some embodiments, the human bone marrow cells are harvested from a subject at or older than 35 years of age. In some embodiments, the human bone marrow cells post treatment with liposomal Wnt3a polypeptide exhibit biomarker expression levels that are observed in a subject younger than 35 years of age. In some embodiments, the liposomal Wnt3a polypeptide comprises Wnt3a polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1.

Disclosed herein, in certain embodiments, is a method of treating a bone defect in a subject, comprising: (a) contacting a sample comprising mammalian bone marrow cells ex-vivo with a liposomal Wnt polypeptide; (b) washing the sample to remove free liposomal Wnt polypeptide; and (c) transplanting the liposomal Wnt polypeptide treated bone graft materials into a site of bone defect. In some embodiments, the contacting temperature is at between about 0° C. and about 37° C. or about 20° C. and about 25° C. In some embodiments, the contacting time is between about 30 minutes and about 4 hours. In some embodiments, the bone marrow cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, compared to untreated mammalian bone marrow cells. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt polypeptide. In some embodiments, the decreased expression level in the mammalian bone marrow cells are compared to untreated mammalian bone marrow cells. In some embodiments, the bone marrow cells further comprises decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells are harvested from femurs, tibiae, and/or iliac crest. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the isolated mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the mammalian bone marrow cells are rodent bone marrow cells. In some embodiments, the rodent bone marrow cells are harvested from a rodent that is older than 10 months. In some embodiments, the mammalian bone marrow cells are human bone marrow cells. In some embodiments, the human bone marrow cells are harvested from a subject at or older than 35 years of age. In some embodiments, the human bone marrow cells post treatment with liposomal Wnt polypeptide exhibit biomarker expression levels that are observed in a subject younger than 35 years of age. In some embodiments, the liposomal Wnt polypeptide comprises Wnt polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt polypeptide is Wnt5a polypeptide or Wnt10b polypeptide.

Disclosed herein, in certain embodiments, is a kit for generating bone graft materials comprising the liposomal Wnt polypeptide. In some embodiments, the liposomal Wnt polypeptide is a composition comprising a functionally active mammalian Wnt polypeptide and an aqueous solution comprising liposomes, wherein the phospholipids comprising the liposomes have a phase transition temperature from about 10° C. to about 25° C. In some embodiments, the liposomal Wnt polypeptide is a composition comprising a functionally active mammalian Wnt polypeptide and an aqueous solution comprising liposomes, wherein the phospholipids comprising the liposomes have a tail carbon length of between about 12 carbons and about 14 carbons. In some embodiments, the Wnt polypeptide is integrated into the liposomal membrane. In some embodiments, the Wnt polypeptide protrudes from the liposomal membrane onto the outer surface of the lipid membrane. In some embodiments, the Wnt polypeptide is not incorporated into the aqueous core of the liposome. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1 and is not lipid modified at an amino acid position corresponding to amino acid residue 77 as set forth in SEQ ID NO:1. In some embodiments, the Wnt polypeptide is Wnt5a polypeptide or Wnt10b polypeptide. In some embodiments, the concentration of the Wnt polypeptide is between about 5 µg/µL and about 15 µg/µL, or about 8 µg/µL and about 12 µg/µL. In some embodiments, the liposome has a net charge of 0 at a pH of between about 6.5 and about 8.0. In some embodiments, the liposome has a net positive charge or a net negative charge at a pH of between about 6.5 and about 8.0. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the mammal is a human. In some embodiments, the lipid modification is palmitoylation. In some embodiments, the Wnt polypeptide is further glycosylated. In some embodiments, the composition is a stable composition. In some embodiments, the composition is stable up to about 106 days without substantial loss of activity. In some embodiments, the composition is stable at a temperature between about 1° C. and about 8° C. In some embodiments, the composition is stable under nitrogen.

Disclosed herein, in certain embodiments, is a kit for generating bone graft materials comprising the liposomal Wnt3a polypeptide. In some embodiments, the liposomal Wnt3a polypeptide is a composition comprising a functionally active Wnt3a polypeptide and an aqueous solution comprising liposomes, wherein the functionally active Wnt3a polypeptide comprises a lipid modification at an amino acid position corresponding to amino acid residue 209 as set forth in SEQ ID NO:1. In some embodiments, the functionally active Wnt3a polypeptide is not lipid modified at an amino acid position corresponding to amino acid residue 77 as set forth in SEQ ID NO:1. In some embodiments, the functionally active Wnt3a polypeptide is integrated into the liposomal membrane. In some embodiments, the functionally active Wnt3a polypeptide protrudes from the liposomal membrane onto the outer surface of the lipid membrane. In some embodiments, the functionally active Wnt3a polypeptide is not incorporated into the aqueous core of the liposome. In some embodiments, the functionally active Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the functionally active Wnt3a polypeptide comprises the amino acid sequence as set forth in SEQ ID NO:1. In some embodiments, the concentration of the functionally active Wnt3a polypeptide is between about 5 µg/µL and about 15 µg/µL, or about 8 µg/µL and about 12 µg/µL. In some embodiments, the phospholipid comprising the liposome has a tail carbon length of between about 12 carbons and about 14 carbons. In some embodiments, the phospholipid comprising the liposome has a phase transition temperature from about 10° C. to about 25° C., about 15° C. to about 25° C., or about 20° C. to about 25° C. In some embodiments, the liposome has a net charge of 0 at a pH of between about 6.5 and about 8.0, about 7.0 and about 7.8, or about 7.2 and about 7.6. In some embodiments, the phospholipid is 1,2-dimyristoyl-sn-glycero-3-phosphocholine (DMPC). In some embodiments, the liposome further comprises cholesterol. In some embodiments, the concentration of DMPC and cholesterol is defined by a ratio of between about 70:30 and about 100:0. In some embodiments, the Wnt3a polypeptide is mammalian Wnt3a polypeptide. In some embodiments, the mammal is a human. In some embodiments, the lipid modification is palmitoylation. In some embodiments, the Wnt3a polypeptide is further glycosylated. In some embodiments, the composition is a stable composition. In some embodiments, the composition is stable up to about 106 days without substantial loss of activity. In some embodiments, the composition is stable at a temperature between about 1° C. and about 8° C. In some embodiments, the composition is stable under nitrogen.

Disclosed herein, in certain embodiments, is a kit for generating bone graft materials comprising an isolated enhanced mammalian bone marrow cell composition. In some embodiments, the isolated enhanced mammalian bone marrow cell composition is a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt polypeptide. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the enhanced expression level is compared to untreated mammalian bone marrow cells. In some embodiments, the enhanced expression level is between about 2% and about 20% or about 4% and about 10% compared to untreated mammalian bone marrow cells. In some embodiments, the mammalian bone marrow cells further have a decreased expression level in a biomarker selected from SOX9 and PPARγ after treatment with liposomal Wnt polypeptide. In some embodiments, the decreased expression level in the mammalian bone marrow cells are compared to untreated mammalian bone marrow cells. In some embodiments, the bone marrow cells further comprises a decrease in apoptosis level compared to untreated mammalian bone marrow cells. In some embodiments, the decrease in apoptosis level is about 50%. In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some embodiments, the new bone growth level is compared to new bone growth level of transplanted untreated mammalian bone marrow cells. In some embodiments, the new bone growth level of transplanted treated mammalian bone marrow cells is between about 1% and about 20% or about 5% and about 12% compared to the new bone growth level of transplanted untreated mammalian bone marrow cells. In some embodiments, the mammalian bone marrow cells include adherent and non-adherent bone marrow cells. In some embodiments, the mammalian bone marrow cells are adherent bone marrow cells. In some embodiments, the adherent bone marrow cells include bone marrow stem cells and bone marrow progenitor cells. In some embodiments, the adherent bone marrow cells include bone marrow stromal cells. In some embodiments, the mammalian bone marrow cells are autologous bone marrow cells. In some embodiments, the autologous bone marrow cells include adherent and non-adherent bone marrow cells. In some embodiments, the autologous bone marrow cells are adherent bone marrow cells. In some embodiments, the autologous bone marrow cells include bone marrow stem cells and bone marrow progenitor cells. In some embodiments, the autologous bone marrow cells include bone marrow stromal cells. In some embodiments, the mammalian bone marrow cells are allogeneic bone marrow cells. In some embodiments, the allogeneic bone marrow cells include adherent and non-adherent bone marrow cells. In some embodiments, the allogeneic bone marrow cells are adherent bone marrow cells. In some embodiments, the allogeneic bone marrow cells include bone marrow stem cells and bone marrow progenitor cells. In some embodiments, the allogeneic bone marrow cells include bone marrow stromal cells. In some embodiments, the human bone marrow cells post treatment with liposomal Wnt polypeptide exhibit biomarker expression levels that are observed in a human subject younger than 35 years of age. In some embodiments, the liposomal Wnt polypeptide comprises Wnt polypeptides and an aqueous solution of liposomes. In some embodiments, the phospholipids comprising the liposomes have a phase transition temperature from about 10° C. to about 25° C. In some embodiments, the phospholipids comprising the liposomes have a tail carbon length of between about 12 carbons and about 14 carbons. In some embodiments, the Wnt polypeptide is Wnt3a polypeptide. In some embodiments, the Wnt3a polypeptide comprises at least about 30%, about 40%, about 50%, about 60%, about 70%, about 80%, about 90%, or about 95% sequence identity to the amino acid sequence as set forth in SEQ ID NO:1. In some embodiments, the Wnt3a polypeptide comprises the amino acid sequence as set forth in SEQ ID NO:1. In some embodiments, the Wnt3a polypeptide is lipid modified at an amino acid position corresponding to amino acid residue 209 as set forth in SEQ ID NO:1, and is not lipid modified at an amino acid position corresponding to amino acid residue 77 as set forth in SEQ ID NO:1. In some embodiments, the Wnt polypeptide is Wnt5a polypeptide or Wnt10b polypeptide.

Further aspects and embodiment will be apparent from the rest of the disclosure, and are included within the present invention.

BRIEF DESCRIPTION OF THE DRAWINGS

FIG. 2 indicates SDS PAGE and Coomassie blue staining analyses of Wnt3a.

FIG. 20A indicates Gomori staining of BGM harvested from rat femur, (FIG. 20B) the iliac crest, and (FIG. 20C) the tibia. FIG. 20D is the quantitative RT-PCR analyses of endogenous osteogenic gene expression in freshly harvested rat BGM from the indicated sources. FIG. 20E illustrates a schematic of experimental design, where autologous BGM is transplanted into the SRC of rats. FIG. 20F exemplifies representative tissue sections of iliac crest BGM on post-transplant day 7, stained to detect BrdU incorporation. Dotted lines indicate trabecular bone chips included in the BGM. FIG. 20G, FIG. 20H, and FIG. 20I are Runx2, Sox9, and PPARγ expressions, respectively. FIG. 20J shows representative tissue sections of BGM stained with Aniline blue to detect osteoid matrix; asterisks indicate new bone matrix as opposed to old bone chips (yellow dotted line). The kidney surface is indicated with a dotted white line in this panel, and in FIG. 20G. FIG. 20K is Safranin O/Fast green histology to detect proteoglycan-rich cartilage (red), and FIG. 20L is Gomori trichrome staining to detect adipocytes. Abbreviations: BrdU, bromodeoxyuridine; PPARγ, peroxisome proliferator-activated protein gamma. Scale bars: 50 µm, asterisks: p<0.05.

FIG. 21A indicates GFP$^{+ve}$ cells in Axin2$^{CreERT2}$;R26$^{mTmG}$ mice, visualized by immunostaining of the periosteum and FIG. 21B is endosteum. FIG. 21C is quantification of GFP$^{+ve}$ cells/total cells within specified microscopic fields of view. FIG. 21D indicates GFP$^{+ve}$ cells in the BGM were visualized by fluorescence. FIG. 21E is quantitative absolute RT-PCR results for endogenous Axin2, Lef1, and GAPDH expression in BGM$^{young}$ (green bars) and BGM$^{aged}$ (grey bars). FIG. 21F illustrates western blot analyses for Wnt3a, total beta catenin, Axin2, and beta actin in BGM$^{young}$ (green bars) and BGM$^{aged}$ (grey bars). Scale bars=50 µm. Asterisks: p<0.05.

FIG. 22A indicates quantitative RT-PCR analyses for expression of alkaline phosphatase, Osterix, and Osteocalcin in BGM$^{young}$ (green bars) and BGM$^{aged}$ (grey bars). FIG. 22B is BGM harvested from ACTB-eGFP mice, transplanted into the SRC and visualized under brightfield and FIG. 22C is the detection of the GFP signal in BGM utilizing fluorescent light. FIG. 22D is representative tissue sections stained with Aniline blue (inset) from BGM$^{young}$ (N=5) and (FIG. 22E) BGM$^{aged}$ (N=5). Dotted line indicates the kidney surface. FIG. 22F indicates histomorphometric analyses of Aniline blue$^{+ve}$ pixels within the total area occupied by the BGM on post-transplant day 7. FIG. 22G indicates representative tissue sections stained to detect ALP activity from BGM$^{young}$ (N=5) and (H) BGM$^{aged}$ (N=5). FIG. 22I indicates quantification of ALP$^{+ve}$ pixels within the total area occupied by the BGM on post-transplant day 7. FIG. 22J shows representative tissue sections immunostained for GFP from BGM$^{young}$ (N=5) and (FIG. 22K) BGM$^{aged}$ (N=5). FIG. 22L shows quantification of GFP$^{+ve}$ pixels within the total area occupied by the BGM on post-transplant day 7. Abbreviations: ALP, alkaline phosphatase; Oc, Osteocalcin. Scale bars: 100 µm. Asterisks: p<0.05; double asterisks: p<0.01.

FIG. 23A shows representative tissue sections stained for ALP activity in BGM treated with the murine IgG2α Fc fragment (Ad-Fc) or (FIG. 23B) adenovirus expressing the soluble Wnt antagonist Dkk1 (Ad-Dkk1). FIG. 23C shows representative tissue sections immunostained for PPARγ in BGM treated with Ad-Fc or (FIG. 23D) Ad-Dkk1. FIG. 23E illustrates representative tissue sections immunostained for Dlk1 in BGM treated with Ad-Fc or (FIG. 23F) Ad-Dkk1. FIG. 23G illustrates micro-CT reconstruction to detect bone formation in defect sites that received BGM treated with Ad-Fc or (FIG. 23H) Ad-Dkk1. Original defect is indicated with a dotted red circle. FIG. 23I shows new bone volume (N=5) calculated from micro-CT data±SEM. FIG. 23J indicates aniline blue staining on representative tissue sections from defect sites that received BGM treated with Ad-Fc or (FIG. 23K) Ad-Dkk1. FIG. 23L indicates quantification of new bone volume using histomorphometric analyses. FIG. 23I is PPAR-γ expression in BM grafts treated with Ad-Fc or (FIG. 23J) Ad-Dkk1. Single asterisk p<0.05. Scale bars: A-B, 200 µm, C-F,J-K, 50 µm, G-H, 2 mm.

FIG. 24A indicates BGMs from aged ACTB-eGFP mice, treated with L-PBS or L-WNT3A (0.15 µg/ml) for 1 h then either assayed by qRT-PCR for target gene expression 24 h later, or immediately transplanted into the SRC for 7 days. FIG. 24B illustrates fold change in Axin2 and Lef1 expression in BGM$^{aged}$ treated with either L-PBS (grey bars) or L-WNT3A (blue bars). FIG. 24C are western blot analysis of total beta catenin, Axin2, and beta actin in BGM$^{aged}$ treated with either L-PBS (grey bars) or L-WNT3A (blue bars). After harvesting BGM$^{aged}$ from the SRC on post-transplant day 4, representative tissue sections from (FIG. 24D) L-PBS (N=5) and (FIG. 24E) L-WNT3A were stained for BrdU incorporation (N=5). FIG. 24F indicates quantification of BrdU$^{+ve}$ pixels within a microscopic field of view centered in the middle of the bone grafts. FIG. 24G illustrates representative tissue sections from L-PBS (N=5) and (FIG. 24H) L-WNT3A treated (N=5) samples, stained for BrdU incorporation on post-transplant day 7. FIG. 24I illustrates quantification of BrdU$^{+ve}$ pixels as above. FIG. 24J indicates representative tissue sections from L-PBS (N=5) and (FIG. 24K) L-WNT3A treated (N=5) samples, immunostained for Dlk1 expression on post-transplant day 7. FIG. 24L shows quantification of Dlk1$^{+ve}$ pixels within the total area occupied by the BGM on post-transplant day 7. FIG. 24M shows representative tissue sections from L-PBS (N=5) and (FIG. 24N) L-WNT3A treated (N=5) samples, immunostained for Oc expression on post-transplant day 7. FIG. 24O indicates quantification of Oc$^{+ve}$ pixels as described for Dlk1. FIG. 24P shows representative tissue sections stained with Aniline blue to detect osteoid matrix in L-PBS (N=5) and (FIG. 24Q) L-WNT3A treated (N=5) samples. FIG. 24R indicates histomorphometric quantification of new bone matrix. Abbreviations are described as elsewhere herein. Scale bars: 100 µm. Asterisks: p<0.05; double asterisks: p<0.01.

FIG. 25A shows human MSC cultures were treated with L-PBS or L-WNT3A at 37° C. for the time points indicated and qRT-PCR for Axin2 expression was used to determine Wnt-response. FIG. 25B shows murine SSC were treated with L-PBS or L-WNT3A for 12 h at 37° C. and Wnt response was assayed with qRT-PCR for Axin2 expression. FIG. 25C illustrates quantitative absolute RT-PCR analyses for Axin2 and Lef1 expression in response to 1 h incubation at room temperature with L-PBS (dashed line) or L-WNT3A (0.15 µg/mL; blue line). Data is expressed as a ratio of RNA copies/total RNA content over a 24 h period. FIG. 25D indicates rat spinous processes were exposed via minimal incisions and standardized volumes of autologous BGM from the iliac crest were treated with L-PBS or L-WNT3A for 1 hr then (FIG. 25E) transplanted between the transverses processes of the L4 and L5 vertebrae. FIG. 25F indicates at POD2 Micro-CT acquisitions were performed for graft (pink) treated with L-PBS and (G) L-WNT3A. FIG. 25H indicates at POD49 Micro-CT acquisitions were again performed to evaluate the bone growth of the transplants treated with L-PBS (gray) and (FIG. 25I) L-WNT3A (blue). FIG. 25J indicates transplant growth that was graphed for each of the treatment groups as fold volume, comparing each graft size on POD2 to its size on POD49 (indicated by the colors as stated above). Abbreviations: L4, Lumbar #4, L5, Lumbar #5, AP, apical process, SP, spinous process, TP, transverse process, POD, post-operation day.

FIG. 27A illustrates GFP immunostaining of BGM$^{aged}$ and (FIG. 27B) BGM$^{ACT}$ after 4d in the SRC. FIG. 27C shows quantification of GFP$^{+ve}$ pixels over total pixels occupied by the BGM on post-transplant day 4. FIG. 27D shows TUNEL staining of BGM$^{aged}$ and (FIG. 27E) BGM$^{ACT}$ after 4d in the SRC. FIG. 27F shows quantification of TUNEL$^{+ve}$ cells over total DAPI$^{+ve}$ pixels within the total area occupied by the BGMs on post-transplant days 4. FIG. 27G shows TUNEL staining of BGM$^{aged}$ and (FIG. 27H) BGM$^{ACT}$ after 7d in the SRC. FIG. 27I shows quantification of TUNEL$^{+ve}$ cells over total DAPI$^{+ve}$ pixels within the total area occupied by the BGMs on post-transplant day 7. FIG. 27J illustrates tissue sections stained for tartrate resistant acid phosphatase (TRAP) activity to detect osteoclasts in BGM$^{aged}$ and (FIG. 27K) BGM$^{ACT}$ after 7d in the SRC. FIG. 27L shows quantification of TRAP$^{+ve}$ pixels within the total area occupied by the BGMs on post-transplant days 7. Scale Bars=100 µm, ** indicates p<0.01.

DETAILED DESCRIPTION OF THE INVENTION

Figure 1:
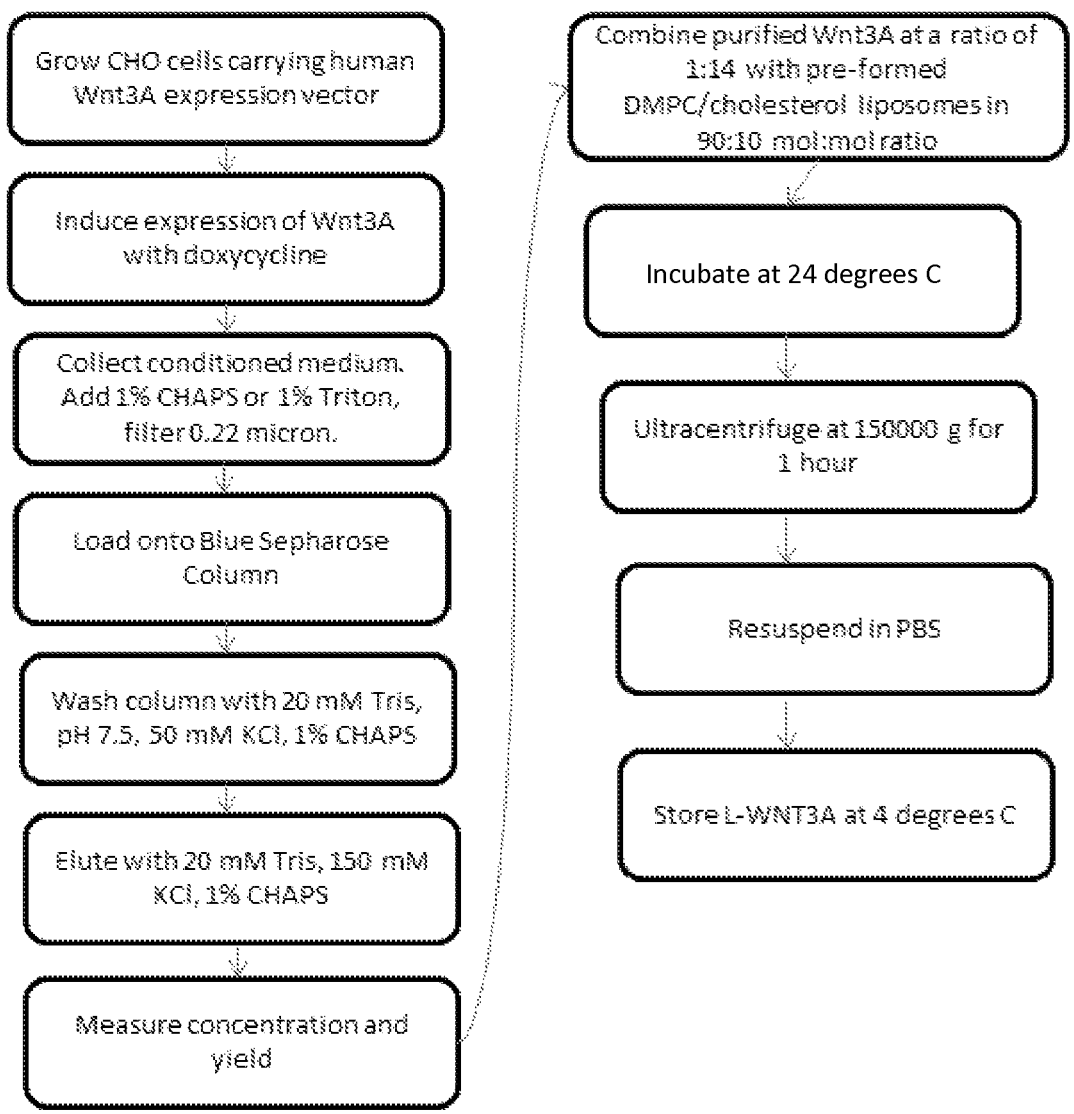
FIG. 1 illustrates a purification scheme of the present invention.

Disclosed herein are compositions, methods, processes, and kits for use in generating a liposomal Wnt polypeptide. Also disclosed herein are compositions, methods, processes, and kits for generating bone graft materials. In some embodiments, a composition comprises a functionally active mammalian Wnt polypeptide and an aqueous solution comprising liposomes, wherein the phospholipids comprising the liposomes have a phase transition temperature from about 10° C. to about 25° C. In some embodiments, a composition comprises a functionally active mammalian Wnt polypeptide and an aqueous solution comprising liposomes, wherein the phospholipids comprising the liposomes have a tail carbon length of between about 12 carbons and about 14 carbons. In some embodiments, a composition also comprises a functionally active Wnt3a polypeptide and an aqueous solution comprising liposomes, wherein the functionally active Wnt3a polypeptide comprises a lipid modification at an amino acid position corresponding to amino acid residue 209 as set forth in SEQ ID NO:1.

In some embodiments, described herein is a method of preparing a liposomal Wnt polypeptide, which comprises the steps of contacting a sample comprising Wnt polypeptides to an aqueous solution of liposomes, wherein the phospholipids comprising the liposomes have a phase transition temperature from about 10° C. to about 25° C. In some embodiments, described herein is a method of preparing a liposomal Wnt polypeptide, which comprises the steps of contacting a sample comprising Wnt polypeptides to an aqueous solution of liposomes, wherein the phospholipids comprising the liposome have a tail carbon length of between about 12 carbons and about 14 carbons. In some embodiments, also described herein is a method of preparing a liposomal Wnt3a polypeptide, which comprises the steps of (a) harvesting Wnt3a polypeptides from a conditioned media comprising Chinese hamster ovary (CHO) cells; (b) introducing the Wnt3a polypeptides to an ion-exchange column immobilized with a sulfonated polyaromatic compound; (c) eluting the Wnt3a polypeptides from the ion-exchange column utilizing a step gradient; and (d) contacting the Wnt3a polypeptides from step (c) with an aqueous solution of liposomes.

In some embodiments, described herein is a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt polypeptide. In some embodiments, also described herein is a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt polypeptide.

In some embodiments, described herein is a mammalian bone marrow composition produced by a process which comprises the step of contacting isolated mammalian bone marrow cells ex-vivo with a liposomal Wnt polypeptide, wherein the contacting time is between about 30 minutes and about 4 hours.

In some embodiments, described herein is a method of treating a bone defect in a subject, which comprises the steps of (a) contacting a sample comprising mammalian bone marrow cells ex-vivo with a liposomal Wnt polypeptide; (b) washing the sample to remove free liposomal Wnt polypeptide; and (c) transplanting the liposomal Wnt polypeptide treated bone graft materials into a site of bone defect. Also described herein is a method of treating a bone defect in a subject, which comprises the steps of (a) contacting a sample comprising mammalian bone marrow cells ex-vivo with a liposomal Wnt3a polypeptide; (b) washing the sample to remove free liposomal Wnt3a polypeptide; and (c) transplanting the liposomal Wnt3a polypeptide treated bone graft materials into a site of bone defect.

In some embodiments, described herein is a method of generating bone graft materials, which comprises the steps of (a) contacting a sample comprising mammalian bone marrow cells ex-vivo with a liposomal Wnt polypeptide; (b) washing the sample to remove free liposomal Wnt polypeptide; and (c) transplanting the liposomal Wnt polypeptide treated bone graft materials into a site of bone defect. Also described herein is a method of generating bone graft materials, which comprises the steps of (a) contacting a sample comprising mammalian bone marrow cells ex-vivo with a liposomal Wnt3a polypeptide; (b) washing the sample to remove free liposomal Wnt3a polypeptide; and (c) transplanting the liposomal Wnt3a polypeptide treated bone graft materials into a site of bone defect.

In some aspects, described herein is a composition which comprises at least about 60%, or at least about 70% or at least about 80%, or at least about 85%, or at least about 90%, or at least about 95% of functionally active Wnt3a polypeptide of SEQ ID NO: 1 lipid modified at Ser209, or at a corresponding conserved Ser of a non-human mammalian Wnt3a polypeptide in the absence of lipid modification at Cys77; or at a corresponding conserved Cys of a non-human mammalian Wnt3a polypeptide. In some embodiments, described herein is a composition which comprises at least about 60%, or at least about 70% or at least about 80%, or at least about 85%, or at least about 90%, or at least about 95% of functionally active human Wnt polypeptide other than Wnt3A, which is lipid modified at a conserved Ser corresponding to Wnt3A ser209 in the absence of lipid modification at a corresponding conserved Cys to Wnt3A Cys77.

In some aspects, the Wnt polypeptide is Wnt3a or a functionally active variant thereof. In other aspects, the Wnt polypeptide is human Wnt3a or a functionally active variant thereof. In yet another aspect, the Wnt polypeptide is Wnt3a of SEQ ID NO: 1 or a functionally active variant thereof. In a further aspect, the lipid modification is palmitoylation. In other aspects, the Wnt polypeptide is a human Wnt protein other than Wnt3A, such as a Wnt1, Wnt2, Wnt2b (or Wnt13), Wnt3, Wnt4, Wnt5a, Wnt5b, Wnt6, Wnt7a, Wnt7b, Wnt8a, Wnt8b, Wnt9a (Wnt14, or Wnt14b), Wnt9b (Wnt14b, or Wnt15), Wnt10a, Wnt10b (or Wnt12), Wnt11, Wnt-16a, Wnt-16b polypeptide or a functionally active variant thereof. In some embodiments, the polypeptide is Wnt5A or Wnt10b or a functionally active variant thereof. In some such embodiments, the Wnt polypeptide is formulated into a liposome, e.g. a liposome comprising DMPC and/or cholesterol.

In another aspect, described herein is a method for the purification of a Wnt polypeptide from mammalian cell culture, including without limitation, recombinant Chinese Hamster Ovary (CHO) cells, which comprises subjecting a culture medium of said cells that contains the Wnt polypeptide to purification utilizing a separation step such as for example on a chromatographic column (e.g. Blue Sepharose ion-exchange column) in the absence of alternative purification steps such as a gel filtration purification step. In some embodiments, the purification is performed also in the absence of a purification step of a heparin sulfate column. In another embodiment, the cells are adherent cells and the culture medium further comprises serum, such as fetal bovine serum (FBS). In further embodiments, purification on columns such as the Blue Sepharose ion-exchange column is performed using a salt gradient of 150 mM to 1.5 M, where the salt can, for example be sodium or potassium chloride. In some instances, the purification scheme is followed by a further purification step such as for example using pre-fabricated liposomes which can comprise lipids such as DPMC and/or cholesterol, for example at a 90:10 mol:mol ratio. In some instances, the use of pre-fabricated liposomes takes advantage of the hydrophobicity of Wnt polypeptides and eliminates the need for further purification steps, such as gel filtration and/or heparin sulfate column purification steps.

When the cells are suspension cells, culturing can be performed under serum-free conditions. In some embodiments, the Wnt polypeptide can be Wnt3a, such as human Wnt3a, e.g. human Wnt3a of SEQ ID NO: 1 or a functionally active variant thereof; or the Wnt polypeptide can be a human Wnt polypeptide other than Wnt3A, e.g. Wnt1, Wnt2, Wnt2b (or Wnt13), Wnt3, Wnt4, Wnt5a, Wnt5b, Wnt6, Wnt7a, Wnt7b, Wnt8a, Wnt8b, Wnt9a (Wnt14, or Wnt14b), Wnt9b (Wnt14b, or Wnt15), Wnt10a, Wnt10b (or Wnt12), Wnt11, Wnt-16a, Wnt-16b polypeptide or a functionally active variant thereof. In some embodiments, the polypeptide is Wnt5A or Wnt10b or a functionally active variant thereof. In a further aspect, the invention concerns a Wnt composition purified by the foregoing method. In one embodiment, the Wnt composition comprises a Wnt polypeptide that is Wnt3a or a functionally active variant thereof. In another embodiment, the Wnt composition comprises a Wnt polypeptide that is human Wnt3a or a functionally active variant thereof. In yet another embodiment, the Wnt composition comprises a Wnt polypeptide that is human Wnt3a of SEQ ID NO: 1 or a functionally active variant thereof.

In some aspects, described herein also includes kits for generating bone graft materials which comprise the liposomal Wnt polypeptide, the liposomal Wnt3a polypeptide, or the isolated enhanced mammalian bone marrow cell compositions.

A. Definitions

Before the present methods are described, it is to be understood that this invention is not limited to particular methods described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges can independently be included in the smaller ranges encompassed within the invention, subject to any specifically excluded limit in the stated range. Also used herein, ranges and amounts can be expressed as "about" a particular value or range. About also includes the exact amount. Hence "about 5 µL" means "about 5 µL" and also "5 µL." Generally, the term "about" includes an amount that would be expected to be within ±10% of the amount.

Unless defined otherwise, technical and scientific terms used herein have the same meaning as commonly understood by one of ordinary skill in the art to which this invention belongs. Singleton et al, *Dictionary of Microbiology and Molecular Biology* 2nd ed., J. Wiley & Sons (New York, N.Y. 1994), provides one skilled in the art with a general guide to many of the terms used in the present application.

Wnt polypeptides form a family of highly conserved secreted signaling molecules that regulate cell-to-cell interactions during embryogenesis. The terms "Wnts" or "Wnt gene product" or "Wnt polypeptide" when used herein encompasses native sequence Wnt polypeptides, Wnt polypeptide fragments, chimeric Wnt polypeptides or functionally active variants of the foregoing. The terms "WNT" and "Wnt" are used interchangeably herein. Similarly, the terms "WNT3A", "WNT3a", "Wnt3A", or "Wnt3a" are used interchangeably herein.

A "native sequence" polypeptide is one that has the same amino acid sequence as a Wnt polypeptide derived from nature. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, or the like. In some instances, the "native sequence" polypeptide also includes the N-terminal methionine. In some instances, it does not include the N-terminal methionine.

The term "native sequence Wnt polypeptide" includes, without limitation, mammalian Wnt polypeptides, such as human or murine Wnt polypeptides. Human Wnt polypeptides include Wnt1, Wnt2, Wnt2b (or Wnt13), Wnt3, Wnt3a, Wnt4, Wnt5a, Wnt5b, Wnt6, Wnt7a, Wnt7b, Wnt8a, Wnt8b, Wnt9a (Wnt14, or Wnt14b), Wnt9b (Wnt14b, or Wnt15), Wnt10a, Wnt10b (or Wnt12), Wnt11, Wnt-16a, or Wnt-16b polypeptide. Wnt1 can be referred by the Genbank references NP005421.1 and AAH74799.1. Wnt2 can be referred by the Genbank references NP003382.1 and AAH78170.1 In general, Wnt2 can be expressed in the brain, thalamus, in both fetal and adult lungs, or in the placenta. Wnt2B has two isoforms and their Genbank reference Nos. are NP004176.2 and NP078613.1, respectively. Isoform 1 can be expressed in adult heart, brain, placenta, lung, prostate, testis, ovary, small intestine and/or colon. In the adult brain, it is mainly found in the caudate nucleus, subthalamic nucleus and thalamus. In some instances, it is also detected in fetal brain, lung and kidney. Isoform 2 can be expressed in fetal brain, fetal lung, fetal kidney, caudate nucleus, testis and/or cancer cell lines.

Wnt3 and Wnt3a play distinct roles in cell-cell signaling during morphogenesis of the developing neural tube. Wnt3 has the Genbank reference AB060284.1 (see also GenBank Nos. BAB61052.1 and AA103924.1. Wnt3a has the amino acid sequence as set forth in SEQ ID NO:1 and the nucleic acid sequence as set forth in SEQ ID NO:2. The native human Wnt3a amino acid and nucleotide sequences are also disclosed in Genbank reference NM_033131, and the protein sequence at Genbank reference NP_149122. The Wnt3a protein precursor has the Genbank reference NP_149122.1. The native Wnt3a is 352 amino acid residues in length. It contains a signal peptide which is from amino acid residues 1-18. The mature protein contains the amino acid residues 19-352. Reference to, for example, Cys77 or Ser209 of Wnt3A, as used herein, is made relative to the full-length sequence, as shown in SEQ ID NO:1. In some instances, the term "native human Wnt3a" polypeptide refers to the native human Wnt3a polypeptide of SEQ ID NO:1, with or without its N-terminal methionine (Met), and with or without the native signal sequence.

Wnt4 has the Genbank references NP110388.2 and BAC23080.1. Wnt 5a has the Genbank references NP003383.1, and NP003383.2.Wnt5b has the Genbank references BAB62039.1 and AAG38659. Wnt 6 has the Genbank references NP006513.1 and BAB55603.1. Wnt 7a has the Genbank references NP004616.2 and BAA82509.1. It can be expressed in the placenta, kidney, testis, uterus, fetal lung, fetal brain, or adult brain. Wnt 7b has the Genbank references NP4 78679.1 and BAB68399.1. It can be expressed in fetal brain, lung and/or kidney, or in adult brain, lung and/or prostate. Wnt 8A has at least two alternative transcripts, Genbank references NP 114139.1 and NP490645.1. Wnt 8B can be expressed in the forebrain. It has the Genbank reference NP003384.1. Wnt 10A has the Genbank references AAG45153 and NP079492.2. Wnt 10B is detected in most adult tissues, with highest levels in the heart and skeletal muscles. It has the Genbank reference NP003385.2. Wnt 11 can be expressed in fetal lung, kidney, adult heart, liver, skeletal muscle, and pancreas. It has the Genbank reference NP004617.2. Wnt 14 has the Genbank reference NP003386.1. Wnt 15 can be expressed in fetal kidney or adult kidney. It can also be expressed in the brain. It has the Genbank reference NP003387.1. Wnt 16 has two isoforms, Wnt-16a and Wnt-16b, produced by alternative splicing. Isoform Wnt-16a can be expressed in the pancreas. Isoform Wnt-16b can be expressed in peripheral lymphoid organs such as spleen, appendix, and lymph nodes, or in the kidney. However, it cannot be expressed in bone marrow. The Genbank references are NP476509.1 and NP057171.2, respectively, for Wnt16a and Wnt16b. All GenBank, SwissProt and other database sequences listed are expressly incorporated by reference herein.

A "variant" polypeptide means a functionally active polypeptide as defined below having less than 100% sequence identity with a native sequence polypeptide. Such variants include polypeptides longer or shorter polypeptides, for example wherein one or more amino acid residues are added at the N- or C terminus of, or within, the native sequence; from about one to 300 amino acid residues are deleted. Variant polypeptides include polypeptides with one or more amino acid substitutions in comparison to the native polypeptide sequence, or derivatives of a polypeptide sequence, wherein an amino acid residue has been covalently modified so that the resulting product has a non-naturally occurring amino acid.

A "functionally active" Wnt polypeptide (e.g. Wnt3a polypeptide) retains the effector functions that are directly or indirectly caused or performed by native sequence Wnt polypeptides. Effector functions of native sequence Wnt polypeptides include stabilization of β-catenin, stimulation of stem cell self-renewal, C57MG transformation and induction of target genes in Xenopus animal cap assays, as well as target gene expression in human teratocarcinoma cells. The purified Wnt compositions find use in a variety of therapeutic methods, including the maintenance and growth of stem cells, tissue regeneration, and the like.

In some instances, a functionally active Wnt variant will have an amino acid sequence that has at least about 30%, at least about 40%, at least about 50%, at least about 60%, at least about 70%, at least about 80%, at least about 90%, at least about 95%, or at least about 99% amino acid sequence identity with a native sequence Wnt polypeptide. In one embodiment the native sequence Wnt polypeptide is a mammalian (e.g., human) Wnt polypeptide such as Wnt3a.

The term "amino acid" refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |

-continued

| Amino Acid | 3-Letter Code | 1-Letter Code | Side-chain Polarity | Side-chain charge (pH 7.4) | Hydropathy Index |
|---|---|---|---|---|---|
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" are glycine, alanine, proline, and analogs thereof "Large hydrophobic amino acids" are valine, leucine, isoleucine, phenylalanine, methionine, tryptophan, and analogs thereof. "Polar amino acids" are serine, threonine, asparagine, glutamine, cysteine, tyrosine, and analogs thereof "Charged amino acids" are lysine, arginine, histidine, aspartate, glutamate, and analogs thereof.

The term "amino acid analog" refers to a molecule which is structurally similar to an amino acid and which can be substituted for an amino acid in the formation of a peptidomimetic macrocycle Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids or amino acid analogs include, without limitation, structures according to the following:

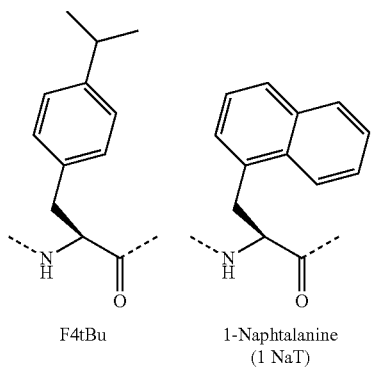

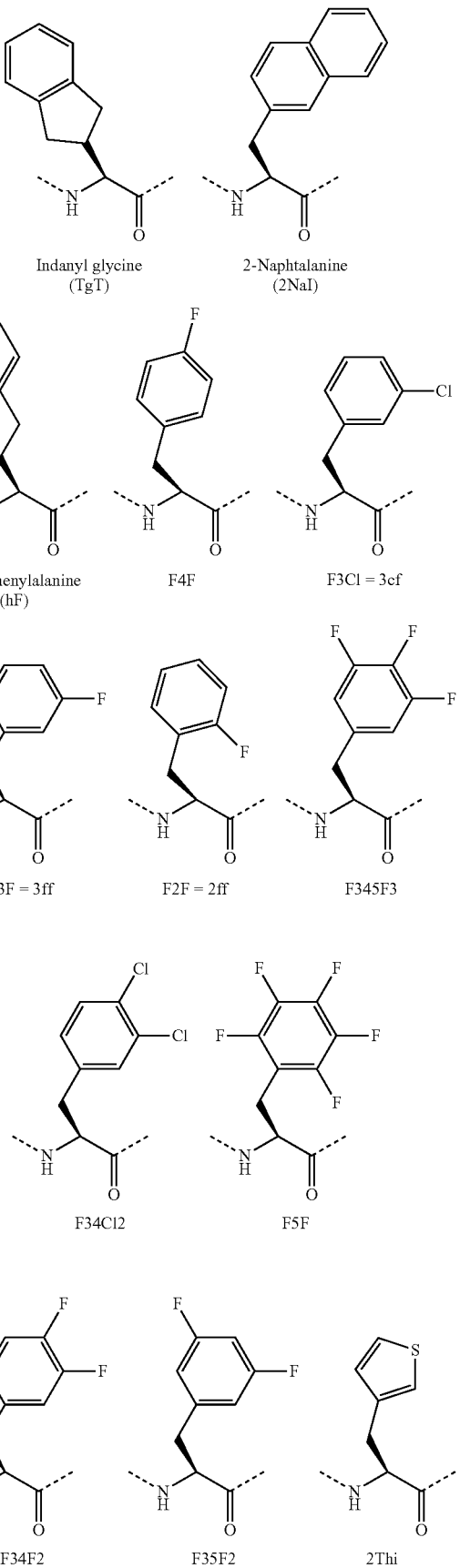

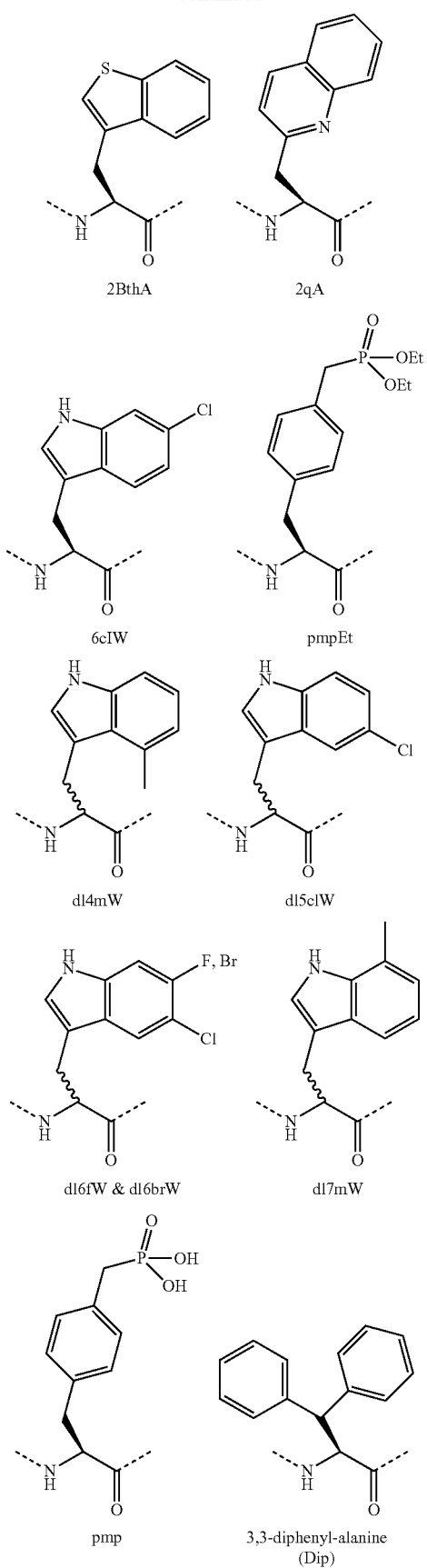
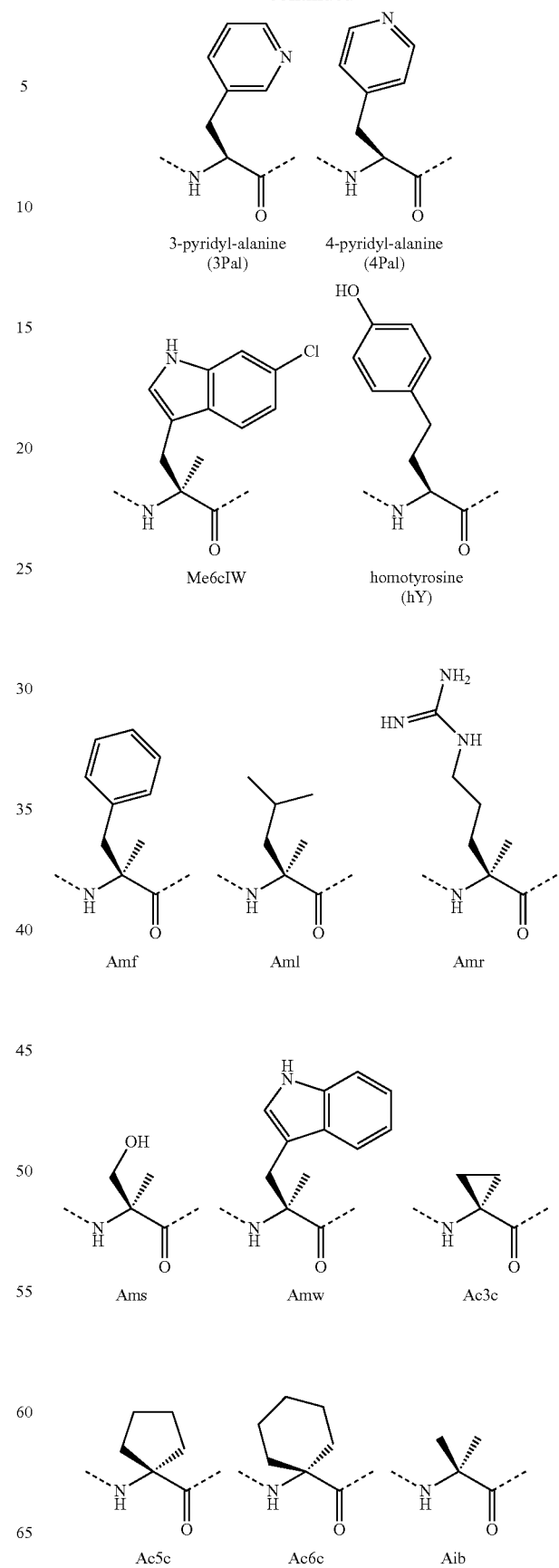

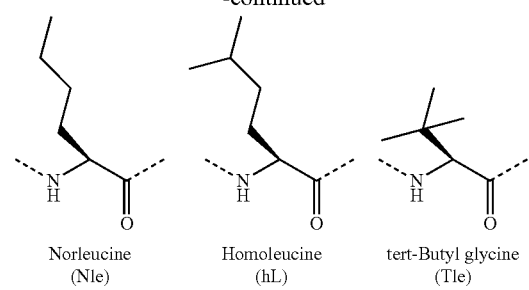
Norleucine (Nle)    Homoleucine (hL)    tert-Butyl glycine (Tle)
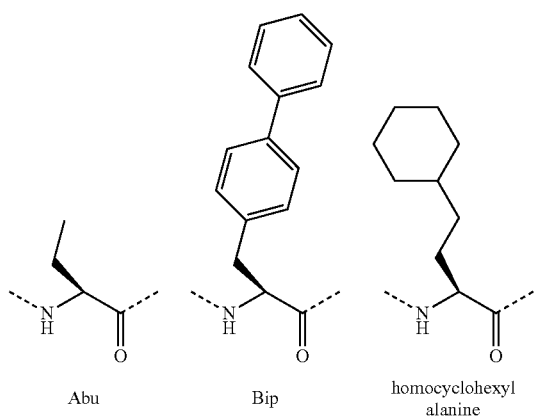
Abu    Bip    homocyclohexyl alanine (hCha)
cyclohexyl alanine (Cha)    cyclohexyl glycine (Chg)    cyclohexyl glycine (Chg)
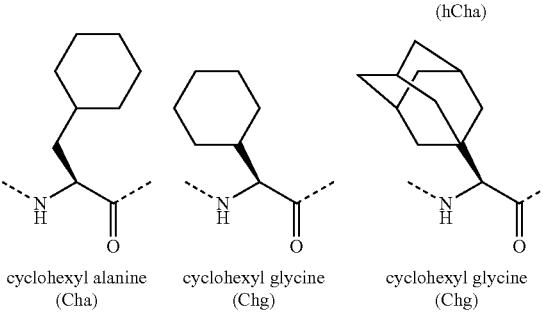
cyclobutyl alanine (Cba)    cyclopentyl alanine (Cpg)    NmF
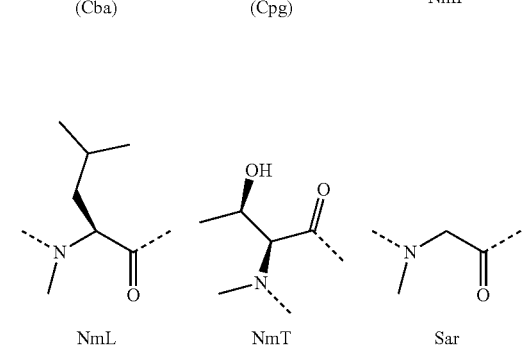
NmL    NmT    Sar
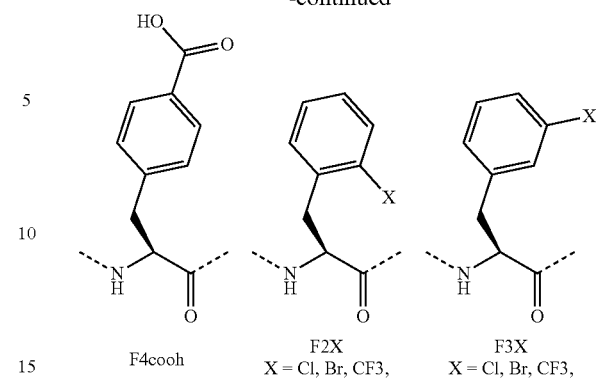
F4cooh    F2X
X = Cl, Br, CF3, CN, Me, NO2    F3X
X = Cl, Br, CF3, CN, Me, NO2
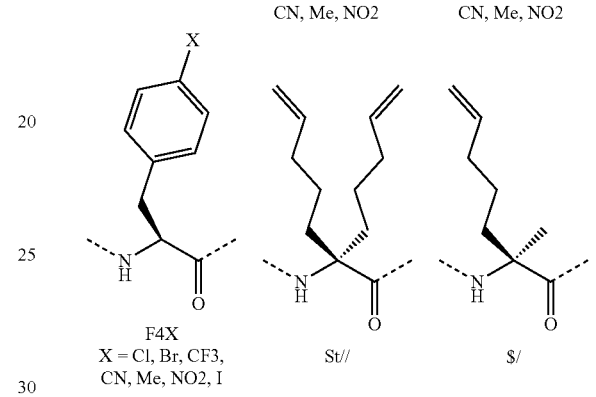
F4X
X = Cl, Br, CF3, CN, Me, NO2, I    S5    S5
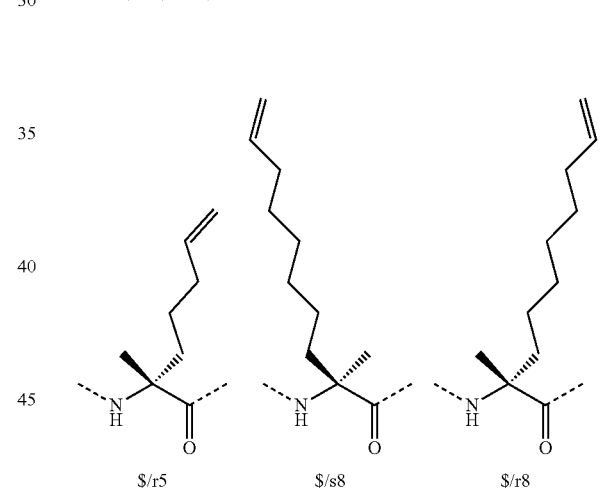
S/r5    S/s8    S/r8
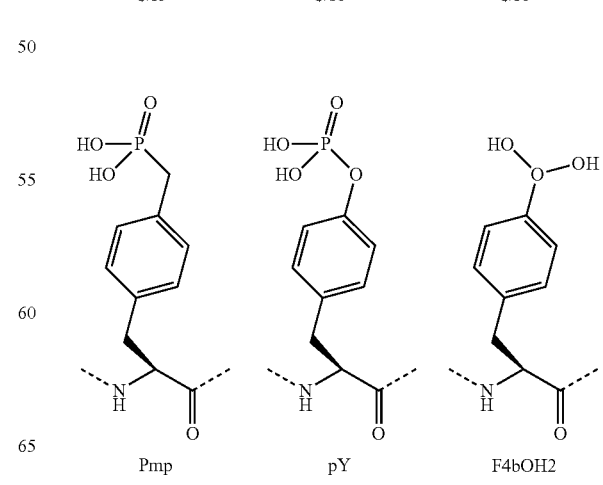
Pmp    pY    F4bOH2

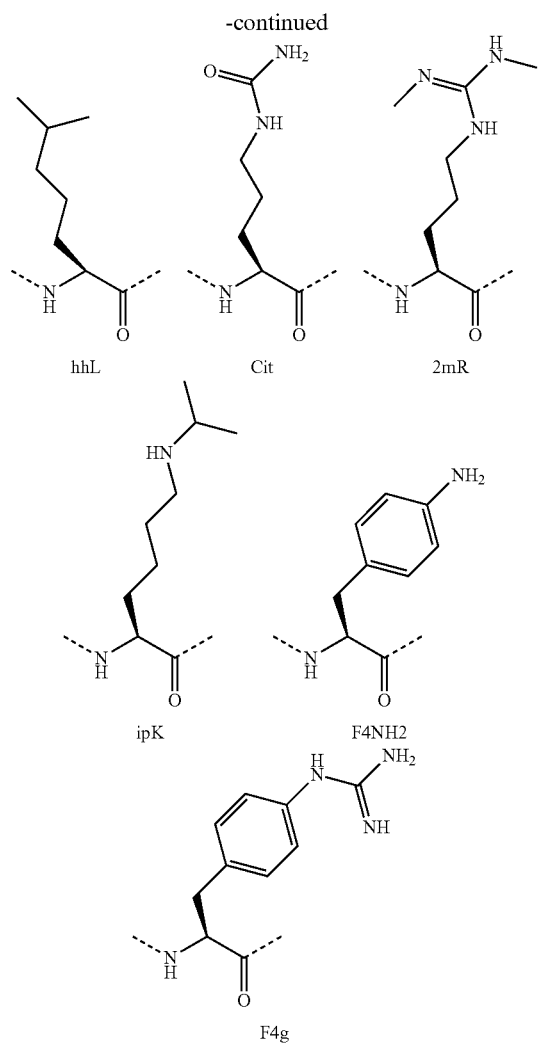

Amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine.dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)2-OH (symmetrical); Lys(ivDde)-OH; Lys(Me)2-OH.HCl; Lys(Me3)-OH chloride; Nω-nitro-D-arginine; and Nω-nitro-L-arginine.

Amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichlorophenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-nor-harman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, amino acid analogs are racemic. In some embodiments, the D isomer of the amino acid analog is used. In some embodiments, the L isomer of the amino acid analog is used. In other embodiments, the amino acid analog comprises chiral centers that are in the R or S configuration. In still other embodiments, the amino group(s) of a β-amino acid analog is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analog is protected, e.g., as its ester derivative. In some embodiments the salt of the amino acid analog is used.

A "non-essential" amino acid residue is a residue that can be altered from the wild-type sequence of a polypeptide without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions are substitutions based on isosteric considerations (e.g. norleucine for methionine) or other properties (e.g. 2-thienylalanine for phenylalanine, or 6-Cl-tryptophan for tryptophan).

B. Detailed Description

The molecular cloning and characterization of Wnt3a was described by Saitoh et al., Biochem Biophys Res Commun, 2001, 29; 284(5):1168-75. Native human Wnt3a is a lipid modified growth factor, composed of 352 amino acids (SEQ ID NO:1), that is effective in activating stem cells or stimulating their self-renewal. In some cases, due to its hydrophobic nature the active Wnt3a polypeptide or other Wnt polypeptides are difficult to purify to homogeneity at scaleable levels. In one aspect, described herein is a method for purification of Wnt polypeptides. In some instances, the purification method improves the purity and yield of human Wnt polypeptides. In some embodiments, the purified Wnt polypeptide is used as part of a therapeutic regimen. In some embodiments, the purified Wnt polypeptide is used as a therapeutic polypeptide.

As described elsewhere herein, Wnt polypeptides form a family of highly conserved secreted signaling molecules. Wnt polypeptides can be mammalian, such as a human Wnt polypeptide. In some embodiments, Wnt polypeptides include Wnt1, Wnt2, Wnt2b (or Wnt13), Wnt3, Wnt3a, Wnt4, Wnt5a, Wnt5b, Wnt6, Wnt7a, Wnt7b, Wnt8a, Wnt8b, Wnt9a (Wnt14, or Wnt14b), Wnt9b (Wnt14b, or Wnt15), Wnt10a, Wnt10b (or Wnt12), Wnt11, Wnt-16a, or a Wnt-16b polypeptide sequences or a functionally active variants thereof. In some embodiments, a Wnt polypeptide is selected from the group consisting of a Wnt3a polypeptide, Wnt5a polypeptide, Wnt10b polypeptide and a functionally active Wnt variants thereof In some embodiments, the Wnt polypeptide is a Wnt3a polypeptide or a functionally active variant thereof. In some embodiments, the Wnt polypeptide is a Wnt5a polypeptide or a functionally active variant thereof. In some embodiments, the Wnt polypeptide is a Wnt10b polypeptide or a functionally active variant thereof. In some embodiments, the Wnt3a polypeptide is a human Wnt3a polypeptide or a functionally active variant thereof. In some instances, the sequence identity of a functionally active variant Wnt3a polypeptide is at least about 30%, about 40%, about 50%, about 60%, about 70%, about 80%, about 90%, about 95%, or about 99% identical to a native Wnt3a polypeptide sequence, such as a human Wnt3a polypeptide sequence (e.g., SEQ ID NO:1). In some instances, the sequence identity of a functionally active variant Wnt3a polypeptide is at most about 30%, about 40%, about 50%, about 60%, about 70%, about 80%, about 90%, about 95%, or about 100% identical to a native Wnt3a polypeptide sequence, such as a human Wnt3a polypeptide sequence (e.g., SEQ ID NO:1). In some instances, the amino acid sequence of the Wnt3a polypeptide is as set forth in SEQ ID NO:1, or the Wnt3a polypeptide is encoded by the nucleic acid sequence of SEQ ID NO:2.

In some instances, the purification scheme described herein is simple, and inexpensive. In some cases, the purification scheme described herein enables purification of an functionally active form of Wnt polypeptide with higher purity. In some embodiments, the purification methods described herein enable purification of Wnt polypeptides from culture media of recombinant host cells. In some instances, the recombinant host cell or the expression cell line is a prokaryotic host cell or expression cell line, a yeast host cell or expression cell line, an insect host cell or expression cell line, or a mammalian host cell or expression cell line.

In some embodiments, the recombinant host cell or expression cell line is a yeast host cell or expression cell line. Exemplary yeast host cells include, but are not limited to,

*Pichia pastoris* yeast strains such as GS115, KM71H, SMD1168, SMD1168H, and X-33; and *Saccharomyces cerevisiae* yeast strain such as INVSc1.

In some embodiments, the recombinant host cell or expression cell line is an insect host cell or expression cell line. Exemplary insect cell lines include, but are not limited to, *Drosophila* S2 cells, Sf9 cells, Sf21 cells, High Five™ cells, and expresSF+® cells.

In some embodiments, the recombinant host cell or expression cell line is a mammalian host cell or expression cell line. In some cases, mammalian cell lines is a stable cell lines, or a cell line that has incorporated a genetic material of interest into its own genome and has the capability to express the products of the genetic material after many generations of cell division. In some embodiments, the mammalian cell line is a Current Good Manufacturing Practices (cGMP) compliant cell line. Exemplary mammalian cell lines include, but are not limited to, 293A cell line, 293FT cell line, 293F cells, 293 H cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line. In some embodiments, the mammalian cell line is a CHO cell line. In some embodiments, the mammalian cell line is a CHO-S cell line. As used herein, "CHO cells" or "CHO cell line" is a generic term that encompasses the different types of CHO cells and CHO cell lines.

In some embodiments, the mammalian host cells are grown as a liquid suspension culture, in soft agar, on top of soft agar, or as monolayer. In some embodiments, the CHO cells are grown as a liquid suspension culture, in soft agar, on top of soft agar, or as monolayer. In some embodiments, the CHO cells are cultured in liquid suspension culture. In some cases, the culture medium contains a serum. Non-limiting examples of serum include fetal bovine serum (FBS), HyClone FetalClone II and III, iron-supplemented bovine calf serum (ICS), and human platelet lysates. In some embodiments, the serum is FBS. In some embodiments, the FBS presents in the medium is at most about 0.1%, 0.5%, 1%, 2%, 3%, 4%, 5%, 6%, 7%, 8%, 9%, 10%, 11%, 12%, 13%, 14%, 15%, or less. In some embodiments, the FBS presents in the medium is at least about 0.1%, 0.5%, 1%, 2%, 3%, 4%, 5%, 6%, 7%, 8%, 9%, 10%, 11%, 12%, 13%, 14%, 15%, or more.

In some embodiments, the serum (e.g. FBS) is needed for the induction of expression and for secretion of Wnt polypeptides (e.g. Wnt3a polypeptide) into the culture medium. In some embodiments, the serum provides one or more essential factors that are used for lipid modification on a Wnt polypeptide (e.g. residues such as Ser 209 in Wnt3a). In some embodiments, the serum provides one or more chaperone proteins and lipophilic molecules that are used for the transportation of Wnt polypeptide (e.g. Wnt3a) from the endoplasmic reticulum (ER) to the Golgi and then to the cell membrane.

In some embodiments, the serum is modified to remove the lipid components. In some instances, a defined set of lipids is then introduced into the modified serum. In some cases, a stripping agent, such as charcoal, is used to remove non-polar lipophilic materials (e.g. viruses, growth factors, and hormones) from the serum. In some instances, a lipid supplement is introduced into the modified serum. Non-limiting examples of lipid supplement include Lipid Mixture 1 (Sigma-Aldrich), Lipid Mixture 2 (Sigma-Aldrich), Lipogro® (Rocky Mountain Biologicals), and Chemically Defined Lipid Concentration (Life Technologies).

In some embodiments, the mammalian host cells (e.g. CHO or CHO-S cells) are cultured in a serum-free medium. Non-limiting examples of serum-free media include CD CHO medium, CD CHO AGT™ medium, CD OptiCHO™ medium, CHO-S-SFM II (optionally including hypoxanthine and thymidine), CD 293 AGT™ medium, Adenovirus Expression Medium (AEM), FreeStyle™ 293 Expression medium, EX-CELL® 302 Serum-Free medium, EX-CELL® 325 PF CHO Serum-Free medium, EX-CELL® CD CHO-2 medium animal-component free, EX-CELL® CD CHO-3 medium, and EX-CELL® CDHO DHFR⁻ medium animal-component free.

In some embodiments, the serum-free medium contains one or more additional supplement. In some embodiments, the additional supplement is a serum. In some cases, the serum is FBS. In some cases, the FBS presents in the serum-free medium is at most about 0.1%, 0.5%, 1%, 2%, 3%, 4%, 5%, 6%, 7%, 8%, 9%, 10%, 11%, 12%, 13%, 14%, 15%, or less. In some cases, the FBS presents in the serum-free medium is at least about 0.1%, 0.5%, 1%, 2%, 3%, 4%, 5%, 6%, 7%, 8%, 9%, 10%, 11%, 12%, 13%, 14%, 15%, or more.

In some embodiments, the additional supplement is a lipid supplement. Non-limiting examples of lipid supplement include Lipid Mixture 1 (Sigma-Aldrich), Lipid Mixture 2 (Sigma-Aldrich), Lipogro® (Rocky Mountain Biologicals), and Chemically Defined Lipid Concentration (Life Technologies). In some embodiments, the serum-free medium contains a lipid supplement.

In some embodiments, the additional supplement is a serum substitute. In some embodiments, the serum substitute is selected from EXCYTE (Millipore), EX-CYTE+ human serum albumin+AOF ITS (Insulin, transferrin, and selenium, Millipore), Human serum albumin (Millipore), Heparin sulfate (Sigma), lipids such as described elsewhere herein and not limiting to DMPC and cholesterol, Cell-ess (Essential Pharmaceuticals), and the like. In some instances, the Wnt polypeptide in the presence of a serum substitute is secreted into the conditioned medium. In some instances, the Wnt polypeptide in the presence of a serum substitute is not secreted into the conditioned medium. In some instances, the Wnt3a polypeptide in the presence of a serum substitute is secreted into the conditioned medium. In some instances, the Wnt3a polypeptide in the presence of a serum substitute is not secreted into the conditioned medium.

In some embodiments, an expression vector that is tolerant of a serum-free medium condition is used. In some cases, the expression vector leads to a high copy number of the desired transcript and secretion of the polypeptide of interest. In some instances, the expression vector is compatible with cGMP compatible mammalian cell lines. Non-limiting examples of mammalian expression vectors include pOptivec vector, pTargeT™ vector, BacMam pCMV-Dest vector, Flp-In™ core system, Gateway® suite of vectors, HaloTag® vector, Flexi® vector, pCMVTNT™ vector, and pcDNA™4/TO vector. In some embodiments, the expression vector is selected from pOptivec and pTargeT™ vectors. The pOptivec vector is a TOPO® adapted bicistronic plasmid which allows rapid cloning of a gene containing a mammalian secretion signal and the gene of interest downstream of the CMV promoter. The dihydrofolate reductase selection markers allows for rapid selection. In some cases, this vector is used for transient transfection of CHO-S cells.

In some instances, the pTargeT™ vector is used for transient transfection of CHO-S cells and for creating a stable cell line expressing a Wnt polypeptide (e.g. Wnt3a).

In some embodiments, acidification of the culture condition is used to aid in Wnt secretion. In some instances, acidification of the culture condition is used to aid in Wnt3a secretion. In some instances, acidification mimics vesicular acidification. In some instances, acidification is an acidification of the cytoplasm. In some instances, acidification occurs naturally such as acids secreted by the cells growing in the conditioned media, or artificially such as the addition of acids such as for example acetic acid. In some instances, acidification aids in secretion of Wnt polypeptide. In some instances, acidification aids in secretion of Wnt3a polypeptide.

In some embodiments, the expression method of a Wnt polypeptide in yeast cells, insect cells, or mammalian cells follows protocols well known in the art. In some instances, the Wnt polypeptide is expressed in mammalian cells. In some embodiments, a transcriptional induction agent is used to induce expression of the Wnt polypeptide. In some cases, the transcriptional induction agent includes doxycycline, tetracycline, and coumermycin. In some cases, the expression is constitutive, or that the polypeptide is expressed without an induction agent. In some embodiments, the Wnt polypeptide is secreted into the medium. In some instances, the conditioned medium is harvested and an additional agent is added to solubilize the Wnt polypeptide. In some instances, the additional agent is a detergent. In some instances, the detergent is a nonionic detergent, an anionic detergent, or a zwitterionic detergent. Exemplary detergents include, but are not limited to, Brij-35, Brij-58, 3-[(3-Cholamidopropyl)dimethylammonio]-1-propanesulfonate (CHAPS), 3-([3-Cholamidopropyl]dimethylammonio)-2-hydroxy-1-propanesulfonate (CHAPSO), nonyl phenoxypolethoxylethanol (NP-40), Octyl glucoside, Octyl thioglucoside, sodium dodecyl sulfate (SDS), Triton X-100, Triton X-114, Tween 20, and Tween 80. In some embodiments, the detergent is CHAPS or Triton X-100. In some embodiments, the detergent is CHAPS. CHAPS is a zwitterionic detergent useful for membrane protein solubilization. In some embodiments, the Wnt polypeptide is also post-translationally modified by glycosylation and palmitoylation.

Palmitoylation is covalent attachment of fatty acids, such as palmitic acid, to cysteine, serin, and threonine residues. In some instances, palmitoylation enhances the hydrophobicity of proteins and contribute to their membrane association. For example, Nusse et al. reported that the murine Wnt3a protein was S-palmitoylated at a conserved cysteine residue (C77) (Willert et al., *Nature*, 2003, 423:448-452) and that a mutant form of mouse Wnt3a protein, wherein the palmitoylated Cys77 was substituted with alanine (C77A), showed a diminished ability to activate Wnt signaling, but was secreted normally into the culture medium. Further, the study showed that palmitoylation of the Cys77 residue was important for biological activity.

In some embodiments, the Wnt polypeptide is palmitoylated at a cysteine, serine, and/or threonine residue. In some embodiments, the Wnt3a polypeptide is palmitoylated at a cysteine, serine, and/or threonine residue. In some instances, the Wnt3a polypeptide is palmitoylated at C77, S139, S181, S209, or S211, as set forth in SEQ ID NO:1. In some instances, the Wnt3a polypeptide is palmitoylated at one or more of the amino acid positions selected from C77, S139, S181, S209, or S211, as set forth in SEQ ID NO:1. In some cases, the Wnt3a polypeptide is palmitoylated at C77, as set forth in SEQ ID NO:1. In some cases, the Wnt3a polypeptide is palmitoylated at S209, as set forth in SEQ ID NO:1. In some cases, the Wnt3a polypeptide is palmitoylated at C77 and at S209, as set forth in SEQ ID NO:1. In some cases, the Wnt3a protein is not palmitoylated at C77, as set forth in SEQ ID NO:1. In some cases, the Wnt3a protein is palmitoylated at S209 and is not palmitoylated at C77, as set forth in SEQ ID NO:1.

In some embodiments, the Wnt polypeptide comprising palmitoylated residues are functionally active variant polypeptides, such as a functionally active variant of a Wnt3a native polypeptide (e.g., human Wnt3a). In some embodiments, the Wnt3a functionally active variant polypeptide comprises palmitoylated residues selected from C77, S139, S181, S209, and S211, as set forth in SEQ ID NO:1. In some embodiments, the Wnt3a functionally active variant polypeptide has a palmitoylated residue at S139 as set forth in SEQ ID NO:1. In some embodiments, the functionally active variant Wnt3a polypeptide has a palmitoylated residue at S181 as set forth in SEQ ID NO:1. In some embodiments, the functionally active variant Wnt3a polypeptide has a palmitoylated residue at S209 as set forth in SEQ ID NO:1 In some embodiments, the functionally active variant Wnt3a polypeptide has a palmitoylated residue at S211 as set forth in SEQ ID NO:1. In some embodiments, the functionally active variant Wnt3a polypeptide has a palmitoylated residue at S209 and one other residue as set forth in SEQ ID NO:1. In some embodiments, the one other residue does not include C77. In some embodiments, the functionally active variant Wnt3a polypeptide is palmitoylated at S209 and is not palmitoylated at C77, as set forth in SEQ ID NO:1.

In some embodiments, the purification scheme described herein pertains to a Wnt polypeptide selected from Wnt1, Wnt2, Wnt2b (or Wnt13), Wnt3, Wnt3a, Wnt4, Wnt5a, Wnt5b, Wnt6, Wnt7a, Wnt7b, Wnt8a, Wnt8b, Wnt9a (Wnt14, or Wnt14b), Wnt9b (Wnt14b, or Wnt15), Wnt10a, Wnt10b (or Wnt12), Wnt11, Wnt-16a, and Wnt-16b polypeptide. In some instances, the purification scheme described herein pertains to Wnt3a polypeptide, a Wnt5a polypeptide, or a Wnt10b polypeptide. In some cases, the purification scheme described herein pertains to a Wnt3a polypeptide. In some cases, the purification scheme described herein pertains to a Wnt5a polypeptide. In some cases, the purification scheme described herein pertains to a Wnt10b polypeptide.

In some embodiments, the purification scheme described herein pertains to a Wnt3a polypeptide that has palmitoylation at a cysteine residue that correspond to the cysteine at amino acid position 77 as set forth in SEQ ID NO:1 or a serine residue that correspond to the serine at amino acid position 209 as set forth in SEQ ID NO:1. In some embodiments, the purification scheme described herein selects a Wnt3a polypeptide that has palmitoylation at the cysteine residue that correspond to the cysteine at amino acid position 77 as set forth in SEQ ID NO:1. In some embodiments, the purification scheme described herein selects a Wnt3a polypeptide that has palmitoylation at the serine residue that correspond to the serine at amino acid position 209 as set forth in SEQ ID NO:1. In some embodiments, the purification scheme described herein selects a Wnt3a polypeptide that has palmitoylation at the serine residue that correspond to the serine at amino acid position 209 as set forth in SEQ ID NO:1 and at least one other palmitoylated residue. In some embodiments, the at least one other palmitoylated residue is not C77 as set forth in SEQ ID NO:1. In some embodiments, the purification scheme described herein does not select a Wnt3a polypeptide that has palmitoylation at the cysteine residue that correspond to the cysteine at amino acid position 77 as set forth in SEQ ID NO:1.

In some embodiments, the purification scheme described herein utilizes a separation step. In some embodiments, the separation step is an ion-exchange purification step, a hydrophobic purification step, or an affinity purification step. In some cases, the separation step is an ion-exchange purification step. In some instances, the ion-exchange purification step utilizes beads immobilized with one or more sulfonated polyaromatic compounds. In some instances, the ion-exchange purification step utilizes a column immobilized with one or more sulfonated polyaromatic compounds. A non-limiting example of a sulfonated polyaromatic compound is Cibacron blue F3GA. In some instances, Cibacron blue F3GA is a triazinyl dye. In some instances, beads and/or columns immobilized with a triazinyl dye is used during the ion-exchange purification step. A non-limiting example of a chromatographic column immobilized with Cibacron blue F3GA is a Blue Sepharose column.

In some embodiments, purification is carried out in batch mode with the use of beads immobilized with a sulfonated polyaromatic compound. In general, the Wnt polypeptide is bound to the sulfonated polyaromatic compound immobilized beads in a binding buffer containing a low concentration of salt. High salt destabilizes the non-covalent ionic interactions between protein and the beads, thereby allow elution of the Wnt polypeptide. In some embodiments, the concentration of the salt used in the binding buffer is at most 0, 0.01, 5, 10, 15, 20, 25, 30, 40, 50 mM, or less. In some embodiments, the concentration of the salt used in the binding buffer is at least 0, 0.01, 5, 10, 15, 20, 25, 30, 40, 50 mM, or more. In some embodiments, one or more wash buffers are used to remove unbound impurities. In some embodiments, at most 1, 2, 3, 4, 5, or more wash steps are used. In some embodiments, at least 1, 2, 3, 4, 5 or less wash steps are used. In some embodiments, the concentration of the salt used in the wash buffer is at least 30, 40, 50, 60, 70, 80, 90, 100 mM, more. In some embodiments, the concentration of the salt used in the wash buffer is at most 30, 40, 50, 60, 70, 80, 90, 100 mM, less. In some embodiments, one or more elution steps follow. In some embodiments, the concentration of the salt in the elution buffer is at least 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1500, 2000 mM, or more. In some embodiments, the concentration of the salt in the elution buffer is at most 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1500, 2000 mM, or less. Exemplary salt include sodium chloride, potassium chloride, magnesium chloride, calcium chloride, calcium phosphate, potassium phosphate, magnesium phosphate, sodium phosphate, ammonium sulfate, ammonium chloride, ammonium phosphate, and the like. In some embodiments, a detergent is also formulated into the binding buffer, wash buffer, and/or elution buffer. In some embodiments, the detergent is CHAPS or Triton X-100. In some embodiments, the percentage of CHAPS or Triton X-100 is at least 0.01%, 0.1%, 0.5%, 1%, 1.5%, 2%, 2.5%, 3%, 3.5%, 4%, 4.5%, 5%, or more. In some embodiments, the percentage of CHAPS or Triton X-100 is at most 0.01%, 0.1%, 0.5%, 1%, 1.5%, 2%, 2.5%, 3%, 3.5%, 4%, 4.5%, 5%, or less. In some instances, buffer components such as tris(hydroxymethyl)methylamine HCl (Tris-HCl), 3-{[tris(hydroxymethyl)methyl]amino}propanesulfonic acid (TAPS), N,N-bis(2-hydroxyethyl)glycine (Bicine), N-tris(hydroxymethyl)methylglycine (Tricine), 3-[N-Tris(hydroxymethyl)methylamino]-2-hydroxypropanesulfonic acid (TAPSO), 4-2-hydroxyethyl-1-piperazineethanesulfonic acid (HEPES), 3-(N-morpholino)propanesulfonic acid (MOPS), piperazine-N,N'-bis(2-ethanesulfonic acid) (PIPES), 2-(N-morpholino)ethanesulfonic acid (MES), and the like, are used. In some instances, the pH of the buffer is at least 4, 4.5, 5, 5.5, 6, 6.5, 7, 7.5, 8, 8.5, 9, or more. In some instances, the pH of the buffer is at most 4, 4.5, 5, 5.5, 6, 6.5, 7, 7.5, 8, 8.5, 9, or less. In some embodiments, the Wnt polypeptide is Wnt3a polypeptide, Wnt5a polypeptide, or Wnt10b polypeptide. In some embodiments, the Wnt polypeptide is Wnt3a polypeptide.

In some embodiments, purification is carried out using a column immobilized with a sulfonated polyaromatic compound. In general, the Wnt polypeptide is bound to the column immobilized with the sulfonated polyaromatic compound in a binding buffer containing a low concentration of salt. High salt destabilizes the non-covalent ionic interactions between the polypeptide and the column beads, thereby allow elution of the Wnt polypeptide. In some embodiments, the concentration of the salt used in the binding buffer is at most 0, 0.01, 5, 10, 15, 20, 25, 30, 40, 50 mM, or less. In some embodiments, the concentration of the salt used in the binding buffer is at least 0, 0.01, 5, 10, 15, 20, 25, 30, 40, 50 mM, or more. In some embodiments, one or more wash buffers are used to remove unbound impurities. In some embodiments, at most 1, 2, 3, 4, 5, or more wash steps are used. In some embodiments, at least 1, 2, 3, 4, 5 or less wash steps are used. In some embodiments, the concentration of the salt used in the wash buffer is at least 30, 40, 50, 60, 70, 80, 90, 100 mM, more. In some embodiments, the concentration of the salt used in the wash buffer is at most 30, 40, 50, 60, 70, 80, 90, 100 mM, less. In some embodiments, one or more elution steps follow. In some embodiments, the concentration of the salt in the elution buffer is at least 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1500, 2000 mM, or more. In some embodiments, the concentration of the salt in the elution buffer is at most 80, 90, 100, 110, 120, 130, 140, 150, 160, 170, 180, 190, 200, 250, 300, 350, 400, 450, 500, 550, 600, 650, 700, 750, 800, 850, 900, 950, 1000, 1500, 2000 mM, or less. Exemplary salt include sodium chloride, potassium chloride, magnesium chloride, calcium chloride, calcium phosphate, potassium phosphate, magnesium phosphate, sodium phosphate, ammonium sulfate, ammonium chloride, ammonium phosphate, and the like. In some embodiments, a detergent is also formulated into the binding buffer, wash buffer, and/or elution buffer. In some embodiments, the detergent is CHAPS or Triton X-100. In some embodiments, the percentage of CHAPS or Triton X-100 is at least 0.01%, 0.1%, 0.5%, 1%, 1.5%, 2%, 2.5%, 3%, 3.5%, 4%, 4.5%, 5%, or more. In some embodiments, the percentage of CHAPS or Triton X-100 is at most 0.01%, 0.1%, 0.5%, 1%, 1.5%, 2%, 2.5%, 3%, 3.5%, 4%, 4.5%, 5%, or less. In some instances, buffer components such as tris(hydroxymethyl)methylamine HCl (Tris-HCl), 3-{[tris(hydroxymethyl)methyl]amino}propanesulfonic acid (TAPS), N,N-bis(2-hydroxyethyl)glycine (Bicine), N-tris(hydroxymethyl)methylglycine (Tricine), 3-[N-Tris(hydroxymethyl)methylamino]-2-hydroxypropanesulfonic acid (TAPSO), 4-2-hydroxyethyl-1-piperazineethanesulfonic acid (HEPES), 3-(N-morpholino)propanesulfonic acid (MOPS), piperazine-N,N'-bis(2-ethanesulfonic acid) (PIPES), 2-(N-morpholino)ethanesulfonic acid (MES), and the like, are used. In some instances, the pH of the buffer is at least 4, 4.5, 5, 5.5, 6, 6.5, 7, 7.5, 8, 8.5, 9, or more. In some instances, the pH of the buffer is at most 4, 4.5, 5, 5.5, 6, 6.5, 7, 7.5, 8, 8.5, 9, or less. In some embodiments, the Wnt polypeptide is Wnt3a polypeptide, Wnt5a polypeptide, or Wnt10b polypeptide. In some embodiments, the Wnt polypeptide is Wnt3a polypeptide.

In some embodiments, the separation step is a hydrophobic purification step. In some embodiments, the hydrophobic purification step utilizes either beads immobilized with a hydrophobic ligand or a column immobilized with a hydrophobic ligand. Non-limiting examples of the ligands include butyl, octyl, phenyl, Protein A, and the like.

In some embodiments, the separation step is an affinity purification step. In some embodiments, the affinity purification step utilizes either beads immobilized with an affinity ligand or a column immobilized with an affinity ligand. Exemplary ligands include Frizzled receptor (Fzd) or its fragments thereof, and low-density lipoprotein receptor-related protein 6 (LRP6), or its fragments thereof.

In some embodiments, the concentration and yield of the eluted Wnt polypeptide is measured prior to subjecting to a further purification step. In some embodiments, the yield is at least about 20%, 30%, 40%, 50%, 60%, 70%, 80%, 90%, 95%, or more. In some embodiments, the yield is at most about 20%, 30%, 40%, 50%, 60%, 70%, 80%, 90%, 95%, or less. In some embodiments, the purity is at least about 20%, 30%, 40%, 50%, 60%, 70%, 80%, 90%, 95%, or more. In some embodiments, the purity is at most about 20%, 30%, 40%, 50%, 60%, 70%, 80%, 90%, 95%, or less.

In some embodiments, the purified Wnt polypeptide is Wnt3a polypeptide. In some embodiments, the Wnt3a polypeptide containing a palmitoylation at an amino acid residue corresponding to Serine 209 as set forth in SEQ ID NO:1 is purified from the separation step. In some embodiments, the Wnt3a polypeptide containing a palmitoylation at an amino acid residue corresponding to Cysteine 77 as set forth in SEQ ID NO:1 is purified from the separation step. In some embodiments, the Wnt3a polypeptide containing a palmitoylation at an amino acid residue corresponding to Cysteine 77 and a palmitoylation at an amino acid residue corresponding to Serine 209 as set forth in SEQ ID NO:1 is purified from the separation step. In some embodiments, the Wnt3a polypeptide containing a palmitoylation at an amino acid residue corresponding to Serine 209 as set forth in SEQ ID NO:1 and a palmitoylation at least one other amino acid residue is purified from the separation step. In some embodiments, the at least one other amino acid residue is not C77 as set forth in SEQ ID NO:1.

In some embodiments, the concentration of the Wnt3a specie containing the Serine 209 palmitoylation is high in the eluted product than the Wnt3a specie containing the Cysteine 77 palmitoylation. In some embodiments, the concentration of the two Wnt3a species is defined by a value, such as a ratio. In some embodiments, the ratio of the Wnt3a Serine 209 specie to the Wnt3a Cysteine 77 specie is between about 50:50, about 55:45, about 60:40, about 65:35, about 70:30, about 75:25, about 80:20, about 85:15, about 90:10, about 95:5, about 99:1, or about 100:0. In some embodiments, the concentration of the Wnt3a specie containing the Serine 209 palmitoylation is high in the eluted product than the Wnt3a specie containing the Cysteine 77 and the Serine 209 palmitoylations. In some embodiments, the concentration of the two Wnt3a species is defined by a value, such as a ratio. In some embodiments, the ratio of the Wnt3a Serine 209 specie to the Wnt3a Cysteine 77/Serine 209 specie is between about 50:50, about 55:45, about 60:40, about 65:35, about 70:30, about 75:25, about 80:20, about 85:15, about 90:10, about 95:5, about 99:1, or about 100:0.

In some embodiments, the further purification step is a step that utilizes pre-fabricated liposomes. In some embodiments, the liposome eliminates the serum (FBS) from the polypeptide preparation. In some embodiments, this latter step takes advantage of the hydrophobicity of the Wnt polypeptide, and eliminates the need for additional or subsequent purification steps, such as for example, subsequent gel filtration and/or chromatographic purification steps (e.g. heparin sulfate immobilized columns).

In some embodiments, the liposome is fabricated using methods well known in the art. Liposomes are artificially-prepared spherical vesicles that compose a lamellar phase lipid bilayer and an aqueous core. There are several types of liposomes, such as the multilamellar vesicle (MLV), small unilamellar liposome vesicle (SUV), the large unilamellar vesicle (LUV), and the cochleate vesicle. In some instances, liposomes are formed by phospholipids. In some embodiments, phospholipids are separated into those with diacylglyceride structures or those derived from phosphosphingolipids. In some embodiments, the diacylglyceride structures include phosphatidic acid (phosphatidate) (PA), phosphatidylethanolamine (cephalin) (PE), phosphatidylcholine (lecithin) (PC), phosphatidylserine (PS), and phosphoinositides such as phosphatidylinositol (PI), phosphatidylinositol phosphate (PIP), phosphatidylinositol bisphosphate (PIP2), and phosphatidylinositol triphosphate (PIP3). In some embodiments, phosphosphingolipids include ceramide phosphorylcholine, ceramide phosphorylethanolamine, and ceramide phosphoryllipid. In some embodiments, the liposomes are formed from phosphatidylcholines.

In some embodiments, the lipids are also selected based on its transition phase temperature ($T_m$), or the temperature interface between the liquid crystalline phase and the gel phase. In some embodiments, the $T_m$ is governed by the head group species, hydrocarbone length, unsaturation, and the charge. For example, short lipids (lipids containing 8, 10, or 12 tail carbon chain length) have liquid crystalline phase at temperatures below 4° C. However, liposomes manufactured from these short chain carbon lipids are toxic to cells because they dissolve cell membranes. Liposomes manufactured from longer carbon-chain lipids are not toxic to cells, but their transition temperatures are higher. For example, 1,2-dipalmitoyl-sn-glycero-3-phosphocholine (DPPC) which has a 16 tail carbon length, has a $T_m$ of about 41° C. In some embodiments, the lipids used herein have a $T_m$ of between about 10° C. and about 37° C., 15° C. and about 30° C., 18° C. and about 27° C., or 21° C. and about 25° C. In some embodiments, the lipids used herein have a $T_m$ of at least 22° C., 23° C., 24° C., or more. In some embodiments, the lipids used herein have a $T_m$ of at most 22° C., 23° C., 24° C., or less. In some embodiments, the lipids used herein have a tail carbon length of at least about 12, 13, 14, or more. In some embodiments, the lipids used herein have a tail carbon length of at most about 12, 13, 14, or less.

In some embodiments, the lipids are further selected based on the net charge of the liposome. In some embodiments, the liposome has a net charge of 0 at a pH of between about 4.0 and about 10.0, about 5.0 and about 9.0, about 6.5 and about 8.0, about 7.0 and about 7.8, or about 7.2 and about 7.6. In some embodiments, the liposome has a net charge of 0 at a pH of about 7.3, about 7.4, or about 7.5. In some embodiments, the liposome has a net positive charge at a pH of between about 4.0 and about 10.0, about 5.0 and about 9.0, about 6.5 and about 8.0, about 7.0 and about 7.8, or about 7.2 and about 7.6. In some embodiments, the liposome has a net positive charge at a pH of about 7.3, about 7.4, or about 7.5. In some embodiments, the liposome has a net negative charge at a pH of between about 4.0 and about 10.0, about 5.0 and about 9.0, about 6.5 and about 8.0, about 7.0 and about 7.8, or about 7.2 and about 7.6. In some embodiments, the liposome has a net negative charge at a pH of about 7.3, about 7.4, or about 7.5.

In some embodiments, lipids are selected from 1,2-dimyristoyl-sn-glycero-3-phosphocholine (DMPC), 1,2-dipalmitoyl-sn-glycero-3-phosphocholine (DPPC), 1-tetradecanoyl-2-hexadecanoyl-sn-glycero-3-phosphocholine (MPPC), 1,2-dimyristoyl-sn-glycero-3-phospho-L-serine (DMPS), and 1,2-dihexanoyl-sn-glycero-3-phosphocholine (DMPG). In some embodiments, the lipid is DMPC.

In some embodiments, an additional lipid is fabricated into the liposome. In some embodiments, the additional lipid is cholesterol. In some instances, the concentration of a phosphatidylcholine such as DMPC and cholesterol is defined by a value such as a ratio. In some embodiments, the ratio of the concentrations of phosphatidylcholine such as DMPC and cholesterol is between about 50:50, about 55:45, about 60:40, about 65:35, about 70:30, about 75:25, about 80:20, about 85:15, about 90:10, about 95:5, about 99:1, or about 100:0. In some embodiments, the ratio of the concentrations of phosphatidylcholine such as DMPC and cholesterol is about 90:10. In some embodiments, the concentration unit is moles. In some embodiments, the ratio is mole:mole.

In some embodiments, the Wnt polypeptide is reconstituted with a liposome at a concentration of at least about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.4, 0.5 ng/µL or more. In some embodiments, the Wnt polypeptide is reconstituted with a liposome at a concentration of at most about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.4, 0.5 ng/µL or less. In some embodiments, the Wnt polypeptide is Wnt3a polypeptide, Wnt5a polypeptide, or Wnt10b polypeptide. In some embodiments, the Wnt polypeptide is Wnt3a polypeptide.

In some embodiments, the Wnt polypeptide is reconstituted with a liposome at a ratio of at least about 0.1:50, 0.5:30, 1:20, or 1:14 Wnt polypeptide to liposome, or more. In some embodiments, the Wnt polypeptide is reconstituted with a liposome at a ratio of at most about 0.1:50, 0.5:30, 1:20, or 1:14 Wnt polypeptide to liposome, or less. In some instances, the ratio is a weight to weight ratio. In some instances, the unit of Wnt polypeptide is nanogram unit.

In some embodiments, the temperature at which the Wnt polypeptide is reconstituted with a liposome is at least between about 15° C. and about 37° C., about 18° C. and about 33° C., or about 20° C. and about 28° C. In some embodiments, the temperature is at least about 21° C., 22° C., 23° C., 24° C., 25° C., 26° C., 27° C., or more. In some embodiments, the temperature is at most about 21° C., 22° C., 23° C., 24° C., 25° C., 26° C., 27° C., or less. In some embodiments, the Wnt polypeptide is Wnt3a polypeptide, Wnt5a polypeptide, or Wnt10b polypeptide. In some embodiments, the Wnt polypeptide is Wnt3a polypeptide.

In some embodiments, the Wnt polypeptide is integrated into the liposomal membrane. In some cases, the Wnt polypeptide protrudes from the liposomal membrane onto the surface of the lipid membrane. In some instances, the Wnt polypeptide is not incorporated into the aqueous core of the liposome. In some embodiments, the Wnt polypeptide is Wnt3a polypeptide, Wnt5a polypeptide, or Wnt10b polypeptide. In some embodiments, the Wnt polypeptide is Wnt3a polypeptide. In some embodiments, the Wnt3a polypeptide is integrated into the liposomal membrane. In some cases, the Wnt3a polypeptide protrudes from the liposomal membrane onto the surface of the lipid membrane. In some instances, the Wnt3a polypeptide is not incorporated into the aqueous core of the liposome.

In some embodiments, the Wnt polypeptide reconstituted with a liposome is referred to as liposomal Wnt polypeptide or L-Wnt. In some embodiments, the Wnt polypeptide is Wnt3a polypeptide, Wnt5a polypeptide, or Wnt10b polypeptide. In some embodiments, the Wnt polypeptide is Wnt3a polypeptide. In some embodiments, the Wnt3a polypeptide reconstituted with a liposome is referred to as liposomal Wnt3a polypeptide or L-Wnt3a. In some embodiments, the Wnt polypeptide is Wnt5a polypeptide. In some embodiments, the Wnt5a polypeptide reconstituted with a liposome is referred to as liposomal Wnt5a polypeptide or L-Wnt5a. In some embodiments, the Wnt polypeptide is Wnt10b polypeptide. In some embodiments, the Wnt10b polypeptide reconstituted with a liposome is referred to as liposomal Wnt10b polypeptide or L-Wnt10b.

In some embodiments, the L-Wnt undergoes a centrifugation step and is then suspended in a buffer such as phosphate buffered saline (PBS). In some instances, the L-Wnt is stored under nitrogen. In some instances, the L-Wnt is stable under nitrogen without substantial loss of activity. In some instances, the L-Wnt is stored at a temperature of between about 1° C. and about 8° C. In some instances, the L-Wnt is stable at a temperature of at least about 1° C., 2° C., 3° C., 4° C., 5° C., 6° C., 7° C., 8° C., or more without substantial loss of activity. In some instances, the L-Wnt is stable at a temperature of at most about 1° C., 2° C., 3° C., 4° C., 5° C., 6° C., 7° C., 8° C., or less without substantial loss of activity. In some embodiments, the L-Wnt is stable for at least about 10, 15, 20, 25, 30, 35, 40, 45, 50, 55, 60, 65, 70, 75, 80, 85, 90, 95, 100, 101, 102, 103, 104, 105, 106, 107, 108, 109, 110, 115, 120, 130, 140, 150, 160, 170, 180, 190, 200, 300, 356, 400, 700, 1000 days, or more without substantial loss of activity. In some embodiments, the L-Wnt is stable for at most about 10, 15, 20, 25, 30, 35, 40, 45, 50, 55, 60, 65, 70, 75, 80, 85, 90, 95, 100, 101, 102, 103, 104, 105, 106, 107, 108, 109, 110, 115, 120, 130, 140, 150, 160, 170, 180, 190, 200, 300, 356, 400, 700, 1000 days, or less without substantial loss of activity.

In some embodiments, the L-Wnt3a undergoes a centrifugation step and is then suspended in a buffer such as phosphate buffered saline (PBS). In some instances, the L-Wnt3a is stored under nitrogen. In some instances, the L-Wnt3a is stable under nitrogen without substantial loss of activity. In some instances, the L-Wnt3a is stored at a temperature of between about 1° C. and about 8° C. In some instances, the L-Wnt3a is stable at a temperature of at least about 1° C., 2° C., 3° C., 4° C., 5° C., 6° C., 7° C., 8° C., or more without substantial loss of activity. In some instances, the L-Wnt3a is stable at a temperature of at most about 1° C., 2° C., 3° C., 4° C., 5° C., 6° C., 7° C., 8° C., or less without substantial loss of activity. In some embodiments, the L-Wnt3a is stable for at least about 10, 20, 30, 40, 50, 60, 70, 80 90, 100, 110, 120, 130, 140, 150, 160, 170, 180, 190, 200, 300, 356, 400, 700, 1000 days, or more without substantial loss of activity. In some embodiments, the L-Wnt3a is stable for at most about 10, 20, 30, 40, 50, 60, 70, 80 90, 100, 110, 120, 130, 140, 150, 160, 170, 180, 190, 200, 300, 356, 400, 700, 1000 days, or less without substantial loss of activity.

In some instances, the term "without substantial loss of activity" refers to the functional activity of a liposomal Wnt polypeptide is near to that of the corresponding native Wnt polypeptide in the absence of a liposome. In some instances, the functional activity of the liposomal Wnt polypeptide is at least about 100%, 99%, 95%, 90%, 85%, 80%, 75%, 70%, 60%, 50%, 40%, or more compared to the functional activity of the native Wnt polypeptide. In some instances, the functional activity of the liposomal Wnt polypeptide is at most about 100%, 99%, 95%, 90%, 85%, 80%, 75%, 70%, 60%, 50%, 40%, or less compared to the functional activity of the native Wnt polypeptide. In some instances, the functional activity of the Wnt polypeptides is detected using assays such as for example mass spectroscopy, assays associated with biomarker analysis which are described elsewhere herein, transplant surgery such as sub-renal capsule transplant surgery, spinal fusion surgery, ALP, TRAP, and TUNEL staining, immunohistochemistry, and Micro-CT analyses and quantification of graft growth.

In some instances, the term "stable" refers to Wnt polypeptides as in a folded state and is not unfolded or degraded. In some instances, the term "stable" also refers to Wnt polypeptides retaining functional activity without substantial loss of activity. In some instances, assays used to determine stability assays that establish the activity of the Wnt polypeptides, as such those described above, and also include such as LSL cell-based assays such as mice LSL cell-based assay.

In some embodiments, the purification method described herein exploits the hydrophobic domains of the Wnt polypeptide and does not interfere with Wnt polypeptide conformation or functional activity. In some embodiments, the Wnt polypeptide is Wnt3a polypeptide, Wnt5a polypeptide, or Wnt10b polypeptide. In some embodiments, the Wnt polypeptide is Wnt3a polypeptide. In some cases, the hydrophobic domain of the Wnt3a polypeptide contains a palmitoylation on a serine residue corresponding to the Serine 209 as set forth in SEQ ID NO:1.

In some embodiments, the affinity of Wnt polypeptide to liposome is lower than the Wnt polypeptide binding partners. In some embodiments, the Wnt polypeptide is Wnt3a polypeptide, Wnt5b polypeptide, or Wnt10b polypeptide. In some embodiments, the Wnt polypeptide is Wnt3a polypeptide. In some embodiments, the affinity of Wnt3a polypeptide to liposome is lower than the Wnt3a polypeptide binding partners. In some embodiments, the Wnt3a polypeptide binding partners include Frizzled protein, its fragments thereof, LRP6 protein, and its fragments thereof. In some embodiments, the affinity of Wnt3a to liposome is between about 4 nM and about 50 nM, and about 4.5 nM and about 20 nM, and about 5 nM and about 15 nM. In some embodiments, the affinity of Wnt3a to liposome is at least about 5.5 nM, 6 nM, 6.5 nM, 7 nM, 7.5 nM, 8 nM, 8.5 nM, 9 nM, 9.5 nM, 10 nM, 11 nM, 12 nM, 13 nM, 14 nM, or more. In some embodiments, the affinity of Wnt3a to liposome is at most about 5.5 nM, 6 nM, 6.5 nM, 7 nM, 7.5 nM, 8 nM, 8.5 nM, 9 nM, 9.5 nM, 10 nM, 11 nM, 12 nM, 13 nM, 14 nM, or less. In some embodiments, the affinity of Wnt3a polypeptide to its binding partners is between about 0.01 nM to about 4 nM, about 0.1 nM to about 4 nM, or about 1 nM to about 4 nM. In some instances, the affinity of Wnt3a polypeptide to its binding partners is at least about 1.1 nM, 1.3 nM, 1.5 nM, 1.7 nM, 2 nM, 2.3 nM, 2.5 nM, 2.7 nM, 3 nM, 3.1 nM, 3.2 nM, 3.3 nM, 3.4 nM, 3.5 nM, 3.6 nM, 3.7 nM, 3.8 nM, 3.9 nM, or more. In some instances, the affinity of Wnt3a polypeptide to its binding partners is at most about 1.1 nM, 1.3 nM, 1.5 nM, 1.7 nM, 2 nM, 2.3 nM, 2.5 nM, 2.7 nM, 3 nM, 3.1 nM, 3.2 nM, 3.3 nM, 3.4 nM, 3.5 nM, 3.6 nM, 3.7 nM, 3.8 nM, 3.9 nM, or less.

Different purification schemes yield different amounts of purified polypeptide. In some embodiments, the Wnt3a polypeptide containing a palmitoylation at an amino acid residue that correspond to Cysteine 77 as set forth in SEQ ID NO:1 is the active form. In some embodiments, the Wnt3a polypeptide containing a palmitoylation at an amino acid residue that correspond to Serine 209 as set forth in SEQ ID NO:1 is the active form. In some embodiments, the Wnt3a polypeptide containing a palmitoylation at an amino acid residue that correspond to Serine 209 and a palmitoylation at an amino acid residue that correspond to Cysteine 77 as set forth in SEQ ID NO:1 is the active form. In some embodiments, the Wnt3a polypeptide containing a palmitoylation at an amino acid residue that correspond to Serine 209 and a palmitoylation at an amino acid residue that correspond to Cysteine 77 as set forth in SEQ ID NO:1 is not the active form. In some embodiments, the Wnt3a polypeptide containing a palmitoylation at an amino acid residue that correspond to Cysteine 77 as set forth in SEQ ID NO:1 is not the active form. In some embodiments, mass spectrometry coupled with additional assays for detecting or measuring the activity of the Wnt polypeptide (e.g. Wnt3a polypeptide) are used to identify the active specie. In some cases, the additional assays include assays associated with biomarker analysis which are described elsewhere herein, transplant surgery such as sub-renal capsule transplant surgery, spinal fusion surgery, ALP, TRAP, and TUNEL staining, immunohistochemistry, and Micro-CT analyses and quantification of graft growth.

In some aspects, the concentration of the liposomal Wnt3a specie containing the Serine 209 palmitoylation is higher in the eluted product than the Wnt3a specie containing the Cysteine 77 palmitoylation. In some embodiments, the concentration of the two Wnt3a species is defined by a value, such as a ratio. In some embodiments, the ratio of the Wnt3a Serine 209 specie to the Wnt3a Cysteine 77 specie is between about 50:50, about 55:45, about 60:40, about 65:35, about 70:30, about 75:25, about 80:20, about 85:15, about 90:10, about 95:5, about 99:1, or about 100:0. In some embodiments, the concentration of the liposomal Wnt3a specie containing the Serine 209 palmitoylation is high in the eluted product than the Wnt3a specie containing the Cysteine 77 and the Serine 209 palmitoylations. In some embodiments, the concentration of the two Wnt3a species is defined by a value, such as a ratio. In some embodiments, the ratio of the Wnt3a Serine 209 specie to the Wnt3a Cysteine 77/Serine 209 specie is between about 50:50, about 55:45, about 60:40, about 65:35, about 70:30, about 75:25, about 80:20, about 85:15, about 90:10, about 95:5, about 99:1, or about 100:0.

In some instances, previous purification schemes, including those described in the references disclosed herein, yield a mixture of the two species (e.g. 1:5 single modified/active: dual modified/inactive). Using the purification scheme described herein, in some instances, the predominant polypeptide specie is in the single modified (at Ser209), active configuration. In some instances, the purification method described herein provides a Wnt3a composition that contains predominantly an active form of the polypeptide that contains lipid modification at Ser209. In some instances, the purification method described herein provides a Wnt3a composition that is not contaminated by other polypeptide species such as Cys77 Wnt3a specie.

In some embodiments, described herein is a method of preparing a liposomal Wnt polypeptide that comprises the steps of contacting a sample comprising Wnt polypeptides to an aqueous solution of liposomes, wherein the phospholipids comprising the liposomes have a phase transition temperature from about 10° C. to about 25° C. In some embodiments, described herein is a method of preparing a liposomal Wnt polypeptide that comprises the steps of contacting a sample comprising Wnt polypeptides to an aqueous solution of liposomes, wherein the phospholipids comprising the liposome have a tail carbon length of between about 12 carbons and about 14 carbons. In some embodiments, the Wnt polypeptide is Wnt3a polypeptide, Wnt5a polypeptide, or Wnt10b polypeptide. In some embodiments, the Wnt polypeptide is Wnt3a polypeptide.

In some embodiments, disclosed herein is a method of preparing a liposomal Wnt3a polypeptide which comprises the steps of (a) harvesting Wnt3a polypeptides from a conditioned media comprising Chinese hamster ovary (CHO) cells; (b) introducing the Wnt3a polypeptides to an ion-exchange column immobilized with a sulfonated polyaromatic compound; (c) eluting the Wnt3a polypeptides from the ion-exchange column utilizing a step gradient; and (d) contacting the Wnt3a polypeptides from step (c) with an aqueous solution of liposomes.

In some embodiments, disclosed herein is a method of preparing a liposomal Wnt5a polypeptide which comprises the steps of (a) harvesting Wnt5a polypeptides from a conditioned media comprising Chinese hamster ovary (CHO) cells; (b) introducing the Wnt5a polypeptides to an ion-exchange column immobilized with a sulfonated polyaromatic compound; (c) eluting the Wnt5a polypeptides from the ion-exchange column utilizing a step gradient; and (d) contacting the Wnt5a polypeptides from step (c) with an aqueous solution of liposomes.

In some embodiments, disclosed herein is a method of preparing a liposomal Wnt10b polypeptide which comprises the steps of (a) harvesting Wnt10b polypeptides from a conditioned media comprising Chinese hamster ovary (CHO) cells; (b) introducing the Wnt10b polypeptides to an ion-exchange column immobilized with a sulfonated polyaromatic compound; (c) eluting the Wnt10b polypeptides from the ion-exchange column utilizing a step gradient; and (d) contacting the Wnt10b polypeptides from step (c) with an aqueous solution of liposomes.

Functional assays to determine the biological activity of Wnt polypeptides are well known in the art and can include, for example, stabilization of β-catenin, growth promotion of stem cells, quantitation of the amount of Wnt polypeptide present in a non-functional assay, e.g. immunostaining, ELISA, quantitation on Coomasie or silver stained gel, etc., and analysis of the ratio of functionally active Wnt to total Wnt. An exemplary assay for biological activity includes contacting a Wnt composition with cells, e.g. mouse L cells and then culturing the cells for a period of time sufficient to stabilize β-catenin, such as for at least about 1 hour. The cells are then lysed and the cell lysate is resolved by SDS PAGE. The resolved cell lysate components from the SDS PAGE is subsequently transferred to a nitrocellulose and then probed with antibodies specific for β-catenin. Other assays for analysis of Wnt activity include C57MG transformation and *Xenopus* animal cap assays for induction of target genes. See U.S. Pat. No. 7,335,643, for additional exemplary assays.

C. Methods of Use

Disclosed herein are methods, processes, compositions, and kits for generating bone graft materials for use at a site of bone defect. Also disclosed herein are methods, processes, compositions, and kits for enhancing mammalian bone marrow cells. In some instances, the bone defect refers to a bone injury such as a bone fracture in which grafting materials are needed to stimulate and guide reparative growth of natural bone.

In some embodiments, the method refers to a method of generating bone graft materials, which comprises the steps of (a) contacting a sample comprising mammalian bone marrow cells ex-vivo with a liposomal WNT polypeptide; (b) washing the sample to remove free liposomal WNT polypeptide; and (c) transplanting the liposomal WNT polypeptide treated bone graft materials into a site of bone defect. In some embodiments, the Wnt polypeptide is Wnt3a polypeptide, Wnt5a polypeptide, or Wnt10b polypeptide.

In some embodiments, the Wnt polypeptide is Wnt3a polypeptide. In some embodiments, the method refers to a method of generating bone graft materials, which comprises the steps of (a) contacting a sample comprising mammalian bone marrow cells ex-vivo with a liposomal WNT3a polypeptide; (b) washing the sample to remove free liposomal WNT3a polypeptide; and (c) transplanting the liposomal WNT3a polypeptide treated bone graft materials into a site of bone defect.

In some embodiments, the Wnt polypeptide is Wnt5a polypeptide. In some embodiments, the method refers to a method of generating bone graft materials, which comprises the steps of (a) contacting a sample comprising mammalian bone marrow cells ex-vivo with a liposomal WNT5a polypeptide; (b) washing the sample to remove free liposomal WNT5a polypeptide; and (c) transplanting the liposomal WNT5a polypeptide treated bone graft materials into a site of bone defect.

In some embodiments, the Wnt polypeptide is Wnt10b polypeptide. In some embodiments, the method refers to a method of generating bone graft materials, which comprises the steps of (a) contacting a sample comprising mammalian bone marrow cells ex-vivo with a liposomal WNT10b polypeptide; (b) washing the sample to remove free liposomal WNT10b polypeptide; and (c) transplanting the liposomal WNT10b polypeptide treated bone graft materials into a site of bone defect.

In some embodiments, the process refers to a mammalian bone marrow composition produced by a process that comprises the step of contacting isolated mammalian bone marrow cells ex-vivo with a liposomal WNT polypeptide, wherein the contacting time is between about 30 minutes and about 4 hours. In some embodiments, the Wnt polypeptide is Wnt3a polypeptide, Wnt5a polypeptide, or Wnt10b polypeptide.

In some embodiments, the Wnt polypeptide is Wnt3a polypeptide. In some embodiments, the process refers to a mammalian bone marrow composition produced by a process which comprises the step of contacting isolated mammalian bone marrow cells ex-vivo with a liposomal WNT3a polypeptide, wherein the contacting time is between about 30 minutes and about 4 hours.

In some embodiments, the Wnt polypeptide is Wnt5a polypeptide. In some embodiments, the process refers to a mammalian bone marrow composition produced by a process which comprises the step of contacting isolated mammalian bone marrow cells ex-vivo with a liposomal WNT5a polypeptide, wherein the contacting time is between about 30 minutes and about 4 hours.

In some embodiments, the Wnt polypeptide is Wnt10b polypeptide. In some embodiments, the process refers to a mammalian bone marrow composition produced by a process which comprises the step of contacting isolated mammalian bone marrow cells ex-vivo with a liposomal WNT10b polypeptide, wherein the contacting time is between about 30 minutes and about 4 hours.

In some embodiments, the composition refers to a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal WNT polypeptide. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the Wnt polypeptide is Wnt3a polypeptide, Wnt5a polypeptide, or Wnt10b polypeptide.

In some embodiments, the Wnt polypeptide is Wnt3a polypeptide. In some embodiments, the composition refers to a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal WNT3a polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the Wnt polypeptide is Wnt5a polypeptide. In some embodiments, the composition refers to a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal WNT5a polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the Wnt polypeptide is Wnt10b polypeptide. In some embodiments, the composition refers to a composition of isolated enhanced mammalian bone marrow cells wherein the cells have an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal WNT10b polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the composition also refers to a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal WNT polypeptide. In some embodiments, the biomarkers are selected from Osteocalcin, Osteopontin, Axin2, Lef1, and Tcf4. In some embodiments, the biomarkers are selected from Osteocalcin, and Osteopontin. In some embodiments, the Wnt polypeptide is Wnt3a polypeptide, Wnt5a polypeptide, or Wnt10b polypeptide.

In some embodiments, the Wnt polypeptide is Wnt3a polypeptide. In some embodiments, the composition also refers to a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt3a polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the Wnt polypeptide is Wnt5a polypeptide. In some embodiments, the composition also refers to a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt5a polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the Wnt polypeptide is Wnt10b polypeptide. In some embodiments, the composition also refers to a composition of mammalian bone marrow cells obtained from a human subject at or older than 35 years of age, wherein the mammalian bone marrow cells express an enhanced expression level in one or more of the biomarkers selected from the group consisting of: Runx2, Osterix, Osteocalcin, Osteopontin, alkaline phosphatase, collagen type I, Axin2, Lef1, and Tcf4, after treatment with a liposomal Wnt10b polypeptide. In some embodiments, the biomarkers are selected from Osteocalcin, Osteopontin, Axin2, Lef1, and Tcf4. In some embodiments, the biomarkers are selected from Osteocalcin, and Osteopontin.

In some embodiments, the enhanced expression level is compared to untreated mammalian bone marrow cells. In some instances, the enhanced expression level is between about 1% and about 100%, about 1% and about 50%, about 2% and about 20%, about 3% and about 15%, or about 4% and about 10% compared to untreated mammalian bone marrow cells. In some instances, the enhanced expression level is at least about 5%, 5.5% 6%, 6.5% 7%, 7.5%, 8%, 8.5%, 9%, 9.5%, or more compared to untreated mammalian bone marrow cells. In some instances, the enhanced expression level is at most about 5%, 5.5% 6%, 6.5% 7%, 7.5%, 8%, 8.5%, 9%, 9.5%, or less compared to untreated mammalian bone marrow cells.

In some embodiments, the mammalian bone marrow cells further have a decreased expression level in a biomarker selected from SOX9 and PPARγ after treatment with liposomal WNT polypeptide. In some instances, the decreased expression level in the mammalian bone marrow cells are compared to untreated mammalian bone marrow cells. In some cases, the decreased expression level is between about 1% and about 100%, about 2% and about 80%, about 3% and about 50%, about 3% and about 30%, or about 4% and about 20% compared to untreated mammalian bone marrow cells.

In some embodiments, the bone marrow cells further comprise a decrease in apoptosis level compared to untreated mammalian bone marrow cells. In some instances, the decrease in apoptosis level is at least about 1%, 5%, 10%, 20%, 30%, 40%, 50%, 60%, 70%, 80%, 90%, 100%, 200%, or more compared to untreated mammalian bone marrow cells. In some instances, the decrease in apoptosis level is at most about 1%, 5%, 10%, 20%, 30%, 40%, 50%, 60%, 70%, 80%, 90%, 100%, 200%, or less compared to untreated mammalian bone marrow cells.

In some embodiments, the mammalian bone marrow cells comprise enhanced osteogenic potential compared to untreated mammalian bone marrow cells. In some embodiments, the enhanced osteogenic potential comprises new bone growth level at the site of bone defect after transplanting treated mammalian bone marrow cells. In some instances, the new bone growth level of transplanted treated mammalian bone marrow cells is between about 1% and about 20% or about 5% and about 12% compared to the new bone growth level of transplanted untreated mammalian bone marrow cells. In some instances, the new bone growth level of transplanted treated mammalian bone marrow cells is increased by about 1.5-fold, about 2-fold, about 3-fold, about 4-fold, about 5-fold, about 10-fold, about 20-fold, about 50-fold, about 100-fold, or more compared to the new bone growth level of transplanted untreated mammalian bone marrow cells.

The bone graft material, as used herein, refers to a cellular composition obtained from a donor, in which the donor can be living or cadaveric. Bone graft material typically comprises complex cell populations, and includes stem cells such as mesenchymal stem cells, and in some instances, also comprises osteocytes and progenitors thereof. In some instances, the cells are adherent bone marrow cells or non-adherent bone marrow cells. In some instances, the bone marrow cells are adherent bone marrow cells. In some instances, the adherent bone marrow cells are bone marrow stem cells or bone marrow progenitor cells. In some instances, the adherent bone marrow cells are bone marrow stromal cells. In some embodiments, the donor is allogeneic. In some instances, the donor is autologous relative to the recipient. The quantity of cells for a bone graft can vary with the donor, the recipient, purpose of graft, and the like. A bone graft can comprise up to about $10^3$, up to about $10^4$, up to about $10^5$, up to about $10^6$, up to about $10^7$, up to about $10^8$, up to about $10^9$, up to about $10^{10}$ or more cells.

The bone graft material is obtained from the donor, for example from the iliac crest, from the mandibular symphysis (chin area), from reaming, aspirating, and irrigating the femur and/or tibia, fibula, ribs, anterior mandibular ramus; parts of spinal bone, e.g. those removed during surgery, cadaver bones, etc. In some instances, the graft material is harvested from bone marrow, for example scraped from the endosteal surface of a suitable bone, or from a block graft containing marrow and a small block of bone. In some cases, allograft bone is taken from cadavers, bone banks, etc. for example from a femoral head from hip replacement surgery. In some instances, the bone graft material is fresh, or is cryo-preserved as known in the art until it is needed.

In some embodiments, the cells of the bone graft are suspended in a suitable culture medium in the presence of an effective dose of a liposomal Wnt polypeptide, e.g. L-Wnt3a, L-Wnt5a, or L-Wnt10b. Any suitable medium can be used, e.g. DMEM, RPMI, PBS, etc. Cells are typically resuspended at a concentration that maintains viability during the incubation procedure, e.g. up to about $10^4$/ml, up to about $10^5$/ml, up to about $10^6$/ml, up to about $10^7$/ml.

In some instances, the contacting temperature is between about 0° C. and about 37° C., or about 20° C. and about 25° C. In some embodiments, the contacting temperature is lower, e.g. up to about 32° C., up to about 25° C., up to about 15° C., up to about 10° C., up to about 8° C., up to about 4° C., up to about 1° C., but typically above freezing unless specifically prepared for cryopreservation. In some instances, the incubation temperature is at least about 20° C., 21° C., 22° C., 23° C., 24° C., 25° C., or more. In some instances, the incubation temperature is at most about 20° C., 21° C., 22° C., 23° C., 24° C., 25° C., or less.

In some cases, the bone graft material contacts with the Wnt polypeptide for at least about 10 minutes, at least about 30 minutes, at least about 1 hour, at least about 2 hours, at least about 3 hours, and up to about 36 hours, up to about 24 hours, up to about 18 hours, up to about 15 hours, up to about 12 hours, up to about 8 hours, up to about 6 hours, or up to about 4 hours.

The effective dose of the Wnt polypeptide can vary depending on the source, purity, preparation method, etc. In some instances, the effective dose of the Wnt polypeptide is at least about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or more. In some instances, the effective dose of the Wnt polypeptide is at most about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or less.

In some embodiments, the Wnt polypeptide is L-Wnt3a, the effective dose of the Wnt3a polypeptide is at least about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or more. In some instances, the effective dose of the Wnt3a polypeptide is at most about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or less.

In some instances, the Wnt polypeptide is L-Wnt5a, the effective dose of the Wnt5a polypeptide is at least about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or more. In some instances, the effective dose of the Wnt5a polypeptide is at most about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or less.

In some instances, the Wnt polypeptide is L-Wnt10b, the effective dose of the Wnt10b polypeptide is at least about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or more. In some instances, the effective dose of the Wnt10b polypeptide is at most about 0.01 µg/ml, 0.05 µg/ml, 0.1 µg/ml, 0.15 µg/ml, 0.2 µg/ml, 0.25 µg/ml, 0.3 µg/ml, 0.35 µg/ml, 0.4 µg/ml, 0.45 µg/ml, 0.5 µg/ml, 0.6 µg/ml, 0.7 µg/ml, 0.8 µg/ml, 0.9 µg/ml, 1.0 µg/ml, 1.5 µg/ml, 2.0 µg/ml, 2.5 µg/ml, 3.0 µg/ml, 3.5 µg/ml, 4.0 µg/ml, 4.5 µg/ml, 5.0 µg/ml, 7.5 µg/ml, 10 µg/ml, 15 µg/ml, 25 µg/ml, 50 µg/ml, 100 µg/ml, or less.

In some embodiments, the bone graft material is incubated with aWnt polypeptide for a period of time sufficient to enhance osteogenic capacity. The enhancement can be measured in various ways such as the use of biomarkers described herein, e.g. by increased expression of Axin2, by increased mitotic activity in the bone graft material (measured at from about day 2 to about day 6 post-transplantation); by increased bone formation post-transplantation, by increased expression of Runx2 or Osteocalcin, by reduced apoptosis post-transplantation; or by volume of bone produced post-transplantation.

Following incubation, the bone graft material can be transplanted into a recipient following conventional protocols, e.g. for repair of spinal bone, fractures, dental supports, and the like.

In some embodiments, prior to transplanting the Wnt-treated bone graft material back to the patient, a wash step is performed to remove any free liposomal Wnt polypeptides. In some embodiments, at least about 1, 2, 3, 4, 5 wash times or more is performed. In some embodiments, at most about 1, 2, 3, 4, 5 wash times or less is performed. In some embodiments, any suitable buffer is used for washing, such as for example phosphate buffered saline solution.

In some instances, the remaining liposomal Wnt after the washing step is at most about 0.01 µg (picogram), 0.05 µg, 0.1 µg, 0.5 µg, 1 µg, 1.5 µg, 2 µg, 2.5 µg, 3 µg, 3.5 µg, 4 µg, 4.5 µg, 5 µg, 5.5 µg, 6 µg, or less. In some instances, the remaining liposomal Wnt after the washing step is at least about 0.01 µg (picogram), 0.05 µg, 0.1 µg, 0.5 µg, 1 µg, 1.5 µg, 2 µg, 2.5 µg, 3 µg, 3.5 µg, 4 µg, 4.5 µg, 5 µg, 5.5 µg, 6 µg, or more.

In some instances, the method described herein for treatment of bone graft materials with Wnt allows for control of exposure time of the Wnt polypeptide to cells, duration of the exposure, concentration of exposure, and/or toxicity. In some instances, the method described herein for treatment of bone graft materials with Wnt3a allows for control of exposure time of the Wnt3a polypeptide to cells, duration of the exposure, concentration of exposure, and/or toxicity.

In some embodiments, osteogenic potential is restored to aged bone grafts by incubation with a Wnt polypeptide, such as for example L-Wnt3a, L-Wnt5a, or L-Wnt10b. In some instances, liposomal Wnt3a treatment reduces cell death in aged bone grafts. In some instances after transplantation, bone grafts treated with liposomal Wnt3a gave rise to more bone (p<0.05). In some instances, liposomal Wnt3a treatment enhanced cell survival in the graft and re-established the bone-forming ability of grafts from aged animals.

In some embodiments, mammalian bone marrow cells are obtained from any mammal, including but not limited to a human. In some instances, the donor is a rodent, such as a mice, or rat. In some instances, the donor is a rabbit. In some instances, the donor is a human. In some instances, the donor is self and the bone marrow cells are autologous. In some instances, as described elsewhere herein, autologous bone marrow cells include adherent and non-adherent bone marrow cells. In some instances, the autologous bone marrow cells are adherent bone marrow cells. In some instances, the autologous bone marrow cells include bone marrow stem cells and bone marrow progenitor cells. In some instances, the autologous bone marrow cells include bone marrow stromal cells. In some instances, the donor is another individual and the bone marrow cells are allogeneic. In some instances, the allogeneic bone marrow cells are obtained from a living donor or a cadaveric donor. In some cases, as described elsewhere herein, the allogenic bone marrow cells include adherent and non-adherent bone marrow cells. In some cases, the allogeneic bone marrow cells are adherent bone marrow cells. In some cases, the allogeneic bone marrow cells include bone marrow stem cells and bone marrow progenitor cells. In some cases, the allogeneic bone marrow cells include bone marrow stromal cells. In some instances, the donor is an individual at or older than 35 years of age. In some instances, the bone marrow cells obtained from an individual at or older than 35 years of age is considered old bone marrow cells or aged bone marrow cells. In some embodiments, the donor is an individual younger than 35 years of age. In some instances, the bone marrow cells obtained from an individual younger than 35 years of age is considered young bone marrow cells. In some instances, the bone marrow cells obtained from an individual at or older than 35 years of age is autologous bone marrow cells or allogeneic bone marrow cells. In some instances, the bone marrow cells obtained from an individual younger than 35 years of age is autologous bone marrow cells or allogenic bone marrow cells. As used herein, the terms "individual(s)", "subject(s)", "donor(s)", and "patient(s)" are used interchangeably herein, and means any mammal, including but not limited to a human.

In some embodiments, the methods, compositions, processes, and kits described herein provide a clinically applicable regenerative medicine-based strategy for revitalizing bone grafts from aged patients, and from other patients with diminished healing potential, such as, for example, smokers, diabetics, or patients, with nutritional deficits.

In some embodiments, methods for determining the expression level or the presence of biomarkers such as Runx2, Osterix, Osteocalcin, Osteopontin, alkaline phosphatase, collagen type I, Axin2, Lef1, Tcf4, SOX9 and PPARγ are well known in the art. In some instances, the expression level or the presence of biomarkers are measured, for example, by flow cytometry, immunohistochemistry, Western Blot, immunoprecipitation, magnetic bead selection, and quantification of cells expressing either of these biomarkers. Biomarker RNA or DNA expression levels could be measured by RT-PCR, Qt-PCR, microarray, Northern blot, or other similar technologies. As used herein, the term "biomarker" and "marker" are used interchangeably.

As disclosed herein, determining the expression or presence of the biomarker of interest at the polypeptide or nucleotide level is accomplished using any detection method known to those of skill in the art. By "detecting expression" or "detecting the level of" is intended to determine the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In certain aspects, the expression or presence of these various biomarkers and any clinically useful prognostic markers in a biological sample are detected at the protein or nucleic acid level, using, for example, immunohistochemistry techniques or nucleic acid-based techniques such as in situ hybridization and RT-PCR. In some embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of one or more biomarkers is carried out through gel electrophoresis. In one embodiment, the determination is carried out through transfer to a membrane and hybridization with a specific probe.

In other embodiments, the determining the expression or presence of one or more biomarkers is carried out by a diagnostic imaging technique.

In still other embodiments, the determining the expression or presence of one or more biomarkers is carried out by a detectable solid substrate. In one embodiment, the detectable solid substrate is paramagnetic nanoparticles functionalized with antibodies.

In some embodiments, expression of a biomarker is detected on a protein level using, for example, antibodies that are directed against specific biomarker proteins. These antibodies are used in various methods such as Western blot, ELISA, multiplexing technologies, immunoprecipitation, or immunohistochemistry techniques. In some embodiments, detection of biomarkers is accomplished by ELISA. In some embodiments, detection of biomarkers is accomplished by electrochemiluminescence (ECL).

In some embodiments, expression level of a biomarker protein of interest in a biological sample is detected by means of a binding protein capable of interacting specifically with that biomarker protein or a functionally active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

As used herein, the term "antibody" is used in the broadest sense and covers fully assembled antibodies, antibody fragments that can bind antigen (e.g., Fab, F(ab)$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that can be present in minor amounts.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain $C_{H1}$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

In some embodiments, expression or presence of one or more biomarkers or other proteins of interest within a biological sample, for example, a tissue sample, is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

In some embodiments, the expression or presence of one or more of the biomarkers described herein are also determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes are synthesized by one of skill in the art, or derived from appropriate biological preparations. Probes are specifically designed to be labeled, for example, with a radioactive label, a fluorescent label, an enzyme, a chemiluminescent tag, a colorimetric tag, or other labels or tags that are discussed above or that are known in the art. Examples of molecules that are utilized as probes include, but are not limited to, RNA and DNA.

For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In some embodiments, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan® System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference in its entirety. The detection of expression also comprises using nucleic acid probes in solution.

In some embodiments, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference in its entirety. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety. In some embodiments, arrays are packaged in such a manner as to allow for diagnostics or other manipulation of an all-inclusive device.

D. Kits/Article of Manufacture

Disclosed herein, in certain embodiments, are kits and articles of manufacture for use with one or more methods, processes, and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

The articles of manufacture provided herein contain packaging materials. Examples of packaging materials include, but are not limited to, bottles, tubes, bags, containers, bottles, and any packaging material suitable for a selected formulation and intended mode of administration and treatment.

For example, the container(s) include L-Wnt polypeptides. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Further details of the invention are provided in the following non-limiting Examples.

Example 1

Production and Purification of Human Wnt3a Polypeptide

Human WNT3A is a lipid-modified human stem cell growth factor that is effective in activating adult stem cells and stimulating their self-renewal and survival. The native human WNT3A 352 amino acid polypeptide is post-translationally modified by glycosylation and palmitoylation. The hydrophobic polypeptide can be difficult to purify to homogeneity at scalable levels.

As described herein and illustrated in FIG. 1, Human WNT3A is secreted from CHO cells and purified using an ion exchange (blue sepharose) column. Following purification, recombinant Human WNT3A is reconstituted into lipid vesicles consisting of DMPC and cholesterol. Sucrose density gradient data demonstrates a physical association between WNT3A and the liposome. Further, the liposomal Human Wnt3a polypeptide (L-WNT3A) can be stable under physiologic, aqueous conditions. In some instances, the formation of a liposomal structure is not a prerequisite for this interaction. In some instances, lipids with random structural characteristics are capable of interacting with Human WNT3A and stabilizing the polypeptide in an aqueous environment.

In some aspects, a L-WNT3A formulation is to be used in an investigational new drug (IND) Phase I study to treat bone defects in patients at high risk for delayed bone healing. In some instances, autologous bone graft material (BGM) is harvested, treated with L-WNT3A ex vivo, then washed and pelleted. In some cases, the resulting material, activated BGM (e.g., $BGM^{ACT}$), is considered as a drug product and is ready for immediate use. In some instances, L-WNT3A will not be directly administered to the patient but will be used to activate the autologous cells ex vivo. In some instances, for the initial stages of the program it is expected that the formulation will meet accepted U.S. Food and Drug Administration (FDA) criteria (purity, stability, etc.) for a systemically administered liposomal protein formulation.

Production of WNT3A from CHO Cells

Figure 9:
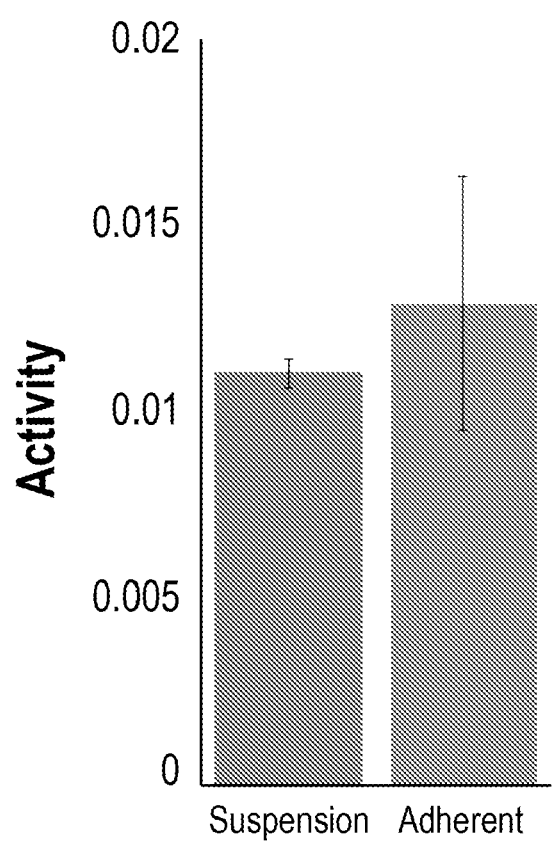
FIG. 9 exemplifies human Wnt3a polypeptide produced from cells grown in suspension versus adherent cultures.

Human WNT3A polypeptide was introduced into Chinese hamster ovary cell lines and was grown as adherent cells at temperatures ranging from 32-37° C. The CHO cells grown in suspension were tested to evaluate whether the CHO cells in suspension could secrete WNT3A efficiently (FIG. 9).

Figure 10:
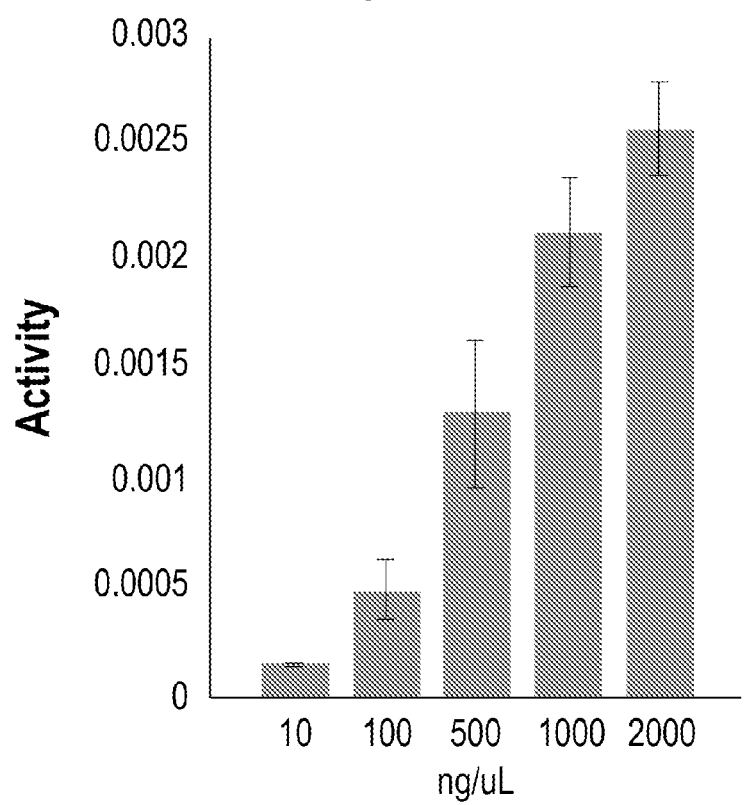
FIG. 10 illustrates doxycycline concentration-dependent induction of human Wnt3a polypeptide secretion. Doxycycline was added to the media at a range of concentrations (ng/uL), which influenced the amount of human Wnt3a produced by CHO cells.

WNT3A-transformed CHO cells were grown in DMEM plus Glutamax, antibiotics, and serum. The WNT3A plasmid was inducible; and a range of doxycycline concentrations was tested (FIG. 10). It was observed that doxycycline concentration could modulate the amount of Wnt3a secretion by CHO cells. Cells could be grown for up to 10 days, after which a new aliquot of cells was used.

Figure 11:
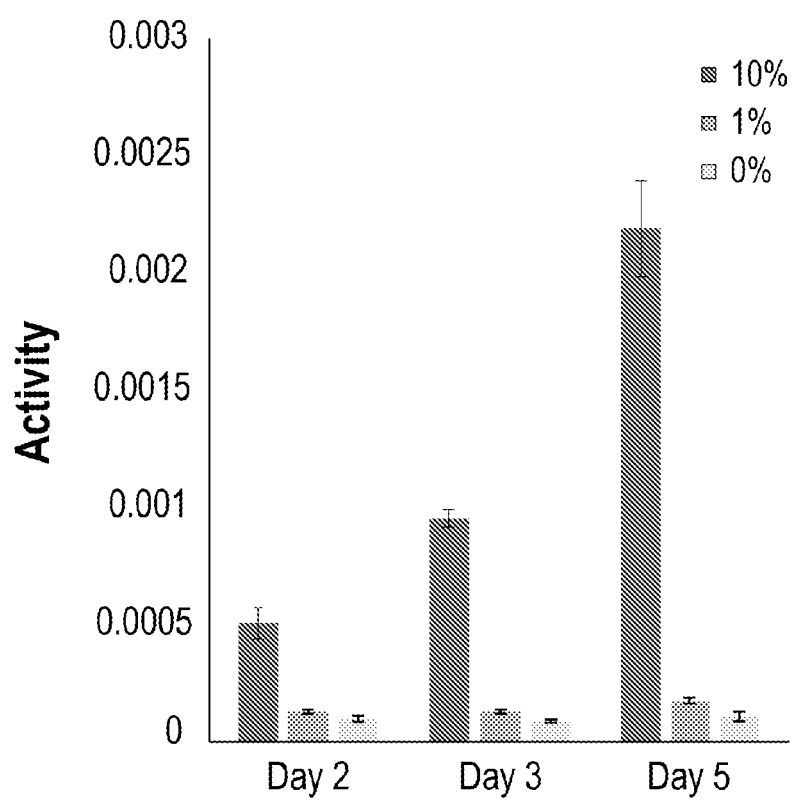
FIG. 11 exemplifies that fetal bovine serum was used for human Wnt3a polypeptide secretion from CHO cells.

Fetal bovine serum (FBS) was used for WNT3A secretion from CHO cells (FIG. 11).

Figure 12:
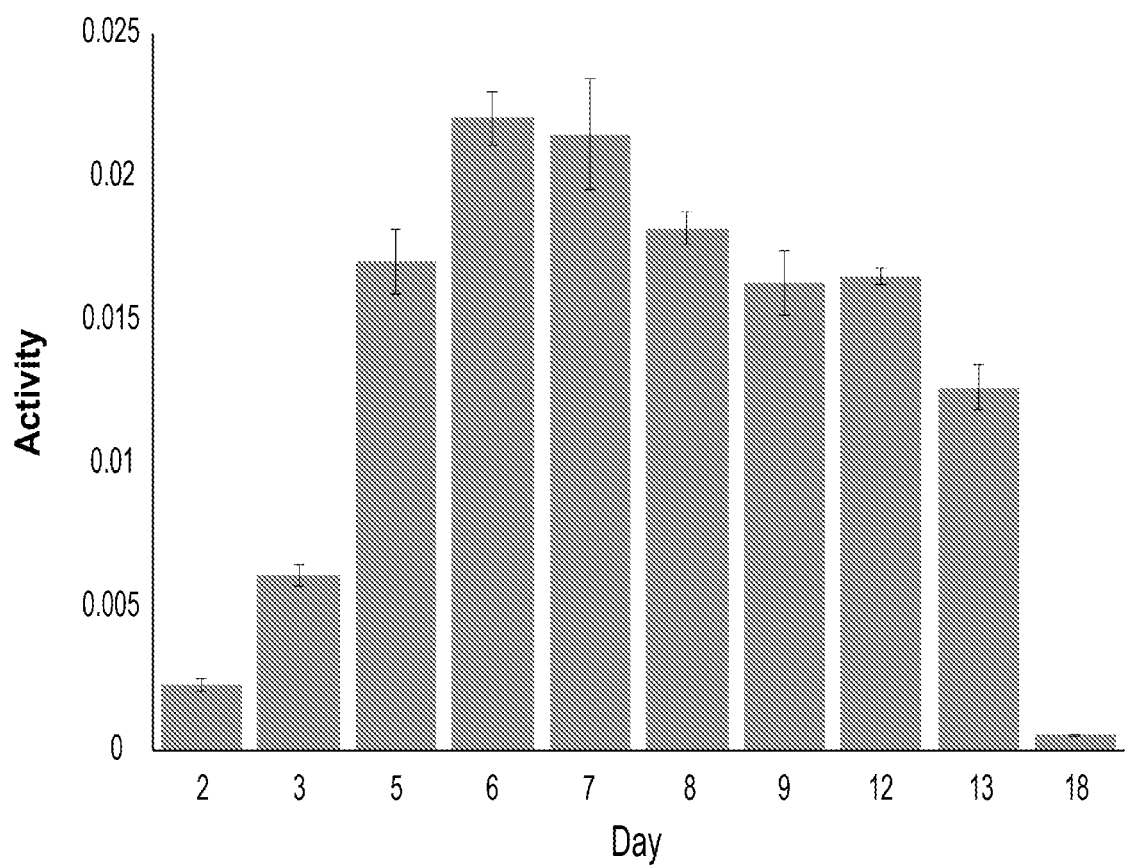
FIG. 12 illustrates human Wnt3a secretion from CHO cells as a function of days in culture.

Conditioned media (CM) from CHO cell cultures were collected, pooled, and stored at 4° C. up to 2 months without loss in activity (FIG. 12).

Prior to purification, the CM was filtered (0.22 micron filter) and 1% TritonX-100 was added. CM (40 mL) was applied to a blue Sepharose column (1.6 ml) equilibrated in 20 mM TrisCl pH 7.5 and 1% CHAPS. Flow-through was collected and the column was washed with 4 column volumes of 20 mM TrisCl pH 7.5, 1% CHAPS, 50 mM KCl. The column was washed again with 4 column volumes of 20 mM TrisCl pH 7.5, 1% CHAPS, 100 mM KCl. The column was then washed with 3 column volumes of 20 mM TrisCl pH 7.5, 1% CHAPS, 150 mM KCl; in which from this wash the human WNT3A was eluted. The column was washed again with 4 column volumes of 20 mM TrisCl pH 7.5, 1% CHAPS, 250 mM KCl. From a 40 mL CM, the yield was 12 µg of polypeptide at approximately 60% purity. Compared to other purification schemes, this method produced WNT3A with higher purity and higher yield. In some cases, the purity was 70%.

WNT3A Production and Liposome

WNT3A characterization. SDS-PAGE/Western blot. SDS PAGE and Coomassie blue staining analyses of WNT3A purification fractions were collected and analyzed for WNT3A polypeptide purity by 12% SDS polyacrylamide gel stained with Coomassie brilliant blue and silver nitrate (FIG. 2). Shown in FIG. 2, Purification fractions were collected and analyzed for WNT3A polypeptide purity by 12% SDS polyacrylamide gel stained with coomassie brilliant blue and silver nitrate. The estimated purity of WNT3A was 70%. Pierce 660 protein assay kit and absorbance at 280 nm were used to measure the total protein concentration. In each assay a BSA standard curve was generated to estimate the total protein concentration. WNT3A polypeptide concentration was determined using a quantitative Western blot and a WNT3A standard curve.

Figure 3:
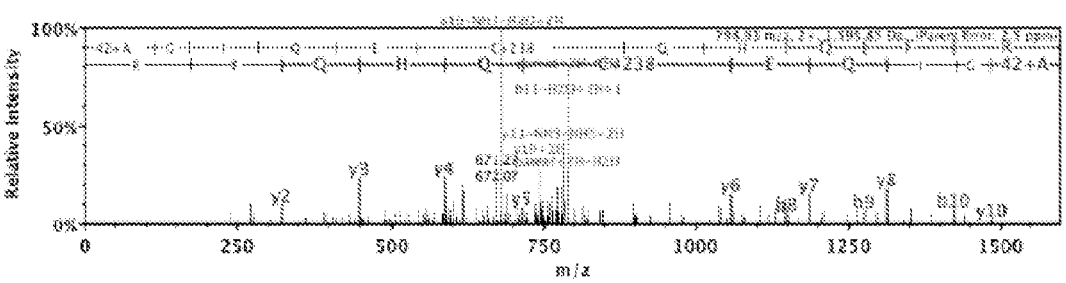
FIG. 3 exemplifies a mass spectroscopy data.

Mass spectroscopy. Mass spectrometry analysis verified that WNT3A polypeptide was lipidated and glycosylated (FIG. 3). The polypeptide was observed to be palmitoylated at S209.

Shown in FIG. 3, the method to prepare the WNT3A sample for mass spectroscopy was as follows. Polypeptide samples were precipitated using 4x volume of pre-chilled acetone at −80° C. The samples were stored at −80° C.

overnight followed by ultracentrifugation at 10,000 RPM 4° C. for 10 minutes. The supernatant was removed, and the polypeptide was reconstitution in solution containing 8M Urea and protease max (Promega). The samples were reduced with 5 mM DTT and incubated at 55° C. for 30 minutes. The samples were then allowed to cool to room temperature and then alkylated using acrylamide (15 mM) for 30 minutes at room temperature. Samples were then diluted with 50 mM ammonium bicarbonate, pH 8.0, to concentrations of <1M urea and 1 µg of trypsin protease (Promega) was added. The digestion was performed overnight at 37° C. The reaction was quenched by the addition of 50% formic acid, and the peptides were immediately cleaned and concentrated on a C18 micro-column (NEST group).

Liquid chromatograph and mass spectrometry (LCMS). Peptides were reconstituted in mobile phase A. A Waters NanoAcquity LC run at 300 nL/minute using gradients between 80 and 120 minutes in length was used. The analytical column was packed in house and was made with fused silica (75 uM ID) using PEEKE C18 3 uM matrix approximately 15 cm in length. A LTQ Orbitrap Velos mass spectrometer set in data dependent mode (DDA) was used to perform MSMS fragmentation on the intense precursor ions. CAD, HCD and ETD fragmentation techniques were used.

Database Searching and Analysis. The .RAW files from the mass spectrometer were searched against the Human Uniprot database using Sequest. Next a custom database containing the WNT3A sequence was created and searched, allowing for an array of variable modifications, not limited to STY phosphorylation, ST hexNac, ST Nac, STC palmitolyation etc. All Sequest searched files were uploaded into Scaffold (Proteome Software) for interrogation and semi-quantitative analysis.

In the case of the positive control (WNT3A protein purchased from StemRD), approximately 43% coverage was achieved. Sequence coverage and unique peptides are highlighted in yellow (FIG. 3A). The modified residues are shown in green. Palmitolyation modification was detected only on the C77 residue (FIG. 3B). In the case of purified WNT3A, ~51% coverage was achieved. Sequence coverage and unique peptides are highlighted in yellow (FIG. 3C). The modified residues are shown in green. Palmitolyation modification was detected on the S211 residue (FIG. 3C,D) and probable myristoleylation modification was detected on residues S139 and S181.

L-WNT3A Formulation and Characterization.

Liposomal Wnt3a (L-Wnt3a) polypeptides containing net positive, negative, or neutral charges were manufactured by incubating either positive charged lipids, negatively charged lipids, or neutral charged lipids at room temperature, with purified Wnt3a for at least about 6 h and up to about 24 h. The lipid to cholesterol ratio was maintained at 90:10. Following incubation, L-Wnt3a was separated from CHAPS and other impurities by centrifuging at force ranging from 16,000-150,000×g for up to 1 h at 4° C. The L-Wnt3a pellet was then resuspended in sterile 1×PBS, overlaid with nitrogen gas and stored at 4° C.

Figure 4:
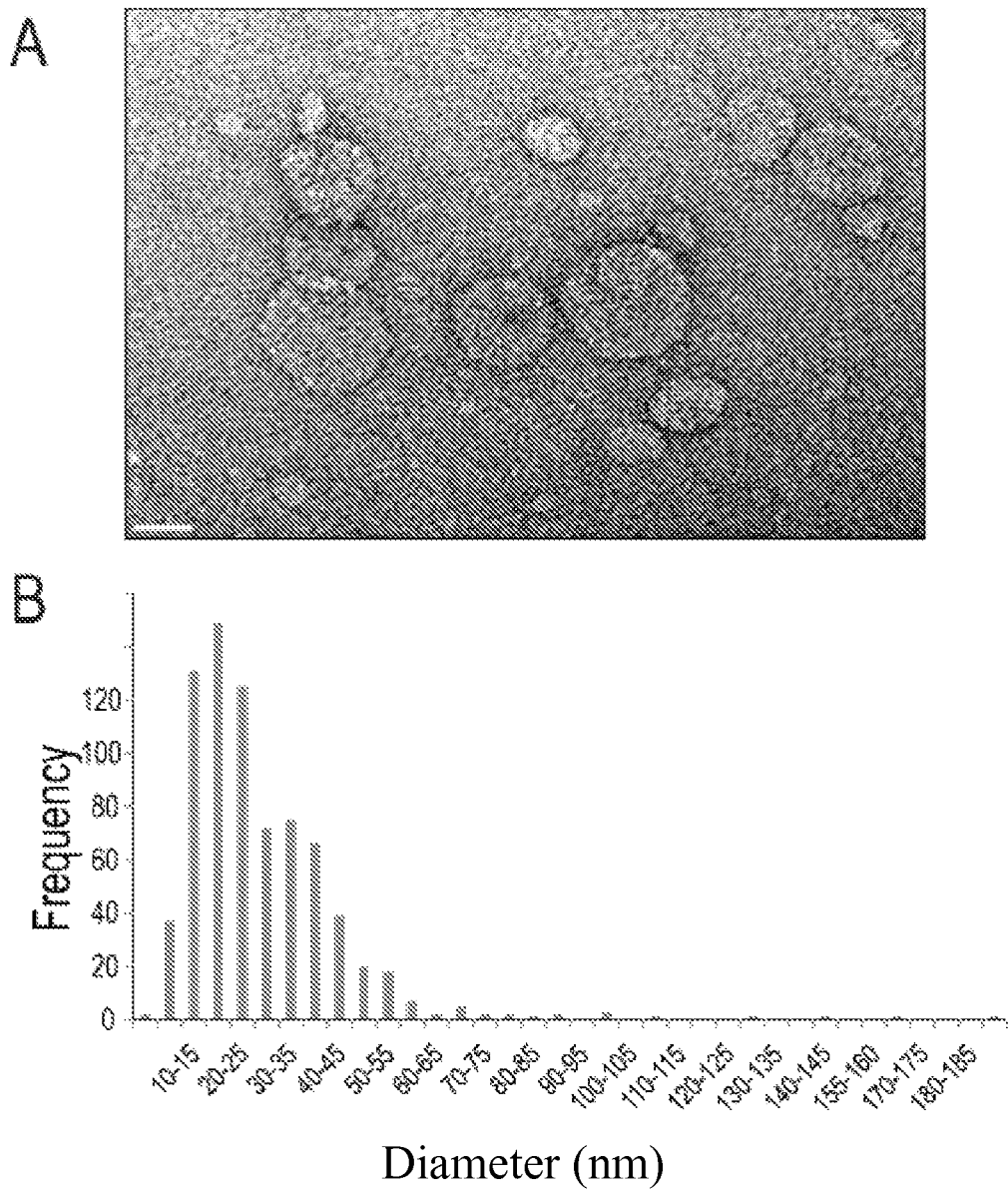
FIG. 4 illustrates TEM characterization of L-Wnt3a. TEM was used to visualize L-Wnt3a, and the average diameter of the vesicles was calculated.
Figure 15:
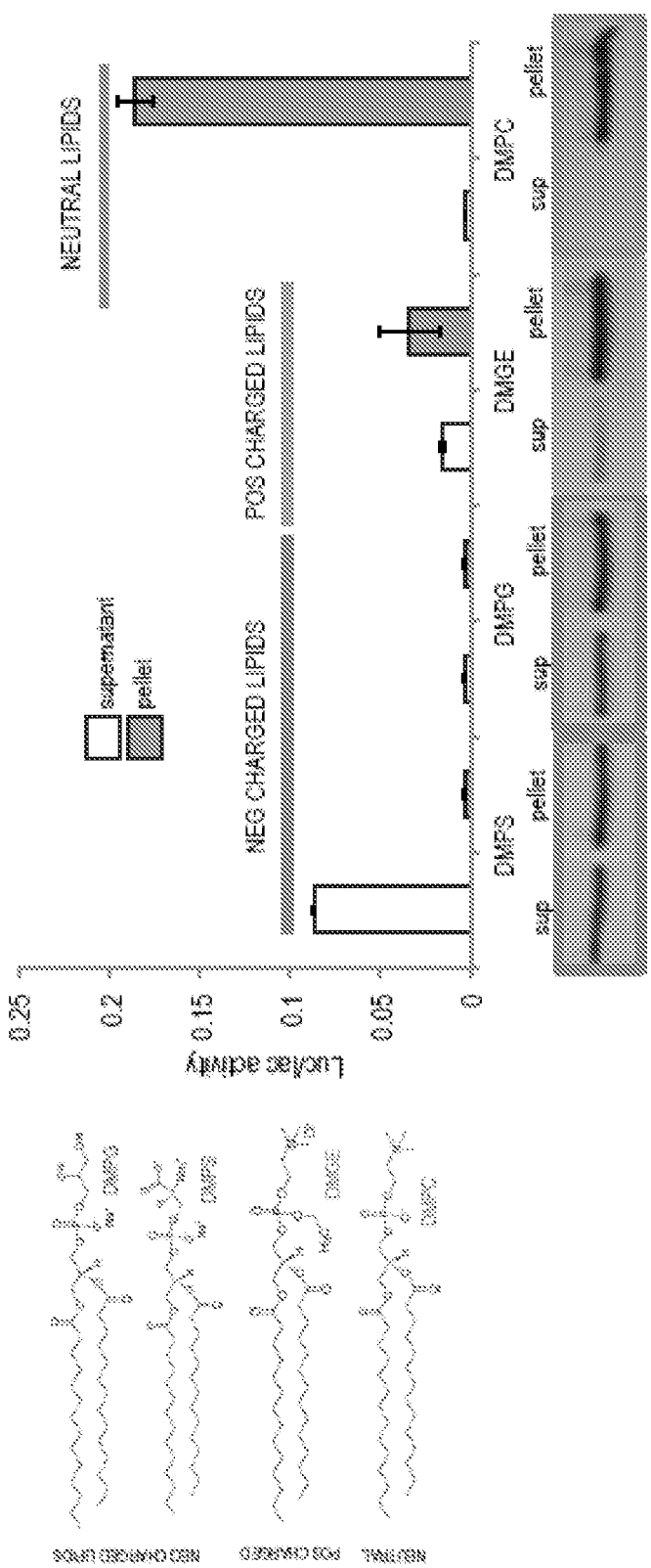
FIG. 15 illustrates human Wnt3a activity under different lipid formulations. DMPC and cholesterol lipids were substituted for CHAPS to maintain Wnt3a activity but liposomes fabricated with lipids such as MPPC, DPPC, DMPS, DMPG, and DMGE were inactive.

Lipid interactions with WNT3A. When combined with lipids of various carbon chain lengths, WNT3A demonstrated a functionally relevant interaction with uncharged lipids (FIG. 15). These data suggest that it was primarily a hydrophobic interaction that mediated the association between the WNT3A polypeptide and the liposome (FIG. 4).

TEM characterization of L-WNT3A. TEM was used to visualize the range of diameters observed for L-WNT3A (FIG. 4). The appearance and size of the L-WNT3A fall within the size range reported for exosomes e.g., 20-100 nM. See also Dhamdhere et al. (2014) PLoS ONE 9(1): e83650, herein specifically incorporated by reference in its entirety.

Mouse LSL cell-based assay. Mouse LSL cells were stably transfected with a Wnt-responsive luciferase reporter plasmid pSuperTOPFlash (Addgene) and a constitutive LacZ expression construct pEF/Myc/His/LacZ (Invitrogen) for normalizing beta galactosidase activity to cell number. Human embryonic kidney epithelial (HEK293T) cells were stably transfected with the above two plasmids. Cells (50000 cells/well, 96-well plate) were treated with L-WNT3A in DMEM supplemented with 10% FBS (Gibco) and 1% P/S (Cellgro) at a concentration of 10 uL in 150 uL total volume, unless otherwise stated. Included also was a serial dilution of purified WNT3A polypeptide.

Figure 5:
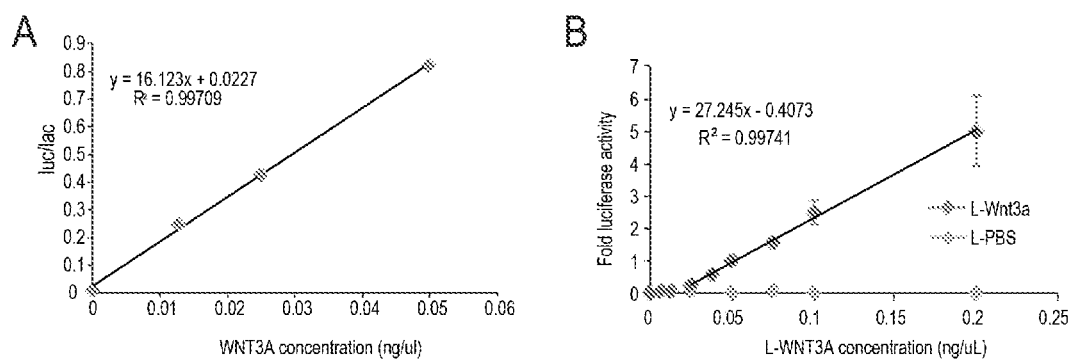
FIG. 5 illustrates quantification of human Wnt3a and L-Wnt3a activities. Bioluminescence was quantified with triplicate reads on a dual-light ready luminometer (Berthold). Activity of Human Wnt3a (ng/uL; A) and L-Wnt3a was defined (B) from a standard curve generated by serial dilutions of Wnt3a protein.

Cells were incubated overnight at 37° C., 5% $CO_2$, then washed, lysed with Lysis Buffer (Applied Biosystems), and the luciferase and β-galactosidase expression levels quantified using a dual-light combined reporter gene assay system (Applied Biosysytems). Bioluminescence was quantified with triplicate reads on a dual light ready luminometer (Berthold). Activity of WNT3A (ng/uL) and L-WNT3A was defined from a standard curve generated by serial dilutions of WNT3A polypeptide (FIG. 5). In experiments involving a time course, WNT3A activity was expressed as percent activity. Percent activity was calculated as follows:

$$\% \text{ activity} = \frac{\left(\frac{luc}{lac}\right)tn}{\left(\frac{luc}{lac}\right)t0} * 100$$

Summary of Stability Data

Figure 6:
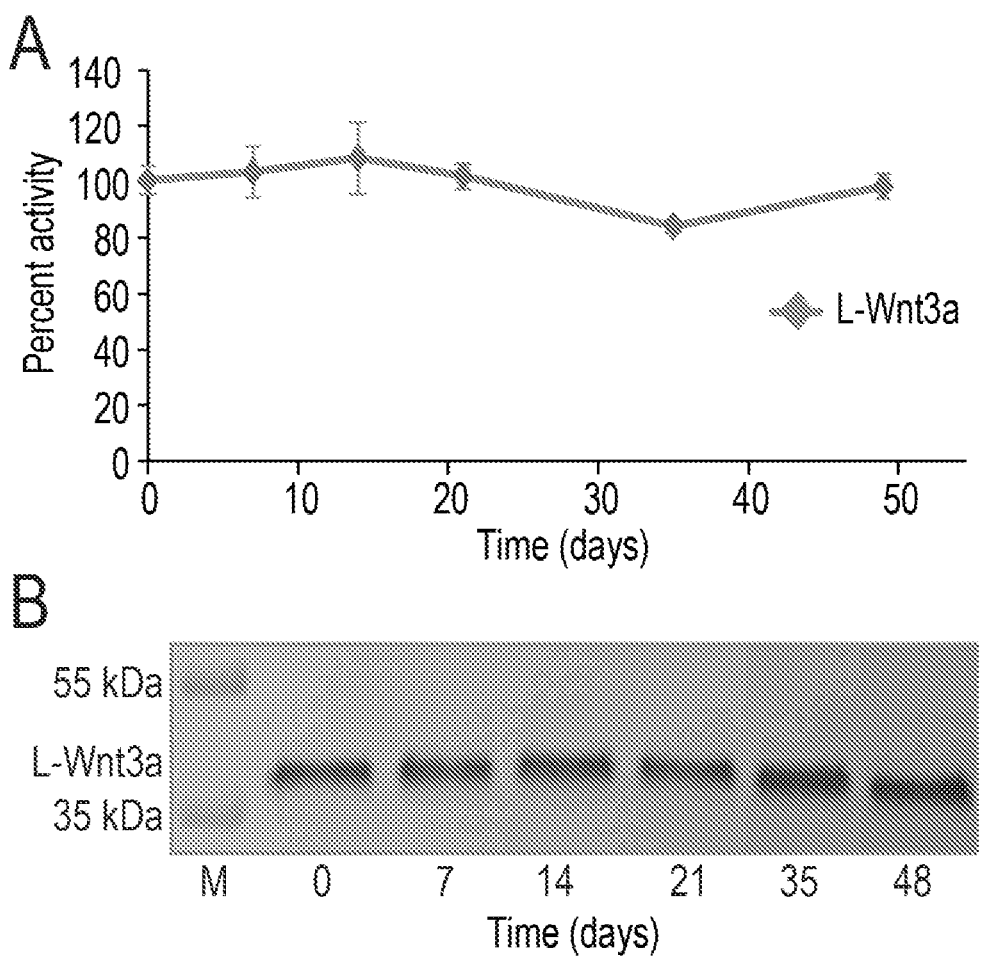
FIG. 6 indicates the stability of L-Wnt3a at 4° C. The liposome-Wnt3a interaction was examined. Liposomal Wnt3a (L-Wnt3a) was incubated at 4° C. for up to 48 days. Human L-Wnt3a polypeptide was then tested in a LSL assay for activity. L-Wnt3a polypeptide showed no loss of activity over the 48-day test period.
Figure 7:
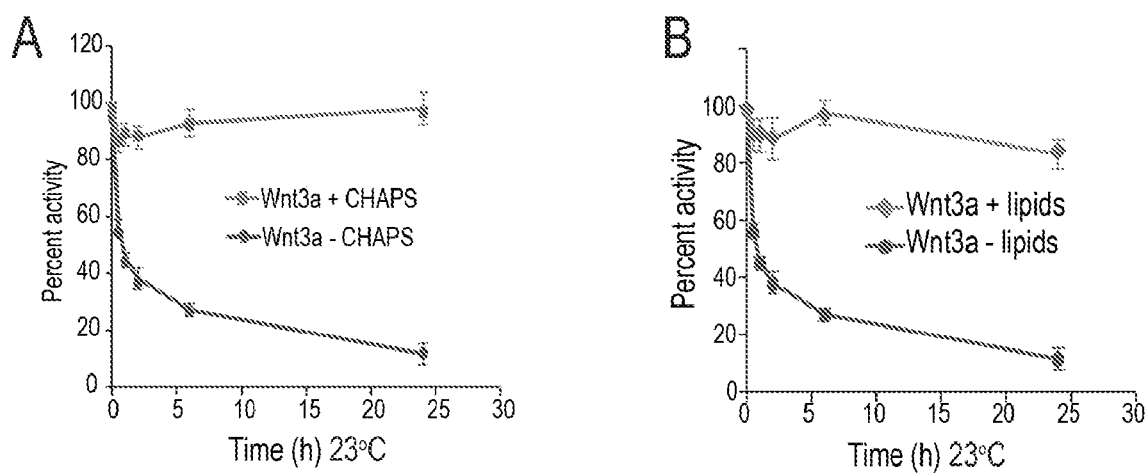
FIG. 7 indicates the stability of L-Wnt3a at 23° C.

Based on the LSL reporter cell assay and PAGE-Western blot analyses, conditioned media from fermentation was stable at 4° C. for a minimum of 2 months. Based on the LSL reporter cell assay and PAGE-Western blot analyses, L-WNT3A was stable at 4° C. for >106 days (FIG. 6). Based on the LSL reporter cell assay and PAGE-Western blot analyses, at 23° C. L-WNT3A had a half-life of >48 hours (blue line, FIG. 7). Compare to naked WNT3A polypeptide, which lost its activity within 5 min at 23° C.

Figure 8:
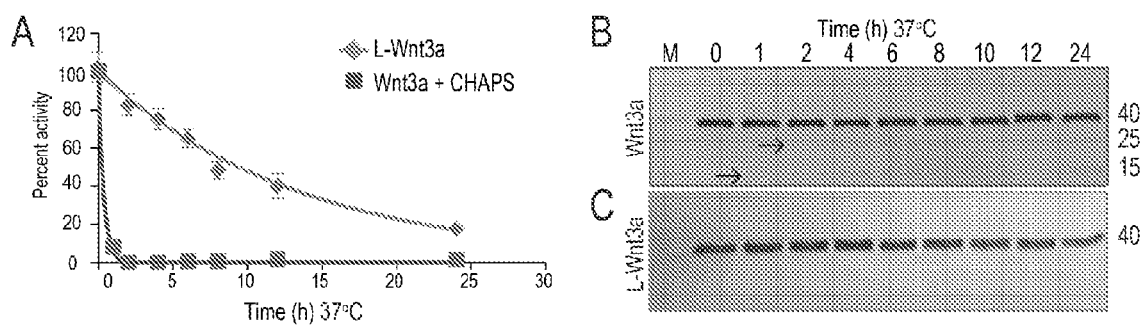
FIG. 8 illustrates the stability of L-Wnt3a at 37° C. The association of human Wnt3a with a DMPC:cholesterol liposome was tested to determine whether it would provide stability to Wnt3a polypeptide. Data from multiple time points were fit to a single exponential decay, which showed that after 10 h, L-Wnt3a retained half of its activity at 37° C. (blue line, FIG. 8A) whereas Wnt3a lost its activity within 5 min (red line, FIG. 8A). The loss of activity in human Wnt3a was due to proteolysis. In Wnt3a+CHAPS solutions, smaller molecular weight bands were detectable in the immunoblots (FIG. 8B). An immunoblot of L-Wnt3a preparations did not detect smaller molecular weight bands corresponding to Wnt3a (FIG. 8C).

Based on the LSL reporter cell assay and PAGE-Western blot analyses, at 37° C. L-WNT3A had a half-life of 10.5 hours (blue line, FIG. 8). Note that even if a detergent (CHAPS) was added to stabilize the hydrophobic polypeptide, WNT3A lost its activity within 5 min (red line, FIG. 8).

Characterization of the WNT Cellular Reporter Assay

The LSL reporter cell line was used to assess activity of Wnt polypeptides and agonists. The following characterizations of L-WNT3A were made using the following reporter assay. Cells were plated at $5.0 \times 10^4$ per assay well and the activity of WNT3A and L-WNT3A were quantified using LSL and HEK293 reporter lines. Under these conditions, WNT3A and L-WNT3A showed similar ability to activate Wnt signaling (FIG. 13).

Figure 14:
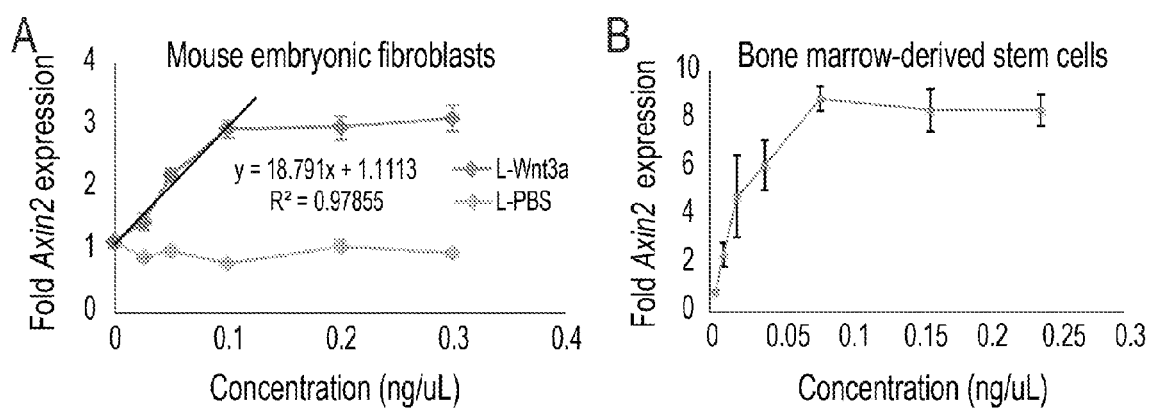
FIG. 14 illustrates L-Wnt3a dose response curves using primary cells. (A) In mouse embryonic fibroblasts (MEFs), the linear range of effective concentration was 0.025-0.1 ng/µL human Wnt3a. (B) L-Wnt3a activity in bone marrow-derived stem cells, and determined that the linear range of effective concentrations ranged from 0.004-0.08 ng/µL.

Precision and limit of detection: The assay's sensitivity is $R^2 = 0.99$. In FIG. 14A and FIG. 14B, WNT was shown to reach an optimal concentration of 0.1 ng/μL. The assay's cutoff points were 0.025 ng/μL and 0.2 ng/μL. The LSL assay was unaffected by deliberate variations in WNT3A concentration (FIG. 14C). A range of WNT3A concentrations demonstrated a proportionate luciferase response over time, which indicated the reliability of the assay.

The specificity was demonstrated using the Wnt polypeptide agonist R-spondin2, which synergized with WNT polypeptides to activate the WNT pathway. Assay specificity was also demonstrated using WNT5A, which in the presence of the Wnt co-receptor Ror2 represses beta catenin mediated activation of the pathway. As shown in FIG. 13D, neither reagent demonstrated activity in the LSL reporter assay.

Figure 13:
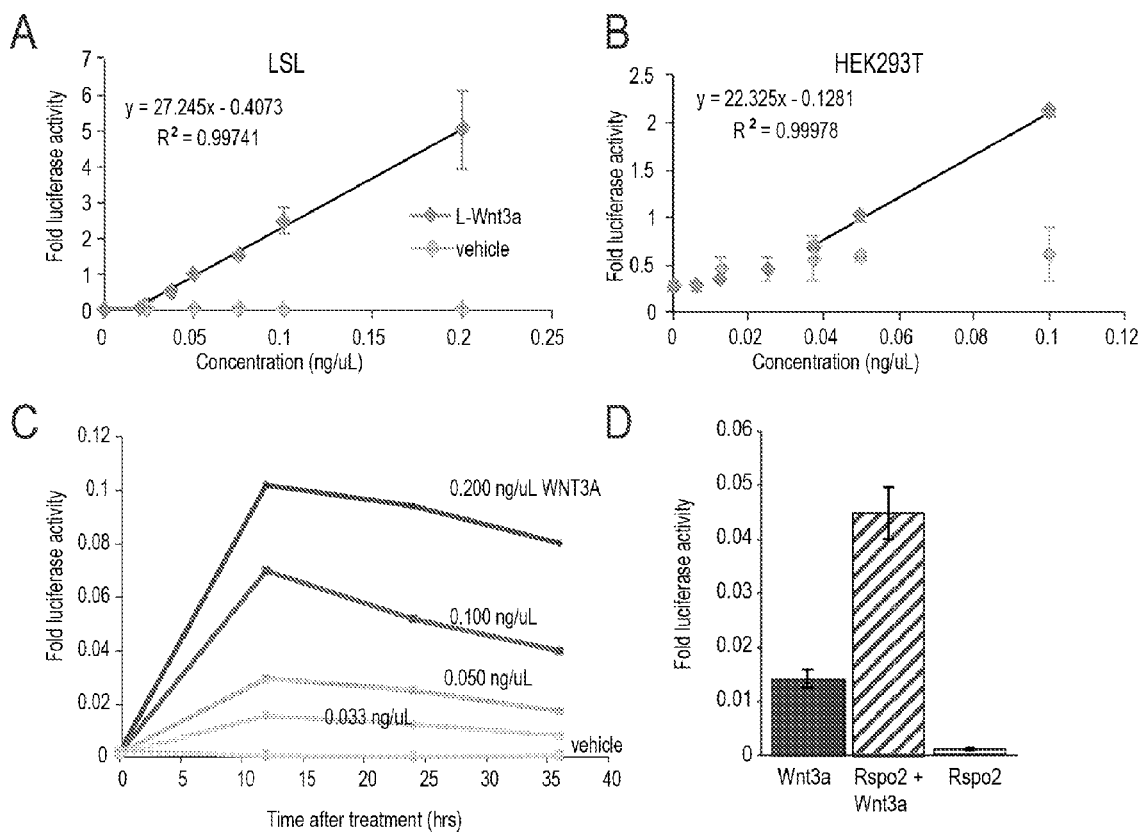
FIG. 13 illustrates robustness, precision, limit of detection and specificity of the LSL cellular reporter assay.

As shown in FIG. 13(A,B), cells were plated at $5.0 \times 10^4$ per assay well and the WNT3A and L-WNT3A activities were both quantified. Under these conditions, both WNT3A and L-WNT3A showed similar ability to activate Wnt signaling. The assay's sensitivity is $R2=0.99$. Purified human WNT3A polypeptide was used as a positive control. (C) The LSL assay was unaffected by deliberate variations in WNT3A concentration. The data from a range of concentrations demonstrated a proportionate luciferase response over time which provided an indication of the reliability of the assay. (D) Specificity was demonstrated by addition of Rspo2 in the presence and absence of WNT3A.

Accuracy: the assay had an intra- and inter-assay coefficient of variation of 17.2%.

L-WNT3A Dose Response Curves Using Primary MEFs

LSL and HEK293T cells were engineered to be sensitive to Wnt and Wnt agonists and therefore provide little meaningful data on the relationship between dose, drug effect, and clinical response. To more closely mimic the in vivo cellular response to a Wnt stimulus, mouse embryonic fibroblasts (MEFs) was assayed using expression of the Wnt target gene Axin2 as a measure of pathway activity.

In primary cells the linear range of effective concentration was 0.025-0.1 ng/μL WNT3A (FIG. 14A). L-WNT3A activity was also assayed in bone marrow-derived stem cells, and found the linear range of effective concentrations ranged from 0.004-0.08 ng/μL (FIG. 14B). Thus, primary cell populations exhibited significantly different sensitivities to a Wnt stimulus.

Select lipids can substitute for CHAPS to maintain WNT3A. DMPC and cholesterol lipids could substitute for CHAPS to maintain WNT3A activity. Liposomes fabricated with other lipids, such as for example MPPC, DPPC, DMPS, DMPG, and DMGE, were inactive (FIG. 15).

Lipid Reconstitution of WNT3A

Many proteins denature at high temperatures, and avoiding such denaturation at body temperature is a key to extending the duration of a protein therapeutic. Liposomal packaging preserved the biological activity of Wnt3a and that this formulation can have efficacy in multiple bone injury applications. The affinity of Wnt3a for the liposome and the stability of this association were characterized. The kinetics and dynamics of Wnt pathway activation by L-WNT3A were demonstrated.

Figure 16:
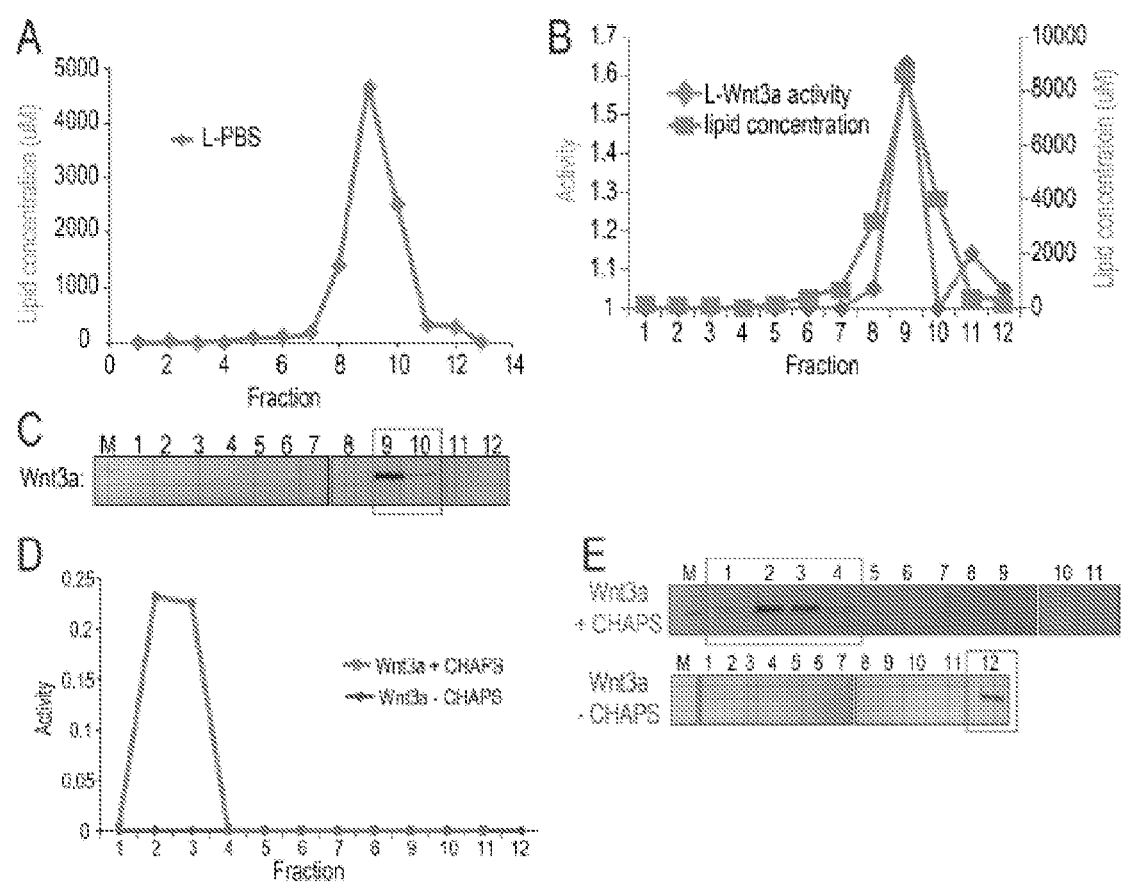
FIG. 16 exemplifies a sucrose density gradient.

Affinity between WNT3A and liposomes. Sucrose density gradient data demonstrated a physical association between WNT3A polypeptide and the lipids (FIG. 16). The sucrose density gradient in FIG. 16 demonstrated a physical association between WNT3A and lipids. WNT3A polypeptide (FIG. 16A) localized to a high-density fraction and this high-density fraction further showed WNT activity (FIG. 16B). Western analyses demonstrated that the majority of WNT3A polypeptide was localized to this high-density fraction (FIG. 16C). The phospholipid assay demonstrated that this high-density fraction contained the majority of the lipids (orange line, FIG. 16B). Thus when compared with WNT3A alone (which segregated in low-density fractions 2-3, FIG. 16D,E) L-WNT3A shifted to a high-density fraction, which demonstrated a physical association and not as an aggregation between WNT3A and the liposome.

Figure 17:
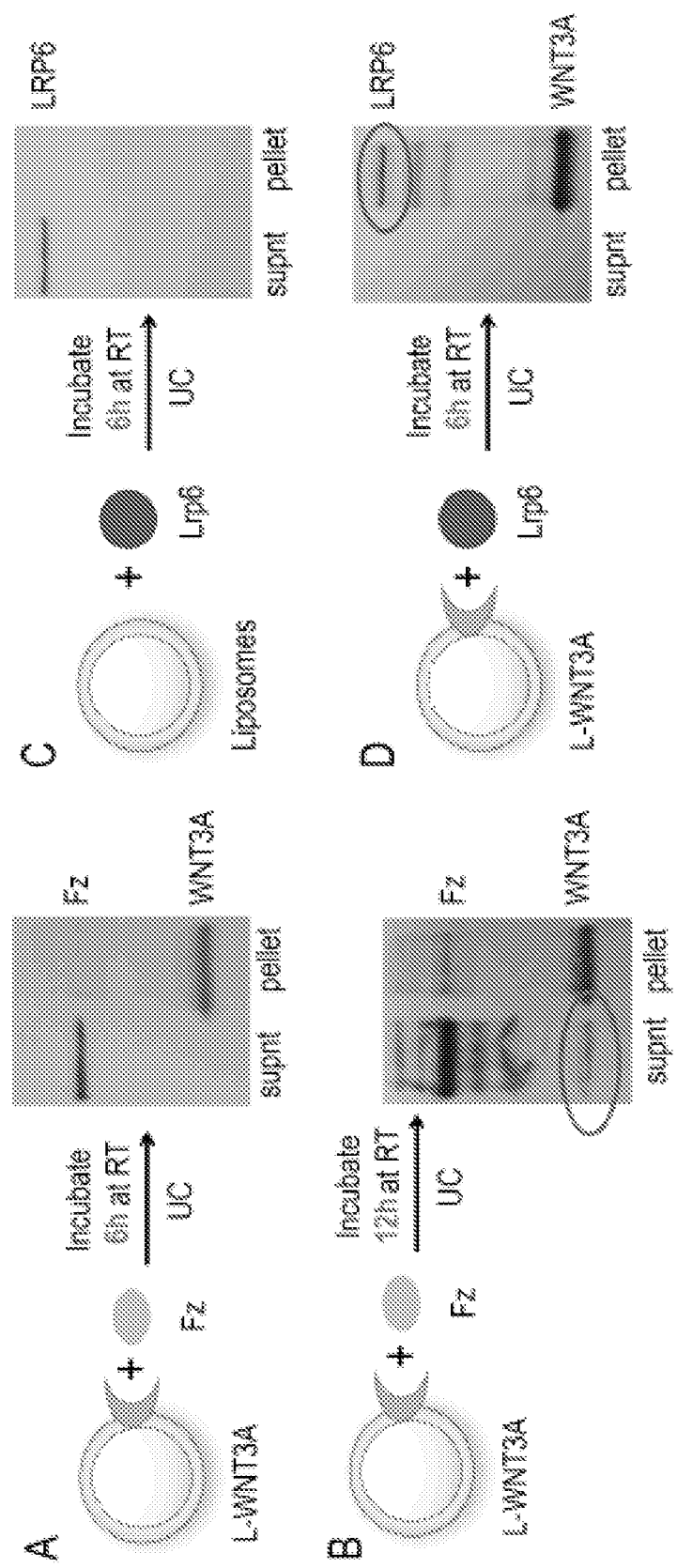
FIG. 17 exemplifies human Wnt3a affinity toward liposome membranes. The Wnt3a/Frizzled binding affinity was about 3.6 nM. The Wnt3a/LRP6 binding affinity was about 9 nM. The binding affinity between Wnt3a and the liposomal membrane was about ~6 nM, based on pull-down assays between Wnt3a, Frizzled (Fz), and Lrp6.

Affinity estimates between Wnt3a and liposomes. The Wnt3a/Frizzled binding affinity was about 3.6 nM. The Wnt3a/liposome binding affinity was about 9 nM. In a competition assay between L-Wnt3a and Frizzled, Wnt3a was observed in the liposomal pellet (FIG. 17A). After further incubation, Wnt3a dissociated from the liposome pellet and preferentially associated with Frizzled in the supernatant (FIG. 17B). Thus the affinity of Wnt3a for the liposomal membrane was lower than the affinity of Wnt3a for Frizzled.

In a second competition assay between liposomes and LRP6, LRP6 was observed in the supernatant (FIG. 17C). When LRP6 was incubated in the presence of L-Wnt3a, the LRP6 protein migrated from the supernatant (FIG. 17C) to the L-Wnt3a pellet (FIG. 17D).

Conclusion: Based on these pull-down assays the binding affinity between Wnt3a and the liposomal membrane was estimated to be about 6 nM. These assays also demonstrated that Wnt3a reconstituted in a liposomal membrane was positioned in such a way that it could interact with its receptors Frizzled and LRP6.

Kinetics of WNT3A Association with Liposomes

Figure 18:
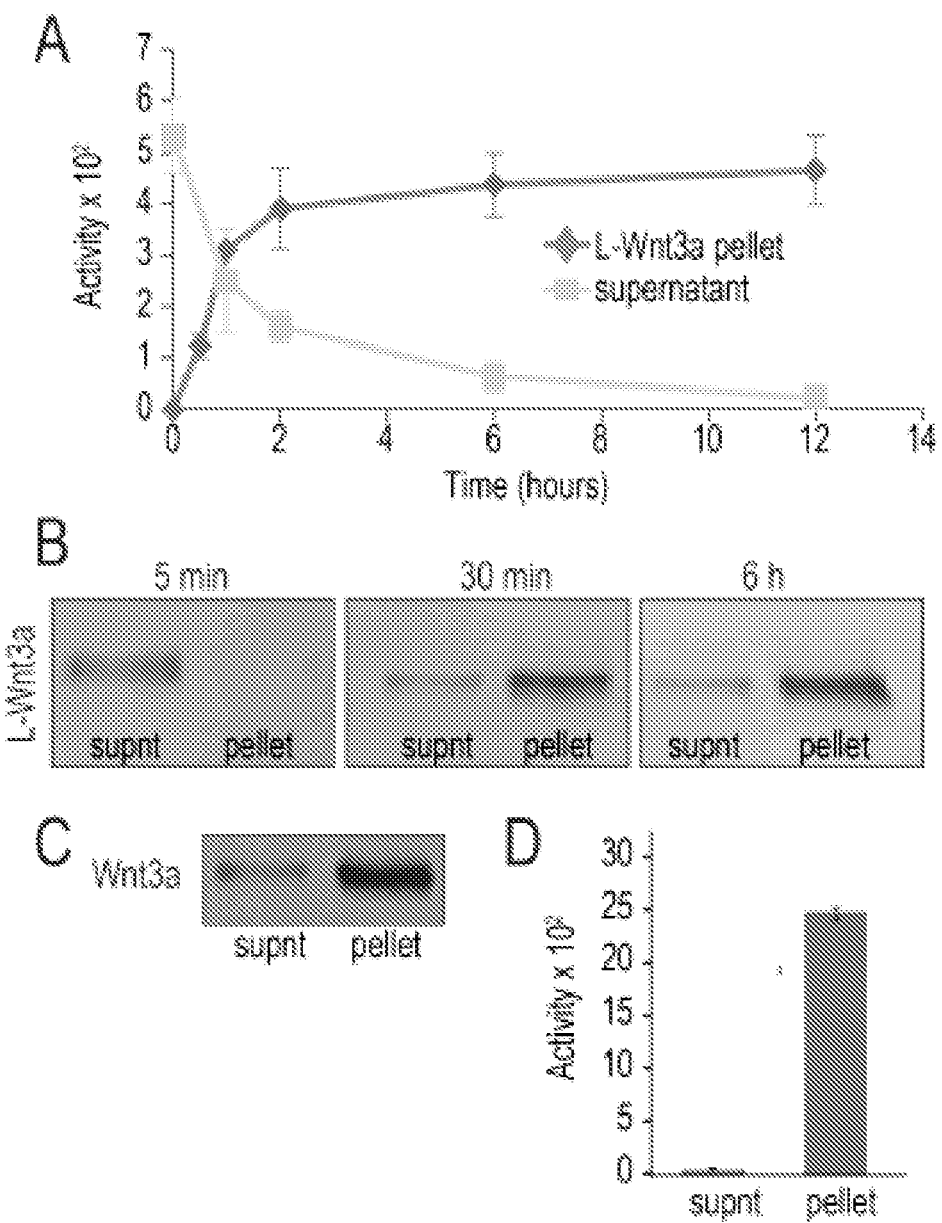
FIG. 18 illustrates kinetics of human Wnt3a association with liposomes.

Based on the LSL reporter cell assay and PAGE-Western blot analyses, Wnt3a rapidly associated with the liposome and this association was responsible for maintaining the polypeptide's activity. Initially, Wnt3a activity was observed in the supernatant. Over the course of about 30 minutes, Wnt3a polypeptide transferred from the supernatant to the pellet at a rate of about $3 \times 10^{-3}$ nM/sec (FIG. 18A). By 6 h, 90% of the Wnt3a activity was observed in the pellet. Similarly, western blot analysis showed that 90% of the polypeptide were found in the pellet (FIG. 18B). After 24 h at 23° C., liposomes were separated from the aqueous supernatant by centrifugation. No visible polypeptide precipitation was observed in the pellet. Western blot demonstrated that the majority of Wnt3a was in the liposomal pellet (FIG. 18C). FIG. 18D shows the Wnt3a activity in the supernatant and the pellet at the end of the experiment.

Figure 19:
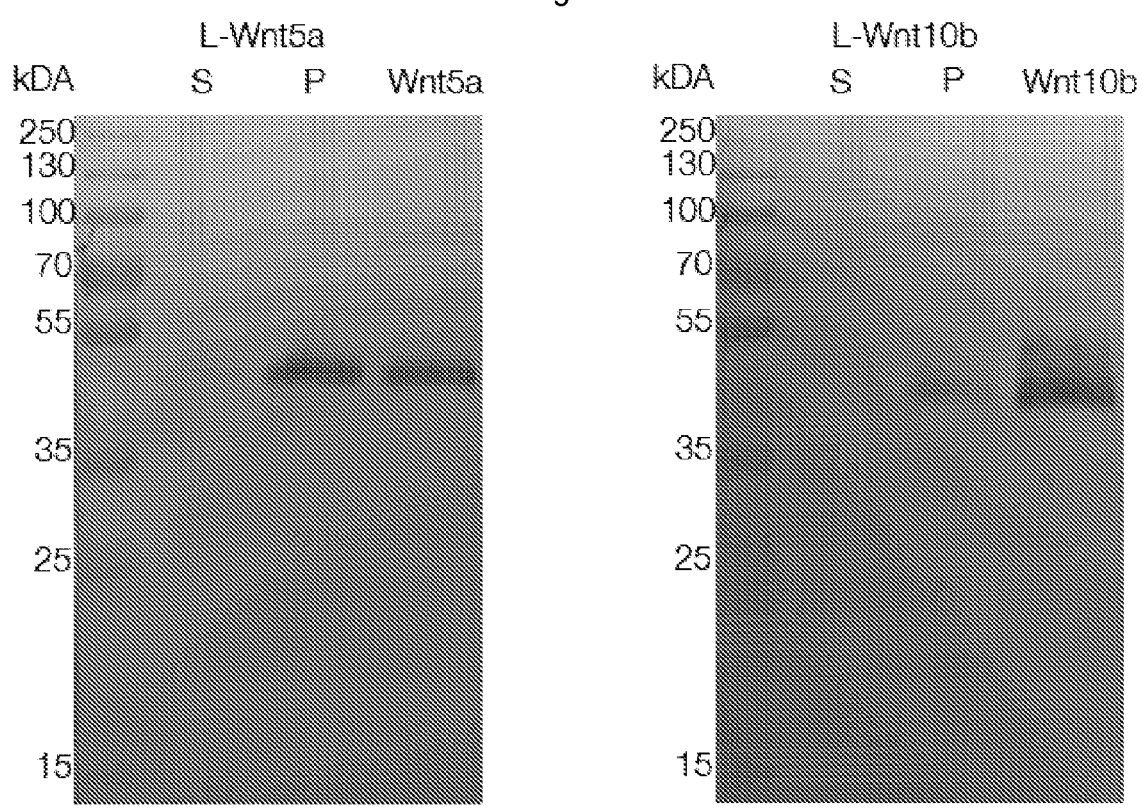
FIG. 19 illustrates Wnt5a and Wnt10b polypeptide bindings to neutral DMPC liposomes.

FIG. 19 illustrates Wnt5a and Wnt10b interactions with liposomes (FIG. 19).

Scale up experiment. Cells from the freezer stock were seeded onto a 15 cm tissue culture plate. After incubation at 37° C., 5% $CO_2$ for 3-4 days the cells were expanded 1:5 into 2×15 cm plates for 4 days. These cells were further expanded 1:5 into 20×15 cm plates. After 24 hours of incubation the cells were induced with doxycycline. CM was collected every 24 hours and stored at 4° C. Activity of the CM was measured to confirm WNT3A secretion. 1% TritonX was added to 1 L CM and filtered through a 0.22 μm filter. CM was then loaded onto a 150 ml blue sepharose column. From this trial 80 μg of WNT3A was eluted in a gradient of KCl, resulting in 40% overall yield.

Materials and Suppliers
CHO cells: Invitrogen
Plasmid vector: Promega
Lipids: Avanti Polar Lipids
Blue sepharose purification column:
WNT3A standard: Stem R&D
LSL cells:
Ultracentrifuge:
Abbreviations
BGM: bone graft material
BGM$^{ACT}$: L-WNT3A activated bone graft material
CHO: Chinese Hamster Ovary
CM: Conditioned media
Fz: Frizzled, the WNT receptor
HEK: Human embryonic kidney
LSL: mouse L cells
L-WNT3A: liposomal WNT3A
MEF: Mouse embryonic fibroblast Example 2

Human Wnt3a polypeptide was produced by transfection of a genetically engineered Chinese hamster ovary (CHO) cell line with a plasmid carrying human Wnt3a nucleic acid. A lipofectin-based transfection method was used. The plasmid was under the control of a doxycycline-inducible promoter. The Wnt3a-transformed CHO cells were grown in adherent or suspension culture in a culture medium containing DMEM (Dulbecco's Modified Eagle Medium)+10% fetal bovine serum (FBS), GlutaMax™ (a glutamine-based dipeptide), antibiotic (e.g. doxycycline), G418, non-essential amino acids, blasticidine and serum, and at temperatures ranging from about 32-37° C. The amount of Wnt3a secreted from CHO cells depended on whether they were grown as adherent or suspended cultures. Doxycycline was added to the media at a range of concentrations, which could modulate the amount of human Wnt3a produced by CHO cells. The culture medium included Fetal bovine serum (FBS) which was present throughout the culture period during which the CHO cells secreted Wnt3a. Cells can be grown for up to 10 days, after which a new aliquot of cells was used.

Compared to a purification scheme using either a continuous gradient or a gel filtration, the present purification scheme uses a step gradient, which produces higher purity and higher yield as shown in Tables 1 and 2. In the purification scheme that uses either a continuous gradient or a gel filtration, the continuous salt gradient was run on a blue Sepharose column from 150 mM to 1.5 M NaCl, followed by gel filtration and a heparin sulfate column. In some instances, as described elsewhere herein, the present scheme also utilizes a hydrophobic purification step such as a hydrophobic column (e.g. a Protein A-Sepharose column).

Table 1 shows results obtained by the purification step of the present invention and Table 2 shows results obtained by the purification scheme using either a continuous gradient or a gel filtration purification step.

TABLE 1

| Fraction | Volume | Protein conc (ug/ml) | Total protein (mg) | Wnt3a protein (ug) | Fold purification | % Yield |
|---|---|---|---|---|---|---|
| Conditioned media | 40 ml | 3714 | 148.560 | 20 | | 100 |
| Anion exchange (Blue Sepharose) | 6 ml | 64 | 0.384 | 12 | | 60 |

TABLE 2

| Fraction | Volume | Protein conc (ug/ml) | Total protein (mg) | Wnt3a protein (ug) | Fold purification | % Yield |
|---|---|---|---|---|---|---|
| Conditioned media | 350 ml | 3714 | 1,299.900 | 175 | — | 100 |
| Anion exchange (Blue Sepharose) | 120 ml | 54 | 6.480 | 60 | | 34.2 |
| Gel filtration (Superdex 200) | 30 ml | 70.6 | 2.118 | 7.5 | | 4.2 |

Example 3

Animals

All procedures followed protocols approved by the Stanford Committee on Animal Research. Beta-actin-enhanced green fluorescent protein (ACTB-eGFP; The Jackson Laboratory, Sacramento, Calif.) and CD1 wild type, syngeneic mice were used. Mice <3 months old were considered young; mice >10 months were considered aged. Axin2$^{CreERT/+}$ and R26R$^{mTmG/+}$ mice were purchased from Jackson Labs. Aged wild type Lewis rats ("retired breeders" from Charles Rivers, Mass.), were utilized for spinal fusion surgeries according to AAUC and IUPAC guidelines.

Collection and Treatment of Bone Graft Material (BGM) for Rodent Models

Figure 20:
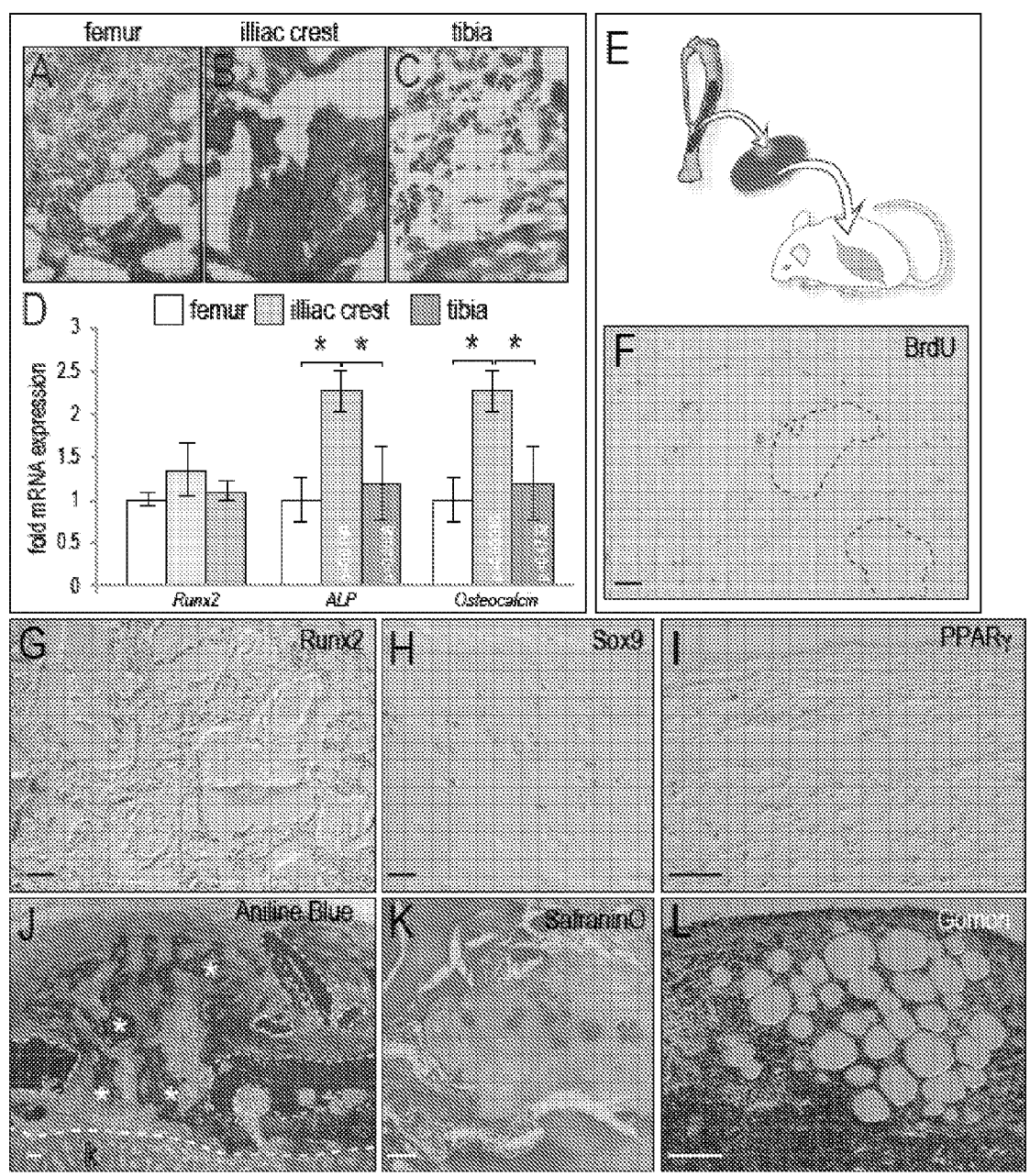
FIG. 20 illustrates individual components of the bone graft material. The bone graft material contains stem and progenitor cell populations.
Figure 21:
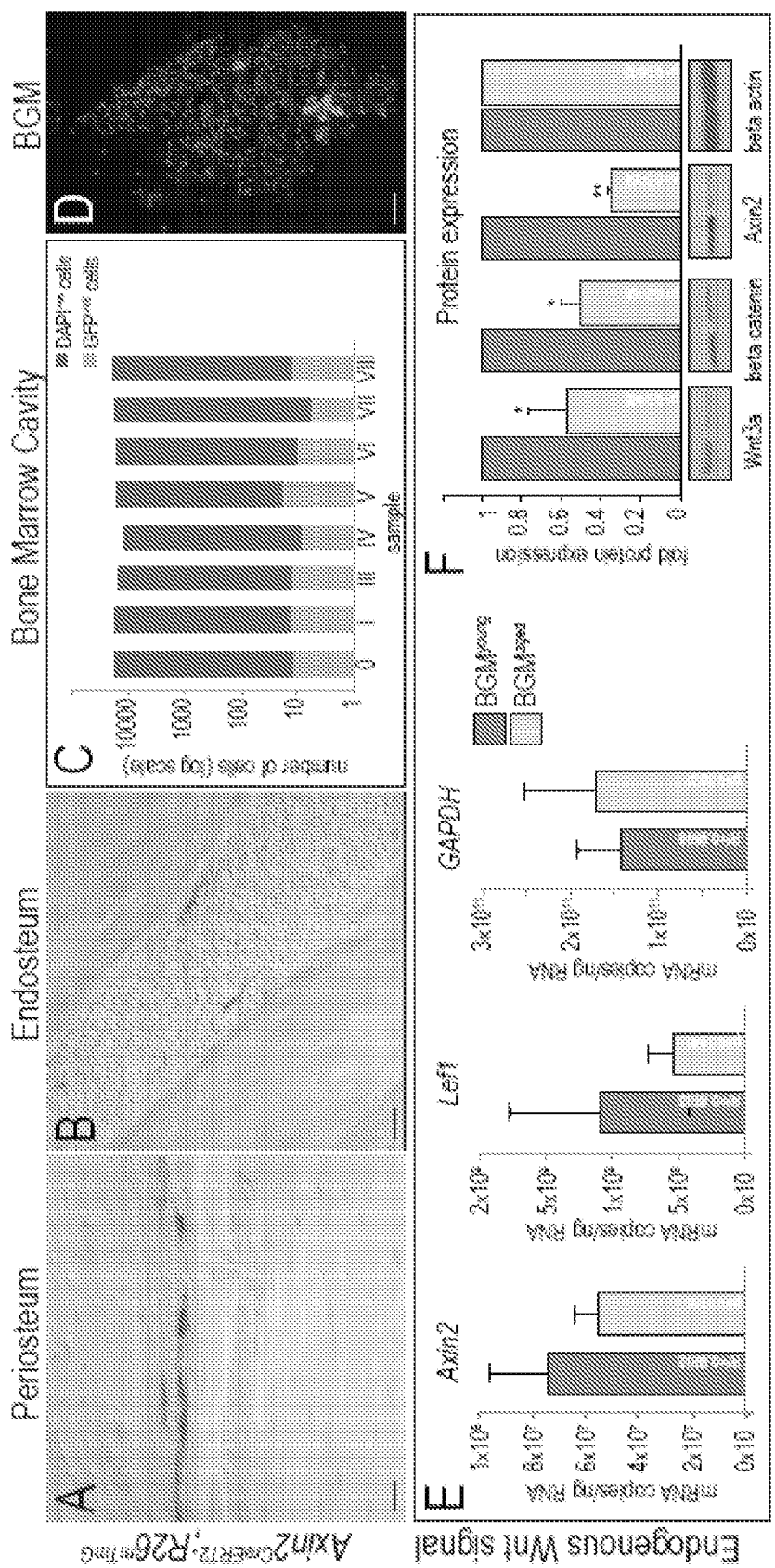
FIG. 21 illustrates bone graft material as Wnt responsive.
Figure 22:
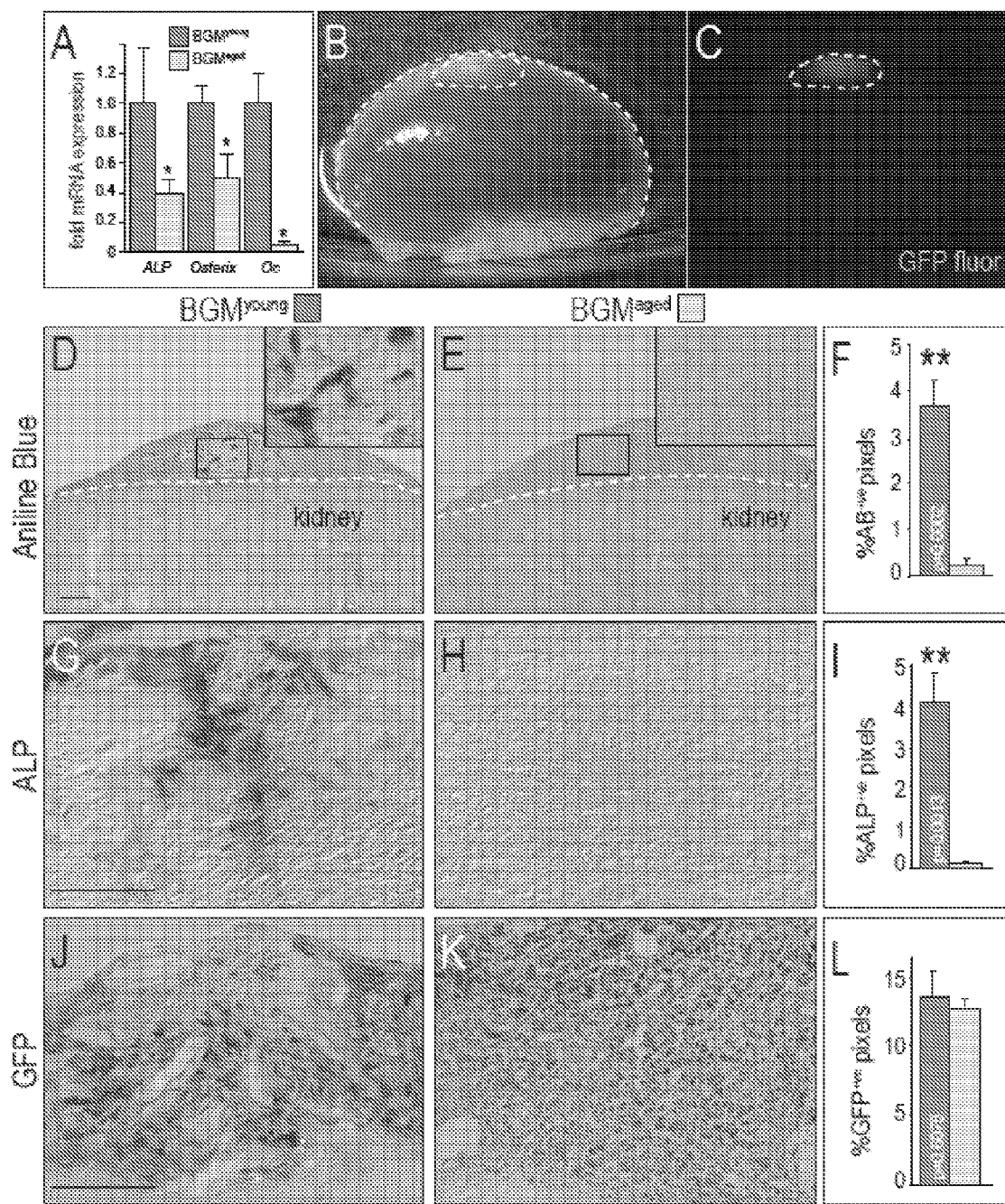
FIG. 22 shows osteogenic differentiation potential of BGM declines with age.
Figure 23:
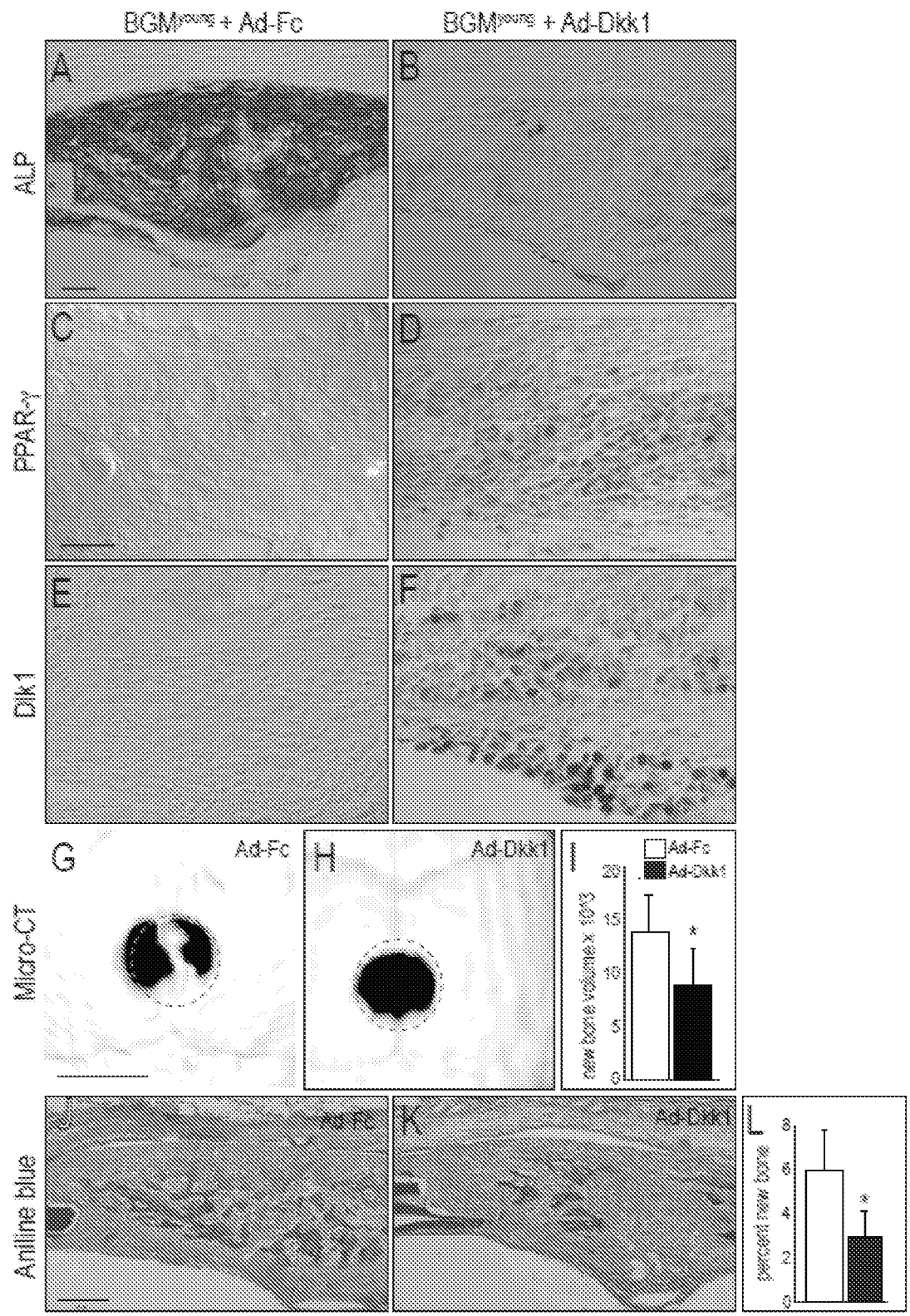
FIG. 23 shows osteogenic differentiation of BGM that requires an endogenous Wnt signal.
Figure 24:
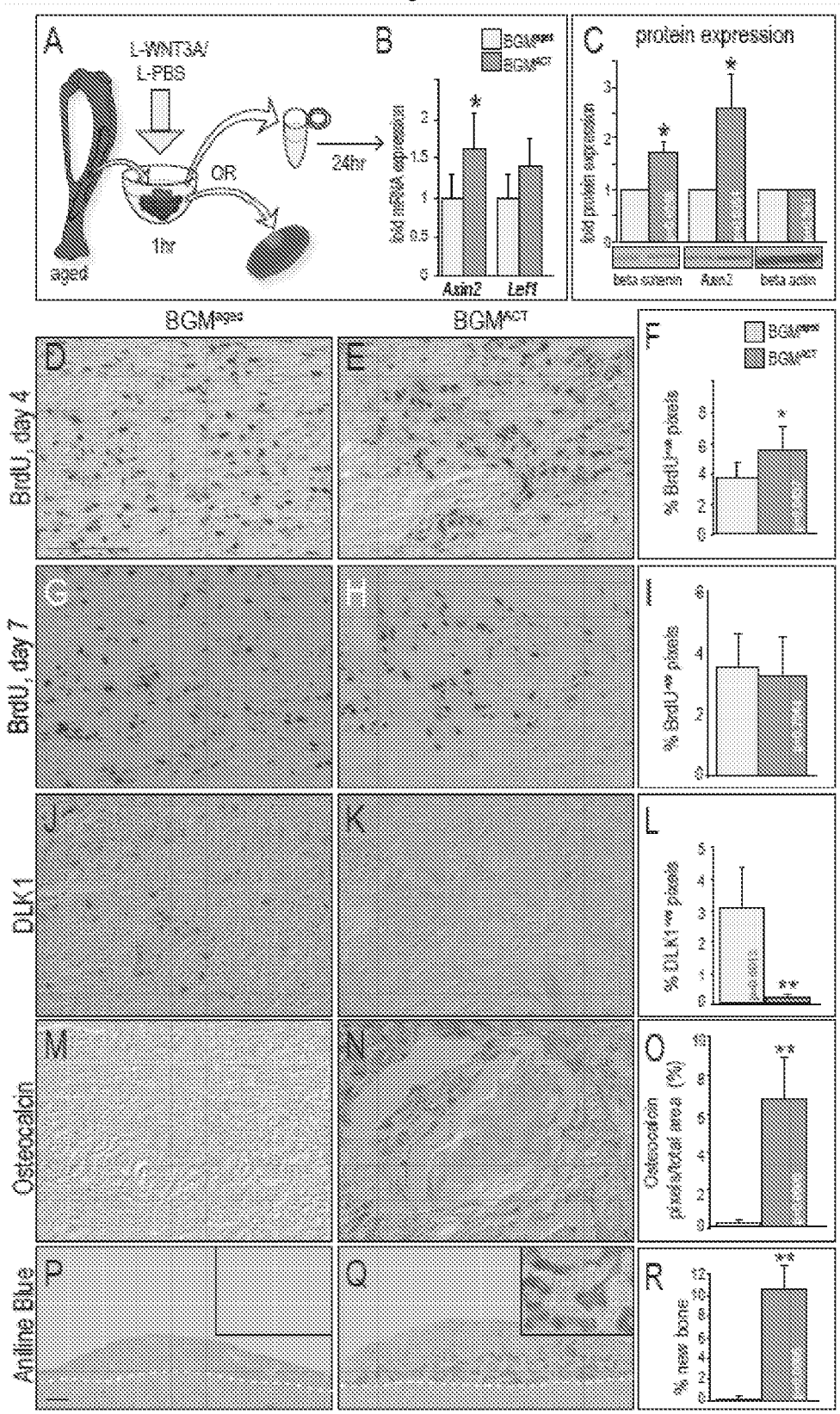
FIG. 24 illustrates human Wnt3a activation of BGM$^{aged}$ and restoration of its osteogenic differentiation potential.
Figure 25:
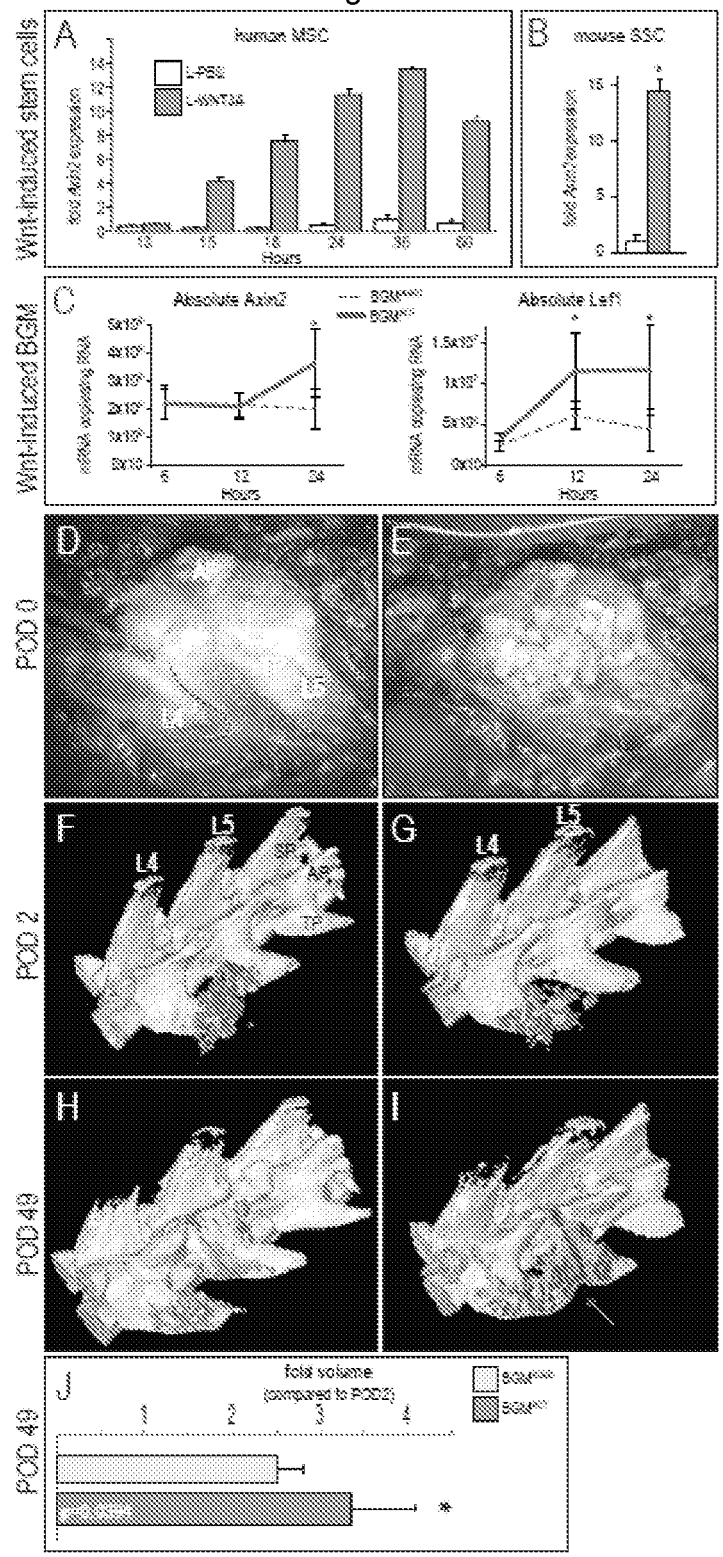
FIG. 25 illustrates L-Wnt3a stimulation of BGM stem cells and improvement of spinal fusion.

Both rats and mice were employed in this study. The use of mouse models allows for a broad spectrum of molecular analyses, however, because autografts are highly invasive for these small animals, rats were used when performing autografts (e.g., FIGS. 20 and 25), and syngeneic mice when employing advanced molecular techniques (FIGS. 21-24). In all cases, bone graft material (BGM) was harvested from femurs, tibiae and iliac crest by splitting the bones lengthwise, gently scraping the endosteal surface with a sharp instrument, and irrigating the marrow contents into a collection dish. This method mimicked the reamer/irrigator/aspirator (RIA) technique used in humans.

To induce recombination in Axin2$^{CreERT/+}$, R26R$^{mTmG/+}$ mice (FIG. 21), animals were given 160 µg/g body weight tamoxifen via IP injection or gavage for 5 consecutive days. Tissues were harvested 7 days after the first treatment and analyzed by GFP immunostaining or fluorescence.

Figure 26:
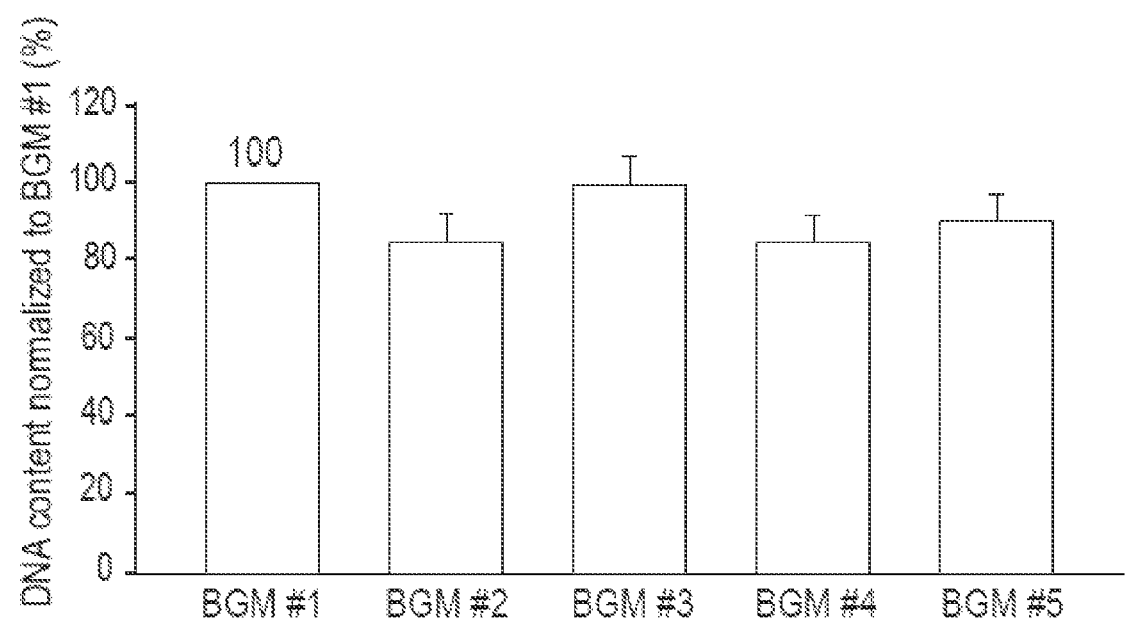
FIG. 26 illustrates quantification of BGM volume. BGM harvested from the tibiae and femurs was divided into 5 aliquots of about ~20 µL then DNA concentration was evaluated as a means to quantify cellular density in the heterogeneous mixture of cells, stroma, and bone fragments. The DNA concentration in sample #1 was set as at 100, and the relative DNA concentration of the other 4 aliquots were determined.

To ensure that BGM aliquots for transplantation into the sub-renal capsule (SRC) were equivalent in terms of cellular content, BGM from 3 mice (littermates) was pooled then divided into 20 µL aliquots just as in the transplant assays. DNA content was extracted with the DNeasy Tissue Kit (QIAGEN) and relative DNA concentration was measured using the Quant-iT PicoGreen dsDNA Kit (Invitrogen) and microplate fluorescence reader (BERTHOLD, Bad Wildbad, Germany). The percent variation in DNA content was <20% (FIG. 26).

To obtain BGM$^{ACT}$, freshly harvested BGM was placed into 20 µL of culture medium containing a liposomal formulation of either phosphate-buffered saline (L-PBS) or WNT3A (L-WNT3A, effective L-WNT3A concentration=0.15 µg/mL) and maintained at 23° C. for 1 hour.

Quantitative Reverse Transcription-Polymerase Chain Reaction (qRT-PCR)

Tissue samples were homogenized in TRIzol solution. RNA was isolated and reverse transcription was performed. Quantitative real-time PCR was carried out using Prism 7900HT Sequence Detection System and Power SYBR Green PCR Master Mix (Applied Biosystems). Levels of gene expression were determined by the ΔΔCT method and normalizing to their GAPDH values. All reactions were performed in triplicate, means and standard deviations were calculated.

Primers sequences (5' to 3') are as follows: Axin2, [for-TCATTTTCCGAGAACCCACCGC], [rev-GCTCCA-GTTTCAGTTTCTCCAGCC]; Lef1, [for-AGGAGC-CCAAAAGACCTCAT], [rev-CGTGCACTCAGCTATGACAT]; GAPDH, [for-ACCCAGAAGACTGTGGATGG] [rev-GGATGCAGGGATGATGTTCT]; ALP [for-ACCTTGACTGTGGTTACTGC, [rev-CATATAGGATGGCCGTGAAGG]; Osterix, [for-GGAGACCTTGCTCGTAGATTTC], [rev-GGGATCT-TAGTGACTGCCTAAC]; Osteocalcin, [for-TGTGAC-GAGCTATCAAACCAG], [rev-GAGGATCAAGTTCTGGAGAGC].

Western Analyses

BGM was harvested from young (N=5) and aged (N=5) mice and then placed in Dulbecco's Modified Eagle Medium (DMEM) containing 10% Fetal Bovine Serum (FBS), 100 U/mL penicillin and 100 µg/mL streptomycin, and incubated at 37° C. in 5% $CO_2$. After 24 hours, non-adherent cells were removed, media was replaced, and adherent cells were passaged until they reached confluence. Media was changed every 3 days. In some experiments, cells after passage 3 were treated with either L-PBS or L-WNT3A (effective concentration=0.03 µg/mL). In these experiments, cells were collected 24 h later and lysed using RIPA buffer. Total protein was extracted for Western analysis. Pan-actin was used as an internal control and to ensure protein integrity. Antibodies against WNT3A, non-phosphorylated β-catenin, and Axin2 were used. Integrated intensity was analyzed by ImageJ to quantify Western blotting results.

Sub-Renal Capsule Transplant Surgery

In some cases, the sub-renal capsular assay (SRCA) was employed to assay its differentiation potential. Following inhalation of anesthesia by the syngeneic host mice, a skin incision was made on the left flank directly caudal to the rib cage. The peritoneal cavity was opened to expose the kidney. A small incision was created in the renal capsule and the BGMs were carefully placed under the capsule using soft plastic tubing. The kidney was then returned to the peritoneal cavity, and the peritoneum and skin were closed with sutures. Buprenorphine (0.05 mg/kg) was used for analgesia.

In cases where the BGM was harvested from Axin2$^{CreERT2}$;R26$^{mTmG}$ donors, hosts were subsequently provided tamoxifen by gavage (100 µL of 10 mg/mL) beginning on day 0 for 5 days. The SRC transplants were harvested at the time points indicated.

Adenovirus-Mediated Inhibition of Wnt Signaling

DKK1 and the negative control Fc adenoviral constructs were generated. The adenoviral constructs were transfected into 293T cells. After 2 days, cells were collected, lysed, and precipitated by centrifugation. The purified adenovirus was aliquoted and stored at −80° C. Wnt inhibition was achieved by in vitro incubation of BGMs with Ad-Dkk1 and the control Ad-Fc for 2 hours, and the BGM aliquots were then transplanted into calvarial defects.

Calvarial Critical-Size Defect Surgery

Mice were anesthetized, and a 3-mm incision was made to expose the parietal bone. A circumferential, full-thickness defect with a 2-mm diameter was created with the use of a micro-dissecting trephine; the dura mater was not disturbed. BGM aliquots were incubated with Ad-Dkk1 and the control Ad-Fc for 2 hours. BGM aliquots were then transplanted into the calvarial defect and the skin was closed with sutures. Following recovery from surgery, mice received Buprenorphine for analgesia.

Micro-computed tomography (Micro-CT) analyses were performed as follows. Mice were anesthetized with 2% isoflurane and scanned with use of a multimodal positron emission tomography-computed tomography data-acquisition system (Inveon PET-CT) at 40-µm resolution. Data were analyzed with MicroView software. The three-dimensional region-of-interest tool was used to assign the structure and bone volume for each sample.

Assessment of the regenerate bone volume fraction (the percentage calculated by dividing the total bone volume by the regenerate bone volume [BV/TV, %]) was performed with the use of high-resolution micro-CT (vivaCT 40), with 70 kVp, 55 µA, 200-ms integration time, and a 10.5-µm isotropic voxel size. The region of interest was 2 cm in length and began 250 µm proximal to the edge of the defect and extended 250 µm distally beyond the opposing edge of the defect (1.5 cm total diameter). Bone was segmented from soft tissue with use of a threshold of 275 mg/cm3 hydroxyapatite. Scanning and analyses adhered to published guidelines.

Spinal Fusion Surgery

Lewis Rats were anesthetized using a cocktail of Ketamine 70-100 mg/kg and Xylazine 5-10 mg/kg. The lumbar region of the rats were shaved then disinfected with Betadine-soaked gauze. Prior to the skin incision, the rats were injected with the analgesia buprenorphine 0.02 mg/kg SC/IP. First, bone graft material (BGM) was harvested from the iliac crest; briefly, the left iliac spine was palpated and a vertical cutaneous incision was made; the dorsal crest of the iliac spine was accessed and exposed through blunt dissection. The attached muscle and periosteum were elevated and 0.3 g of BGM was harvested with rongeur forceps and morselized. BGM was then incubated with either 100 µL L-PBS or with 100 µL of [0.15 µg/mL] L-Wnt3a while the transverse processes were exposed.

To expose the transverse processes, posterolateral blunt dissection was performed and the reflected paraspinal muscles were held in place by retractors. The transverse processes of L4-L5 were cleaned of periosteum and decorticated with a bur. The BGM was spread over and between the L4-L5 transverse processes. The paraspinal muscles were closed with absorbable sutures (4-0 Vicryl, Ethicon) and the skin with interrupted non-absorbable sutures (4-0 Nylon, Ethicon). The surgical site was treated with an antibiotic ointment. 10 mg/kg Baytril was delivered subcutaneously. Buprenorphine (0.02 mg/kg) was administered after surgery for 3 days, and subsequent doses were given as needed to control pain.

Sample Preparation, Tissue Processing, Histology

Tissues were fixed in 4% paraformaldehyde (PFA) overnight at 4° C. Samples were decalcified in 19% EDTA for 1 day. Specimens were dehydrated through an ascending ethanol series prior to paraffin embedding. Eight-micron-thick longitudinal sections were cut and collected on Superfrost-plus slides for histology. Safranin O, Aniline blue and Gomori staining were performed. Tissue sections were photographed using a Leica DM5000B digital imaging system.

ALP, TRAP and TUNEL Staining

Alkaline phosphatase (ALP) activity was detected by incubation in nitro blue tetrazolium chloride (NBT), 5-bromo-4-chloro-3-indolyl phosphate (BCIP), and NTM buffer (100 mM NaCl, 100 mM Tris pH9.5, 5 mM MgCl). Tartrate-resistant acid phosphatase (TRAP) activity was observed using a Leukocyte acid phosphatase staining kit following manufacturer's instructions. After developing, slides were dehydrated in a series of ethanol, cleaned in Citrisolv, and cover-slipped with Permount mounting media. For TUNEL staining, sections were permeabilized using 0.1% Triton X-100 and 0.1% sodium citrate, and incubated with TUNEL reaction mixture (In Situ Cell Death Detection Kit). Sections were mounted with DAPI mounting medium and visualized under an epifluorescence microscope.

For bromodeoxyuridine (BrdU) assay, mice were given intraperitoneal injections of BrdU labeling reagent (Invitrogen, CA, USA) and euthanized 4 hours post-injection. BrdU detection was carried out using BrdU Staining Kit following the manufacturer's instructions.

Immunohistochemistry

Tissue sections were deparaffinized and rehydrated in PBS. Endogenous peroxidase activity was quenched by 3% hydrogen peroxide for 5 min, and then washed in PBS. Slides were blocked with 5% goat serum for 1 hour at room temperature. The appropriate primary antibody was added and incubated overnight at 4° C. Samples were then incubated with appropriate biotinylated secondary antibodies and advidin/biotinylated enzyme complex and developed by a DAB substrate kit. Antibodies used included GFP and DLK1, Runx2, Sox9 and PPAR-γ.

Micro-CT Analyses and Quantification of Graft Growth

Scanning and analyses adhered to published guidelines. Rats were anesthetized with 2% isoflurane and scanned with a micro computed tomography data-acquisition system (Inveon) at a 52-µm resolution. To define the graft growth that occurred in each sample, POD2 and POD49 timepoint scanning data were exported into Osirix software version 5.8 and registered for segmentation in the same orientation. The new bone that formed was compared to the initial BGM volume transplanted. Differences between sets of data were determined by using Mann-Whitney test in XLStat software version. A p-value <0.05 was considered statistically significant.

Quantification and Statistical Analyses

GFP, BrdU, TUNEL, DLK1, Osteocalcin and Aniline blue stainings were quantified. Photoshop CS5 was used to determine the number of pixels in the region of interest (ROI), at the injury site. The magic wand tool was used to assign the area of positive pixels within the ROI. The ratio of pixels of positive signals to pixels of ROI was expressed as a percentage. At least 5 sections evenly spaced across the injury sites were quantified to determine the average value of each sample. Five samples were included in each group (n=5). Results are presented as the mean±SD. Student's t-test was used to quantify differences described herein. P≤0.05 was considered significant.

Bone Graft Material Contains Multiple Stem/Progenitor Cell Populations

In some cases, the optimal anatomical site for harvesting autografts depends upon a number of factors including donor site morbidity and the availability of bone stock. The BGM was harvested from three anatomical sites using a modified reamer-irrigator-aspirator (RIA) technique and noted that the femur, iliac crest, and tibia yielded BGM with distinctly different histological appearances. In addition to hematopoietic cells, femur BGM contained adipocytes, even when harvested from young animals (FIG. 20A). Iliac crest BGM was largely comprised of trabecular bone fragments covered in tightly adherent cells (FIG. 20B). BGM from the tibia contained a considerable amount of fibrous stroma and small, anucleated cells (FIG. 20C). A quantitative RT-PCR was used to evaluate endogenous osteogenic gene expression and found that of the three sources, iliac crest BGM expressed alkaline phosphatase and Osteocalcin at significantly higher levels (FIG. 20D).

In some cases, it is believed that the osteogenic property of an autograft is attributable to stem/progenitor cell populations and osteoblasts within the bone graft material (BGM). This osteogenic property of an autograft was tested by transplanting BGM into a sub-renal capsule (SRC) assay. The SRC provides a vascular supply to the transplanted tissue and supports the differentiation of cells into multiple kinds of tissues including bone, skin, muscle, teeth, organs, and tumors. BGM was harvested from the iliac crest, then transplanted beneath the animal's kidney capsule (FIG. 20A) and allowed to develop there for 7 days.

BrdU incorporation demonstrated the high mitotic activity of cells in the autologous BGM (FIG. 20B). Immunostaining for Runx2 (FIG. 20C), Sox9 (FIG. 20D) and PPARγ (FIG. 20E) demonstrated that subsets of cells in the BGM expressed gene markers associated with osteogenic, chondrogenic and adipogenic commitment. On day 7, a subpopulation of BGM-derived cells had differentiated into bone (FIG. 20F), cartilage (FIG. 20G), and fat (FIG. 20H). Together, these data demonstrated that the BGM contained stem/progenitor cells capable of differentiating into all three lineages.

Wnt Signaling in Bone Graft Material Declines with Age

Axin2$^{CreERT2}$; R26$^{mTmG}$ reporter mice were used to induce recombination which lead to the identification of GFP$^{+ve}$ pre-osteoblasts in the periosteum (FIG. 21A) and the endosteum (FIG. 21B). The frequency of GFP$^{+ve}$ cells in the endosteum was ~0.1% (FIG. 21C). GFP$^{+ve}$ cells were also identified in freshly harvested BGM (FIG. 21D). Thus, a subset of cells in the heterogeneous BGM is Wnt responsive.

The Wnt responsive status of BGM was compared between young (<3 month old) and aged (>10 month old) mice. Quantitative absolute RT-PCR demonstrated that expression of the Wnt target genes Axin2 and Lef1 was almost two-fold lower in BGM harvested from aged mice (BGM$^{aged}$) v. young mice (BGM$^{young}$; FIG. 21F). Western analysis confirmed that Wnt3a, phosphorylated beta catenin, and Axin2 expression were all significantly lower in BGM$^{aged}$ compared to BGM$^{young}$ (FIG. 21G). Thus, the endogenous Wnt responsive status of BGM deteriorates with age.

Osteogenic Differentiation Capacity Also Declines with Age

In humans, the rate of bone healing declines with age. A similar age-related decline was also found in the osteogenic capacity of BGM in mice. Freshly harvested BGM$^{aged}$ showed significantly lower expression levels of the osteogenic genes Alkaline phosphatase, Osterix, and Osteocalcin compared to freshly harvested BGM$^{young}$ (FIG. 22A).

To test whether the reduction in osteogenic gene expression affected the osteogenic capacity of the BGM, the SRC assay was used. Performing an autograft in a mouse, however, is excessively traumatic. To mimic an autograft, syngeneic donors and hosts were used. Because syngeneic animals are so closely related, their tissues are immunologically compatible and transplantation of tissues does not provoke an immune response. ACTB-eGFP mice served as the donors and BGM was readily identifiable in the SRC by its GFP fluorescence (FIG. 22B, FIG. 22C).

Seven days after transplantation, BGM was harvested and analyzed for evidence of bone formation. Aniline blue stained osteoid matrix was evident in BGM$^{young}$ (FIG. 22D) but absent in BGM$^{aged}$ (FIG. 22E; quantified in FIG. 22F). The osteoid matrix in BGM$^{young}$ was undergoing mineralization as shown by ALP staining (FIG. 22G) whereas BGM$^{aged}$ showed no ALP staining (FIG. 22H; quantified in I). Further, the GFP immunostaining demonstrated that in both BGM$^{young}$ (FIG. 22J) and BGM$^{aged}$ (FIG. 22K) there were a similar number of surviving donor cells (quantified in FIG. 22L). Together these data indicated that osteogenic gene expression and osteogenic capacity of BGM declined with age.

Wnt Signaling and the Osteogenic Capacity of BGM

Endogenous Wnt responsiveness and the osteogenic capacity of BGM diminish with age. To test whether reduced Wnt signaling contributed to this age-related decline in osteogenic potential, endogenous Wnt signaling in BGM was blocked. Over-expression of the Wnt inhibitor, Dkk1, was also used to transiently abolish Wnt signaling in vivo. Either Ad-Dkk1 or Ad-Fc (control) was delivered to the bone marrow cavity of young mice then harvested BGM$^{young}$ 24 h later and transplanted the aliquots into critical size (non-healing) skeletal defects.

Seven days later, when control BGM$^{young}$ was strongly positive for ALP activity (FIG. 23A), Ad-Dkk1 treated BGM$^{young}$ showed minimal activity (FIG. 23B). Instead, Ad-Dkk1 treated BGM$^{young}$ showed widespread expression of the adipogenic proteins PPAR-γ (FIG. 23C, FIG. 23D) and DIM (FIG. 23E, FIG. 23F). Bone formation was repressed by Ad-Dkk1 treatment, as shown by micro-CT (FIG. 23G, FIG. 23H; quantified in FIG. 23I) and histomorphometric analyses of the BGM (FIG. 23J, FIG. 23K; quantified in FIG. 23L). Thus, the osteogenic capacity of BGM relies upon an endogenous Wnt signal.

Augmenting the Endogenous Wnt Signal in BGM$^{aged}$ Restores its Osteogenic Capacity FIG. 23J-FIG. 23L showed that endogenous Wnt signaling could activate osteogenic capacity of BGM. A Wnt stimulus was also tested for sufficiency to enhance BGM efficacy. BGM$^{aged}$ was harvested, treated with L-WNT3A or liposomal PBS (L-PBS), and then incubated at 37° C. (FIG. 24A). Absolute qRT-PCR analyses revealed a small elevation in Axin2 expression (FIG. 24B). Lef1 was modestly elevated in response to L-WNT3A (FIG. 24B). Western analyses indicated that both beta catenin and Axin2 proteins were elevated in response to L-WNT3A (FIG. 24C).

Mitotic activity in BGM was increased by L-WNT3A treatment. On post-transplant day 4, cell proliferation was increased in L-WNT3A treated BGM$^{aged}$ compared to L-PBS-treated BGM$^{aged}$ (FIG. 24D, FIG. 24E; quantified in FIG. 24F). The effect on cell cycling was transient by post-transplant day 7, BrdU incorporation was equivalent between the L-PBS and L-WNT3A samples (FIG. 24G, FIG. 24H; quantified in FIG. 24I).

Figure 27:
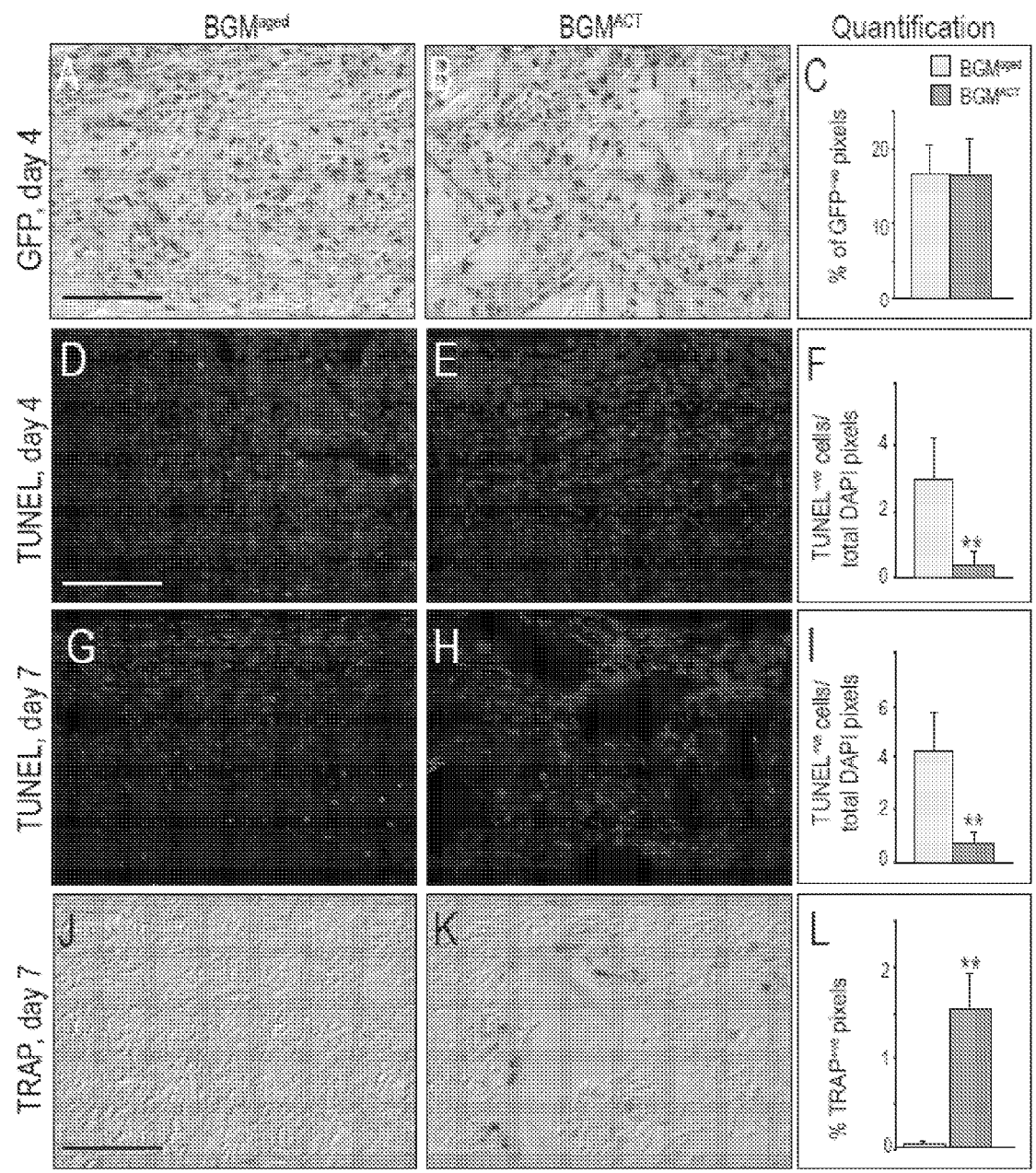
FIG. 27 illustrates engraftment efficiency of BGM. L-Wnt3a treatment improves BGM engraftment efficiency.

Cell differentiation in BGM$^{aged}$ was evaluated. Expression of the adipogenic protein Dlk1 was lower (FIG. 24J, FIG. 24K; quantified in FIG. 24L) and expression of the osteogenic protein Osteocalcin was higher in L-WNT3A treated BGM$^{aged}$ (FIG. 24M, FIG. 24N; quantified in FIG. 24O). New bone formation was found only in L-WNT3A treated BGM$^{aged}$ (FIG. 24P, FIG. 24Q; quantified in FIG. 24R). Treatment with L-WNT3A did not affect engraftment efficiency (FIG. 27A,B; quantified in FIG. 27C) but analyses of programmed cell death demonstrated that L-WNT3A treated BGM$^{aged}$ had fewer TUNEL$^{+ve}$ cells than L-PBS treated samples (FIG. 27D, FIG. 27E; quantified in FIG. 27F). Reduced apoptosis was also observed at post-transplant day 7 (FIG. 27G, FIG. 27H; quantified in FIG. 27I). New bone formation served as a stimulus for osteoclast-mediated bone remodeling and TRAP activity was observed around the newly formed osteoid matrix in L-WNT3A treated BGM$^{aged}$ samples (FIG. 27J, FIG. 27K; quantified in FIG. 27L).

L-WNT3A Activates Stem Cells in BGM$^{aged}$ and Improves Bone Generation in a Spinal Fusion Model The population of cells in BGM responsible for the L-WNT3A mediated surge in osteogenic capacity was also identified. Two stem cell populations from BGM using standard procedures were isolated and were evaluated based on their Wnt responsiveness using L-PBS (as control) or L-WNT3A.

Time-course analyses revealed the response of stem cells to L-WNT3A treatment. Within 15 h of L-WNT3A exposure, a 4-fold activation in Axin2 was observed, and maximal Axin2 activation was achieved at 36 h (FIG. 25A). The effect was transient, as shown by diminished Axin2 expression in stem cells at the 60 h timepoint (FIG. 25A). A second stem cell population isolated from BGM was used to verify that stem cells responded to L-WNT3A (FIG. 25B).

The activated state of the BGM was shown by qRT-PCR. BGM$^{aged}$ was harvested, treated with L-WNT3A or L-PBS, then analyzed using Axin2 and Lef1 expression for its Wnt responsive status (FIG. 25C). Within 12 h an elevation in Lef1 was detectable. Within 24 h, both Axin2 and Lef1 were elevated (FIG. 25C). These analyses confirm a WNT-mediated activation state of BGM; hereafter refers to this material as BGM$^{ACT}$.

The therapeutic potential of BGM$^{ACT}$ in a rat spinal fusion model was also tested. The transverse processes of the fourth and fifth lumbar (e.g., L4-5) vertebrae were decorticated (FIG. 25D) and during this procedure, autologous BGM$^{aged}$ from the iliac crest was harvested and treated with L-WNT3A (or L-PBS) for 1 h. The resulting material, BGM$^{ACT}$ (or BGM$^{aged}$) was then transplanted onto and between the L4-5 processes (FIG. 25E). On post-operation day 2 the volume of the BGM was evaluated by micro-CT. These analyses verified that BGM$^{aged}$ (FIG. 25F) and BGM$^{ACT}$ (FIG. 25G) contained comparable amounts of mineralized tissue at the outset (see also FIG. 26).

The volume of new bone formation was re-evaluated on post-operation day 49. Three-dimensional reconstructions of the micro-CT data demonstrated poor bone regeneration in sites treated with BGM$^{aged}$ (grey; FIG. 25H). In contrast, sites treated with BGM$^{ACT}$ showed evidence of robust bone formation and fusion of the transverse processes (blue; FIG. 25I). The volume of new bone on and between the L4 and L5 transverse processes was quantified. Compared to BGM$^{aged}$, BGM$^{ACT}$ gave rise to more mineralized matrix (FIG. 25J). Thus, L-WNT3A treatment improves the osteogenic capacity of autografts from aged animals.

Example 4

Expression of Wnt3a from Vector Specific for Serum-Free CHO Cells

Wnt3a secreting CHO suspension (CHO-S) cells could be also cultured under serum-free conditions in suitable expression media, such as expression media from Invitogen. A cGMP compatible CHO-S cells line, and two types of vectors to clone WNT3A were used. One vector was pOptivec, which is a TOPO® adapted bicistronic plasmid which allows rapid cloning of a gene containing a mammalian secretion signal and the gene of interest downstream of the CMV promoter. The dihydrofolate reductase selection markers allows for rapid selection. This vector was used for transient transfection of CHO-S cells. Another vector was pTargeT. This vector was used for transient transfection of CHO-S cells and also to create a stable cell line expressing WNT3A Conditioned media (CM) from CHO cell cultures were collected between day 3 and day 13 after induction and pooled. Based on analyses of protein production in the CM on each day, this range of days was determined to be optimal under the culture conditions. Under these conditions, high protein production was observed to occur between days 3-13, while after day 13 cells began to die.

Example 5

Replacement of Serum with a Lipid-Defined Substitute

The lipid components in serum are tested to determine whether they could be replaced with a defined set of lipids. Charcoal stripping removes non-polar lipophilic materials (viruses, growth factors, hormones) from serum. In comparison to control conditions where CHO cells are grown in 10% FBS, CHO cells grown in charcoal-stripped FBS do not secrete Wnt3a. These data support the conclusion that a lipophilic component of serum is required for Wnt3a secretion. Supplementation with Lipid Mixture 1 (Sigma) containing cholesterol, tocopherol, and non-animal derived fatty (inoleic, linolenic, myristic, oleic, palmitic and stearic) acids will improve CHO cell growth rate and will restore Wnt3a secretion to CHO cells.

Example 6

Step-Wise Reduction in Serum Dependence

A sequential culturing as a means to reach a serum independent process for WNT3A production is also tested. CHO cell growth rate is reduced simultaneous with serum reduction; consequently, it is important to shift the time frame for the collection of conditioned media. In some instances, cells are adapted to 0.5% FBS.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

What is claimed is:

1. A composition comprising a functionally active Wnt3a polypeptide and an aqueous solution comprising liposomes, wherein the functionally active Wnt3a polypeptide comprises a lipid modification at an amino acid position corresponding to amino acid residue 209 as set forth in SEQ ID NO:1, wherein the liposome comprises a phospholipid that is 1,2-dimyristoyl-sn-glycero-3-phosphocholine (DMPC), wherein the liposome comprises cholesterol, and wherein the concentration of DMPC and cholesterol is defined by a ratio of between about 70:30 and about 90:10.

2. The composition of claim 1, wherein the functionally active Wnt3a polypeptide is not lipid modified at an amino acid position corresponding to amino acid residue 77 as set forth in SEQ ID NO:1.

3. The composition of claim 1, wherein the functionally active Wnt3a polypeptide is integrated into the liposomal membrane, protrudes from the liposomal membrane onto the outer surface of the lipid membrane, and is not incorporated into the aqueous core of the liposome.

4. The composition of claim 1, wherein the functionally active Wnt3a polypeptide comprises at least about 30%, about 40%, about 50%, about 60%, about 70%, about 80%, about 90%, or about 95% sequence identity to the amino acid sequence as set forth in SEQ ID NO:1 or comprises the amino acid sequence as set forth in SEQ ID NO:1.

5. The composition of claim 1, wherein the liposome has a net charge of 0 at a pH of between about 6.5 and about 8.0, about 7.0 and about 7.8, or about 7.2 and about 7.6.

6. The composition of claim 1, wherein the lipid modification is palmitoylation.

7. A kit for generating bone graft materials comprising the liposomal Wnt3a polypeptide of claim 1.

8. A composition comprising a functionally active mammalian Wnt polypeptide and an aqueous solution comprising liposomes, wherein the liposome comprises a phospholipid that is 1,2-dimyristoyl-sn-glycero-3-phosphocholine (DMPC), wherein the liposome comprises cholesterol, and wherein the concentration of DMPC and cholesterol is defined by a ratio of between about 70:30 and about 90:10.

9. A method of preparing a liposomal Wnt3a polypeptide, comprising:
   a) harvesting Wnt3a polypeptides from a condition media comprising Chinese hamster ovary (CHO) cells;
   b) introducing the Wnt3a polypeptides to an ion-exchange column immobilized with a sulfonated polyaromatic compound;
   c) eluting the Wnt3a polypeptides from the ion-exchange column utilizing a step gradient comprising a first gradient and a second gradient, wherein the first gradient comprises about 50 mM concentration of a first salt and the second gradient comprises between about 150 mM and about 1.5M concentration of a second salt; and
   d) contacting the Wnt3a polypeptides from step (c) with an aqueous solution of liposomes.

10. A method of preparing a liposomal Wnt polypeptide, comprising contacting a sample comprising Wnt polypeptides to an aqueous solution of liposomes, wherein the liposome comprises a phospholipid that is 1,2-dimyristoyl-sn-glycero-3-phosphocholine (DMPC), wherein the liposome comprises cholesterol, and wherein the concentration of DMPC and cholesterol is defined by a ratio of between about 70:30 and about 90:10.

11. The method of claim 9, wherein the first gradient comprises a buffer solution comprising 50 mM potassium chloride, and the second gradient comprises a buffer solution comprising between about 150 mM potassium chloride and about 1.5 M potassium chloride.

12. The method of claim 11, wherein the buffer solution further comprises a detergent.

13. The method of claim 12, wherein the detergent is CHAPS or Triton X-100.

14. The method of claim 9, wherein the condition media comprises up to 10% fetal bovine serum.

15. The method of claim 9, wherein the yield of the Wnt3a polypeptides after step (c) is between about 60% and about 90%.

16. The method of claim 9, wherein the liposome has a net charge of 0 at a pH of between about 6.5 and about 8.0, about 7.0 and about 7.8, or about 7.2 and about 7.6.

17. The method of claim 9, wherein the Wnt3a polypeptide is lipid modified at an amino acid position corresponding to amino acid residue 209 as set forth in SEQ ID NO:1.

18. The method of claim 9, wherein the Wnt3a polypeptide is not lipid modified at an amino acid position corresponding to amino acid residue 77 as set forth in SEQ ID NO:1.

19. The method of claim 9, wherein the first salt and the second salt are the same.

* * * * *

SEQUENCE LISTING

<160> NUMBER OF SEQ ID NOS: 2

<210> SEQ ID NO 1
<211> LENGTH: 352
<212> TYPE: PRT
<213> ORGANISM: Homo sapiens

<400> SEQUENCE: 1

```
Met Ala Pro Leu Gly Tyr Phe Leu Leu Leu Cys Ser Leu Lys Gln Ala
 1               5                  10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
```

|       |     |     |     |     |     |     |     |     |     |     |     |     |     |
|---|---|---|---|---|---|---|---|---|---|---|---|---|---|
|       |     | 50  |     |     |     | 55  |     |     |     | 60  |     |     |     |
| Ser | Val | Ala | Glu | Gly | Ile | Lys | Ile | Gly | Ile | Gln | Glu | Cys | Gln | His | Gln |
| 65  |     |     |     | 70  |     |     |     | 75  |     |     |     | 80  |     |     |     |

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 2
<211> LENGTH: 2826
<212> TYPE: DNA
<213> ORGANISM: Homo sapiens

<400> SEQUENCE: 2

```
atggccccac tcggatactt cttactcctc tgcagcctga agcaggctct gggcagctac      60
ccgatctggt ggtcgctggc tgttgggcca cagtattcct ccctgggctc gcagcccatc     120
ctgtgtgcca gcatcccggg cctggtcccc aagcagctcc gcttctgcag gaactacgtg     180
gagatcatgc ccagcgtggc cgagggcatc aagattggca tccaggagtg ccagcaccag     240
ttccgcggcc gccggtggaa ctgcaccacc gtccacgaca gcctggccat cttcgggccc     300
gtgctggaca agctaccagg gagtcggcc tttgtccacg ccattgcctc agccggtgtg     360
gccttttgca tgacacgctc atgtgcagaa ggcacggccg ccatctgtgg ctgcagcagc     420
cgccaccagg gctcaccagg caagggctgg aagtggggtg gctgtagcga ggacatcgag     480
```

```
tttggtggga tggtgtctcg ggagttcgcc gacgcccggg agaaccggcc agatgcccgc    540
tcagccatga accgccacaa caacgaggct gggcgccagg ccatcgccag ccacatgcac    600
ctcaagtgca agtgccacgg gctgtcgggc agctgcgagg tgaagacatg ctggtggtcg    660
caacccgact tccgcgccat cggtgacttc ctcaaggaca agtacgacag cgcctcggag    720
atggtggtgg agaagcaccg ggagtcccgc ggctgggtgg agaccctgcg gccgcgctac    780
acctacttca aggtgcccac ggagcgcgac ctggtctact acgaggcctc gcccaacttc    840
tgcgagccca accctgagac gggctccttc ggcacgcgcg accgcacctg caacgtcagc    900
tcgcacggca tcgacggctg cgacctgctg tgctgcggcc gcggccacaa cgcgcgagcg    960
gagcggcgcc gggagaagtg ccgctgcgtg ttccactggt gctgctacgt cagctgccag   1020
gagtgcacgc gcgtctacga cgtgcacacc tgcaagtagg caccggccgc ggctcccct   1080
ggacggggcg ggccctgcct gagggtgggc ttttccctgg gtggagcagg actcccacct   1140
aaacggggca gtactcctcc ctgggggcgg gactcctccc tggggtgggg gctcctacct   1200
gggggcagaa ctcctacctg aaggcagggc tcctccctgg agctagtgtc tcctctctgg   1260
tggctgggct gctcctgaat gaggcggagc tccaggatgg ggaggggctc tgcgttggct   1320
tctccctggg gacggggctc ccctggacag aggcggggct acagattggg cggggcttct   1380
cttgggtggg acaggcttc tcctgcgggg gcgaggcccc tcccagtaag ggcgtggctc   1440
tgggtgggcg gggcactagg taggcttcta cctgcaggcg gggctcctcc tgaaggaggc   1500
ggggctctag gatggggcac ggctctgggg taggctgctc cctgagggcg gagcgcctcc   1560
ttaggagtgg ggttttatgg tggatgaggc ttcttcctgg atggggcaga gcttctcctg   1620
accagggcaa ggccccttcc acggggggctg tggctctggg tgggcgtggc ctgcataggc   1680
tccttcctgt gggtggggct tctctgggac caggctccaa tggggcgggg cttctctccg   1740
cgggtgggac tcttccctgg gaaccgccct cctgattaag gcgtggcttc tgcaggaatc   1800
ccggctccag agcaggaaat tcagcccacc agccacctca tccccaaccc cctgtaaggt   1860
tccatccacc cctgcgtcga gctgggaagg ttccatgaag cgagtcgggt ccccaacccg   1920
tgcccctggg atccgagggc ccctctccaa gcgcctggct ttggaatgct ccaggcgcgc   1980
cgacgcctgt gccaccccct cctcagcctg gggtttgacc acccacctga ccaggggccc   2040
tacctgggga aagcctgaag ggcctcccag cccccaaccc caagaccaag cttagtcctg   2100
ggagaggaca gggacttcgc agaggcaagc gaccgaggcc ctcccaaaga ggcccgccct   2160
gcccgggctc ccacaccgtc aggtactcct gccaggaaac tggcctgctg cgccccaggc   2220
cccgcccgtc tctgctctgc tcagctgcgc cccttctttt gcagctgccc agcccctcct   2280
ccctgccctc gggtctcccc acctgcactc catccagcta caggagagat agaagcctct   2340
cgtcccgtcc ctcccttttcc tccgcctgtc cacagcccct taagggaaag gtaggaagag   2400
aggtccagcc cccagagctg cccagagctg ctggtctcat ttgggggcgt cgggaggtt    2460
tgggggcat caaccccccg actgtgctgc tcgcgaaggt cccacagccc tgagatgggc   2520
cggcccccctt cctggcccct catggcggga ctggagaaat ggtccgcttt cctggagcca   2580
atggcccggc cctcctgac tcatccgcct ggcccgggaa tgaatgggga ggccgctgaa   2640
cccacccggc ccatatccct ggttgcctca tggccagcgc ccctcagcct ctgccactgt   2700
gaaccggctc ccaccctcaa ggtgcgggga gaagaagcgg ccaggcgggg cgccccaaga   2760
```

```
gcccaaaaga gggcacaccg ccatcctctg cctcaaattc tgcgtttttg gttttaatgt    2820
tatatc                                                               2826
```